US011773421B2

(12) United States Patent
Yanez et al.

(10) Patent No.: US 11,773,421 B2
(45) Date of Patent: Oct. 3, 2023

(54) METHOD FOR PRODUCING FRUCTOSE-6-PHOSPHATE FROM DIHYDROXY ACETONE PHOSPHATE AND GLYCERALDEHYDE-3-PHOSPHATE

(71) Applicant: Global Bioenergies, Evry (FR)

(72) Inventors: Alfredo Alarcon Yanez, Grenoble (FR); Samia Boudah, Vincennes (FR); Romain Chayot, Paris (FR)

(73) Assignee: Global Bioenergies, Evry (FR)

( * ) Notice: Subject to any disclaimer, the term of this patent is extended or adjusted under 35 U.S.C. 154(b) by 166 days.

(21) Appl. No.: 17/263,401

(22) PCT Filed: Jul. 26, 2019

(86) PCT No.: PCT/EP2019/070147
§ 371 (c)(1),
(2) Date: Jan. 26, 2021

(87) PCT Pub. No.: WO2020/021051
PCT Pub. Date: Jan. 30, 2020

(65) Prior Publication Data
US 2022/0112532 A1    Apr. 14, 2022

(30) Foreign Application Priority Data
Jul. 27, 2018   (EP) ..................... 18186082

(51) Int. Cl.
*C12P 19/02* (2006.01)
*C12N 9/16* (2006.01)
*C12N 9/88* (2006.01)
*C12N 9/90* (2006.01)

(52) U.S. Cl.
CPC ............. *C12P 19/02* (2013.01); *C12N 9/16* (2013.01); *C12N 9/88* (2013.01); *C12N 9/90* (2013.01); *C12Y 202/01002* (2013.01); *C12Y 301/03001* (2013.01); *C12Y 301/03002* (2013.01); *C12Y 301/03021* (2013.01); *C12Y 301/03023* (2013.01); *C12Y 301/03038* (2013.01); *C12Y 301/03074* (2013.01); *C12Y 401/02* (2013.01); *C12Y 504/02002* (2013.01); *C12Y 504/02008* (2013.01)

(58) Field of Classification Search
CPC ..... C12Y 301/03023; C12P 19/02; C12P 7/28
See application file for complete search history.

(56) References Cited

FOREIGN PATENT DOCUMENTS

| CN | 107815444 A | 3/2018 |
| EP | 3315610 A1 | 5/2018 |
| WO | 2013007786 A1 | 1/2013 |

OTHER PUBLICATIONS

ANON.: "Information on EC 2.2.1 2—transaldolase", Dec. 13, 2016 (Dec. 13, 2016), XP002795112, Retrieved from the Internet: URL:https://www.brenda-enzymes.info/enzyme.php?ecno=2.2.1.2#SUBSTRATE [retrieved on Oct. 21, 2019] the whole document.
ANON.: "Information on EC 3.1.3.23—sugar-phosphatase", May 22, 2016 (May 22, 2016), XP002795111, Retrieved from the Internet: URL:https://www.brenda-enzymes.info/enzyme.php?ecno=3.1.3.23#SUBSTRATE [retrieved on Oct. 21, 2019] the whole document.
ANON.: "Information on EC 4.1.2.13—fructose-bisphosphate aldolase", Mar. 8, 2016 (Mar. 8, 2016), XP002795113, Retrieved from the Internet: URL:https://www.brenda-enzymes.info/enzyme.php?ecno=4.1.2.13#SUBSTRATE [retrieved on Oct. 21, 2019] the whole document.
ANON.: Information on EC 5.4.2.2—phosphoglucomutase (alpha-D-glucose-1,6-bisphosphate-dependent) Mar. 8, 2016 (Mar. 8, 2016), XP002795115, Retrieved from the Internet: URL:https://www.brenda-enzymes.info/enzyme.php?ecno=5.4.2.2#SUBSTRATE [retrieved on Oct. 2019] the whole document.
Database WPI Week 201827 Thomson Scientific, London, GB; AN 2018-238835, XP002795110, & CN 107 815 444 A (Tianjin Inst Ind Biotechnology) Mar. 20, 2018 (Mar. 20, 2018) abstract.
International Search Report and Written Opinion dated Oct. 4, 2019 and received in PCT/EP2019/070147.
International Preliminary Report on Patentability dated Feb. 11, 2021 and received in PCT/EP2019/070147.

*Primary Examiner* — Tekchand Saidha
(74) *Attorney, Agent, or Firm* — InHouse Patent Counsel, LLC; Michele Wales

(57) ABSTRACT

Described is a method for the production of fructose-6-phosphate (F6P) from dihydroxyacetone phosphate (DHAP) and glyceraldehyde-3-phosphate (G3P) comprising the steps of:
(a) enzymatically converting dihydroxyacetone phosphate (DHAP) into dihydroxyacetone (DHA); and
(b) enzymatically converting the thus produced dihydroxyacetone (DHA) and glyceraldehyde-3-phosphate (G3P) into fructose-6-phosphate (F6P); or
comprising the steps of:
(a') enzymatically converting glyceraldehyde-3-phosphate (G3P) into glyceraldehyde; and
(b') enzymatically converting the thus produced glyceraldehyde together with dihydroxyacetone phosphate (DHAP) into fructose-1-phosphate (F1P); and
(c') enzymatically converting the thus produced fructose-1-phosphate (F1P) into fructose-6-phosphate (F6P).

18 Claims, 2 Drawing Sheets

Specification includes a Sequence Listing.

METHOD FOR PRODUCING FRUCTOSE-6-PHOSPHATE FROM DIHYDROXY ACETONE PHOSPHATE AND GLYCERALDEHYDE-3-PHOSPHATE

CROSS-REFERENCE TO RELATED APPLICATIONS

This application is a § 371 National Stage Application of PCT/EP2019/070147 filed on Jul. 26, 2019, which claims priority to EP 18186082.6 filed on Jul. 27, 2018, both of which are hereby incorporated by reference in their entirety.

The present invention relates to a method for the production of fructose-6-phosphate (F6P) from dihydroxyacetone phosphate (DHAP) and glyceraldehyde-3-phosphate (G3P) comprising the steps of:
(a) enzymatically converting dihydroxyacetone phosphate (DHAP) into dihydroxyacetone (DHA); and
(b) enzymatically converting the thus produced dihydroxyacetone (DHA) together with glyceraldehyde-3-phosphate (G3P) into fructose-6-phosphate (F6P) or
comprising the steps of:
(a') enzymatically converting glyceraldehyde-3-phosphate (G3P) into glyceraldehyde; and
(b') enzymatically converting the thus produced glyceraldehyde together with dihydroxyacetone phosphate (DHAP) into fructose-1-phosphate (F1P); and
(c') enzymatically converting the thus produced fructose-1-phosphate (F1P) into fructose-6-phosphate (F6P).

For the past several decades, practitioners of metabolic engineering have endeavored to provide biological solutions for the production of chemicals, thus, providing alternatives to more traditional chemical processes. In general, biological solutions allow for the utilization of renewable feedstocks (e.g. sugars) and compete with existing petrochemical based processes. A multi-step, biological solution for the production of a chemical typically comprises a microorganism as the catalyst for the conversion of feedstock to a target molecule. A complete set of enzyme reactions for the production of a particular target molecule can be grouped into those belonging to central carbon pathways and those belonging to the product specific pathway. The reactions belonging to central carbon and product specific pathways are linked in that redox (typically, NAD(P)H) and energetic (typically, ATP) constraints of each and every enzyme reaction must be accounted for in an overall balance contributing to the competitiveness of the process. Historically, central carbon pathways of heterotrophs growing on sugars have been described as the Embden-Meyerhoff-Parnas pathway (EMPP), the pentose phosphate pathway (PPP), the Entner-Doudoroff pathway (EDP), and the phosphoketolase pathway (PKP) (see Gottschalk (1986), Bacterial Metabolism, $2^{nd}$ Edition, Springer-Verlag, New York). Each central pathway or combinations of central pathways offer advantages and disadvantages with respect to a specific target molecule. In order to provide competitive bioprocesses, recombinant microorganisms with modifications involving the EMPP, PPP and EDP have been described (M. Emmerling et al., Metab. Eng. 1:117 (1999); L. O. Ingram et al., Appl. Environ. Microbiol. 53: 2420 (1987); C. T. Trinh et al., Appl. Environ. Microbiol. 74:3634 (2008)). More recently, recombinant microorganisms with modifications involving the PKP have been described (see Sonderegger et al. Appl. Environ. Microbiol. 70 (2004), 2892-2897, U.S. Pat. No. 7,253,001, Chinen et al. J. Biosci. Bioeng. 103 (2007), 262-269, U.S. Pat. No. 7,785,858; Fleige et al., Appl. Microbiol. Cell Physiol. 91 (2011), 769-776).

The EMPP converts 1 mol glucose to 2 mol pyruvate (PYR). When acetyl-CoA is desired, 1 mol PYR can be converted to 1 mol of acetyl-CoA with the concomitant generation of 1 mol $CO_2$ and 1 mol NADH. The sum of the reactions is given in Equation 1.

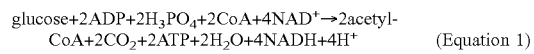

$$\text{glucose}+2ADP+2H_3PO_4+2CoA+4NAD^+ \rightarrow 2\text{acetyl-}CoA+2CO_2+2ATP+2H_2O+4NADH+4H^+ \quad \text{(Equation 1)}$$

The PPP provides a means to convert 1 mol glucose to 1 mol $CO_2$ and 2 mol NADPH, with the concomitant generation of 0.67 mol fructose-6-phosphat (F6P) and 0.33 mol glyceraldehyde-3-phosphate (GAP). The F6P and GAP thus formed must be metabolized by other reaction pathways, e.g. by the EMPP. The EDP converts 1 mol glucose to 1 mol GAP and 1 mol PYR with the concomitant generation of 1 mol NADPH. As with the PPP, the GAP thus formed must be metabolized by other reaction pathways. The PKP provides a means to convert 1 mol glucose to 1 mol GAP and 1.5 mol acetyl phosphate (AcP). When acetyl-CoA is desired, 1 equivalent of AcP plus 1 equivalent coenzyme A (CoA) can be converted to 1 equivalent acetyl-CoA and 1 equivalent inorganic phosphate (Pi) by the action of phosphotransacetylase.

For specific target molecules derived from AcCoA moieties generated through the PKP and near redox neutrality to the AcCoA moieties, there exists a deficiency in the overall energy balance. The PKP (and, similarly, the PPP and EDP) does not generate ATP for the conversion of glucose to glucose-6-phosphate. In the case of phosphoenolpyruvate (PEP)-dependent glucose uptake, PEP must be generated by other means, e.g. through the EMPP. Recycling GAP through the PKP exacerbates the issue, particularly when the product specific pathway provides little ATP. Sonderegger (loc. cit.) and U.S. Pat. No. 7,253,001 disclose recombinant *Saccharomyces cerevisiae* strains comprising native or overexpressed phosphoketolase activity together with overexpressed phosphotransacetylase to increase the yield in the conversion of glucose/xylose mixtures to ethanol. These strains feature PEP-independent glucose uptake with both the EMPP and the PPP operative.

Chinen (loc. cit.) and U.S. Pat. No. 7,785,858 disclose a recombinant bacterium selected from the group consisting of the Enterobacteriaceae family, Coryneform bacterium, and *Bacillus* bacterium comprising increased phosphoketolase activity for the conversion of glucose to target molecules which are produced via the intermediate acetyl-CoA, including the group consisting of L-glutamic acid, L-glutamine, L-proline, L-arginine, L-leucine, L-cysteine, succinate and polyhydroxybutyrate. These strains feature PEP-dependent glucose uptake with the EMPP operative. Notably, the activity of phosphofructokinase in the bacterium of U.S. Pat. No. 7,785,858 is reduced compared to that of a wild-type or non-modified strain (see page 33).

WO 2013/007786 describes a recombinant microorganism which has phosphoketolase activity and in which the EMPP is deactivated or diminished by abolishing or reducing phosphofructokinase and in which the oxidative branch of the PPP is deactivated or diminished by abolishing or reducing glucose-6-phosphate dehydrogenase. These measures lead to an increase in the amount of fructose-6-phosphate (F6P) which is converted by the phosphoketolase and fed into the non-oxidative branch of the PPP. In this case the glyceraldehyde-3-phosphate (G3P) which results from the non-oxidative branch of the PPP is recycled to fructose-1,6-bisphosphate (FBP) via the condensation with dihydroxyacetone phosphate (DHAP). This reaction is catalyzed by fructose-bisphosphate aldolase (EC 4.1.2.13). The fructose-1,6-bisphosphate (FBP) is then converted into fructose-6-phosphate (F6P) by the action of the enzyme fructose bisphosphatase (EC 3.1.3.11).

Fructose bisphosphatase (EC 3.1.3.11) is highly regulated (see, e.g., G. A. Tejwani, Advances in Enzymology and Related Areas of Molecular Biology 54:121-194 (1983)). In order to avoid futile cycles during glycolysis, fructose bisphosphatase activity is downregulated in the presence of glucose. Allosteric inhibition of *E. coli* Type I Fructose bisphosphatase (required for growth on neoglucogenic substrate) is mediated by Glucose-6-phosphate, the first metabolite produced upon glucose transport into the cell (and also part of sucrose import and metabolization pathways in *E. coli*) and AMP (J. Hines et al., J. Biol. Chem. 282:24697-24706 (2007)). This enzyme is basically inactive if glucose or sucrose is present in the culture medium.

Since in fermentation processes employing microorganisms glucose or sucrose are commonly used as carbon source and are also used in rather high concentrations, such fermentation conditions might hamper the efficiency of the conversion of dihydroxyacetone phosphate (DHAP) and glyceraldehyde-3-phosphate (G3P) into fructose-6-phosphate (F6P). Therefore, there is a need to develop a pathway which allows the conversion of dihydroxyacetone phosphate (DHAP) and glyceraldehyde-3-phosphate (G3P) into fructose-6-phosphate (F6P) even under conditions of high glucose or sucrose concentrations in the culture medium or in the reaction vessel.

The present invention meets this demand by providing a method for the production of fructose-6-phosphate (F6P) from dihydroxyacetone phosphate (DHAP) and glyceraldehyde-3-phosphate (G3P) comprising the steps of:
(a) enzymatically converting dihydroxyacetone phosphate (DHAP) into dihydroxyacetone (DHA); and
(b) enzymatically converting the thus produced dihydroxyacetone (DHA) together with glyceraldehyde-3-phosphate (G3P) into fructose-6-phosphate (F6P);
or comprising the steps of:
(a') enzymatically converting glyceraldehyde-3-phosphate (G3P) into glyceraldehyde; and
(b') enzymatically converting the thus produced glyceraldehyde together with dihydroxyacetone phosphate (DHAP) into fructose-1-phosphate (F1P); and
(c') and enzymatically converting the thus produced fructose-1-phosphate (F1P) into fructose-6-phosphate (F6P).

The conversion of dihydroxyacetone phosphate (DHAP) first into dihydroxyacetone (DHA) and its subsequent condensation with GAP in order to produce F6P provides an alternative route to the condensation of dihydroxyacetone phosphate (DHAP) and glyceraldehyde-3-phosphate (G3P) into fructose-1,6-bisphosphate (FBP) and its subsequent conversion into fructose-6-phosphate (F6P) with the advantage that it can be realized by making use of enzymes which are not regulated (in particular inhibited) by glucose or sucrose. Thus, this conversion can take place even at high concentrations of glucose or sucrose. The same holds true for the conversion of DHAP and G3P as described in steps (a') to (c').

The two alternative methods for producing fructose-6-phosphate (F6P) from dihydroxyacetone phosphate (DHAP) and glyceraldehyde-3-phosphate (G3P) as described above, can, of course, also be applied in combination (either in vitro or in vivo).

Thus, in a first aspect, the present invention relates to a method for the production of fructose-6-phosphate (F6P) from dihydroxyacetone phosphate (DHAP) and glyceraldehyde-3-phosphate (G3P) comprising the steps of:
(a) enzymatically converting dihydroxyacetone phosphate (DHAP) into dihydroxyacetone (DHA); and
(b) enzymatically converting the thus produced dihydroxyacetone (DHA) together with glyceraldehyde-3-phosphate (G3P) into fructose-6-phosphate (F6P).

The enzymatic conversion of dihydroxyacetone phosphate (DHAP) into dihydroxyacetone (DHA) according to step (a) of the method according to the present invention can, for example, be achieved by employing an enzyme classified as EC 3.1.3.-. These enzymes are also referred to as phosphoric monoester hydrolases (or phosphomonoesterases). Phosphoric monoester hydrolases are enzymes which catalyze the hydrolysis of O—P bonds by a nucleophilic attack of phosphorus by cysteine residues or coordinated metal ions.

In a preferred embodiment the enzyme classified as EC 3.1.3.- is selected from the group consisting of:
sugar phosphatase (EC 3.1.3.23);
6-phosphogluconate phosphatase (EC 3.1.3.-);
Pyridoxal phosphate phosphatase (EC 3.1.3.74);
Fructose-1-phosphate phosphatase (EC 3.1.3.-);
Dihydroxyacetone phosphatase (EC 3.1.3.-);
Hexitol phosphatase (EC 3.1.3.-)
acid phosphatase (EC 3.1.3.2);
alkaline phosphatase (EC 3.1.3.1);
glycerol-1-phosphate phosphatase (EC 3.1.3.21); and
3-phosphoglycerate phosphatase (EC 3.1.3.38).

Thus, in one embodiment the conversion of dihydroxyacetone phosphate (DHAP) into dihydroxyacetone (DHA) is achieved by making use of a sugar phosphatase (EC 3.1.3.23). Sugar phosphatases (EC 3.1.3.23) are enzymes which catalyze the following reaction:

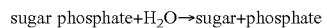

sugar phosphate+$H_2O$→sugar+phosphate

This enzyme occurs in a variety of organisms, including eukaryotic and prokaryotic organisms, such as plants, protozoans and bacteria. The enzyme has, e.g., been described in *Arabidopsis thaliana* (UniProt Accession number Q9ZVJ5), *Plasmodium falciparum* (UniProt Accession number Q8IJ74), *Streptococcus equinus, Streptococcus pyogenes, Saccharomyces cerevisia, Neisseria meningitidis, Lactococcus lactis, Klebsiella aerogenes, Escherichia coli* (UniProt Accession number P75792), *Escherichia acidilactici, Enterococcus faecalis* and *Bacillus subtilis*. In principle, any sugar phosphatase of EC 3.1.3.23 can be employed in the method according to the present invention as long as it has the capacity to convert dihydroxyacetone phosphate (DHAP) into dihydroxyacetone (DHA). In a preferred embodiment an enzyme from a bacterium of the genus *Escherichia* is used, more preferably an enzyme of the species *E. coli* is used. Even more preferably a YbiV protein or a YidA protein from *E. coli* is used (UniProt Accession numbers P75792 (SEQ ID NO: 1; encoded by the nucleotide sequence of SEQ ID NO:39) and P0A8Y5 (SEQ ID NO: 2; encoded by the nucleotide sequence of SEQ ID NO:41)).

In a preferred embodiment such an enzyme has an amino acid sequence as shown in SEQ ID NO: 1 or 2 or shows an amino acid sequence which is at least x % homologous to SEQ ID NO: 1 or 2 and has the activity of sugar phosphatase (EC 3.1.3.23) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 1 or 2.

As regards the determination of sequence identity as described in the present application, generally the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined by performing pairwise alignment using preferably algorithms and software well known in the art, such as Needleman-Wunsch algorithm with the EMBOSS NEEDLE software.

When applying this methodology to determine whether a particular sequence is, for instance, at least 60% identical to a reference sequence default settings of the EMBOSS NEEDLE software may be used, which are defined as follows:
Matrix: BLOSUM62
Gap open: 10
Gap extend: 0.5
No end gap penalty.
Preferably, the degree of identity is calculated over the complete length of the aligned sequence.

In another embodiment the conversion of dihydroxyacetone phosphate (DHAP) into dihydroxyacetone (DHA) is achieved by making use of 6-phosphogluconate phosphatase (EC 3.1.3.-). 6-phosphogluconate phosphatases are enzymes which catalyze the dephosphorylation of 6-phosphogluconate.

This enzyme has, e.g., been described for *Escherichia coli*. Thus, in a preferred embodiment the corresponding enzyme from *E. coli* is employed in the method according to the present invention, more preferably the YieH protein (UniProt Accession number P31467 (SEQ ID NO:3; encoded by the nucleotide sequence of SEQ ID NO:40)).

In a preferred embodiment such an enzyme has an amino acid sequence as shown in SEQ ID NO: 3 or shows an amino acid sequence which is at least x % homologous to SEQ ID NO: 3 and has the activity of a 6-phosphogluconate phosphatase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 3.

In another embodiment the conversion of dihydroxyacetone phosphate (DHAP) into dihydroxyacetone (DHA) is achieved by making use of a pyridoxal phosphate phosphatase (EC 3.1.3.74). Pyridoxal phosphate phosphatases are enzymes which catalyze the following reaction:

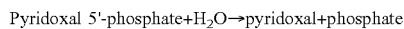

Pyridoxal 5'-phosphate+H$_2$O→pyridoxal+phosphate

This enzyme occurs in a variety of organisms, including eukaryotic and prokaryotic organisms, such as animals and bacteria. The enzyme has, e.g., been described in *Homo sapien, Rattus norvegicus, Brachylagus idahoensis, Bos taurus, Canis lupus, Felis catus, Gallus gallus, Meriones unguiculatus, Mus musculus, Paenibacillus thiaminolyticus, Sinorhizobium meliloti, Sus scorfa* and *Escherichia coli* (UniProt Accession number P27848). In principle, any pyridoxal phosphate phosphatase of EC 3.1.3.74 can be employed in the method according to the present invention as long as it has the capacity to convert dihydroxyacetone phosphate (DHAP) into dihydroxyacetone (DHA). In a preferred embodiment an enzyme from a bacterium of the genus *Escherichia* is used, more preferably an enzyme of the species *E. coli* is used. Even more preferably a YigL protein from *E. coli* is used (UniProt Accession number P27848 (SEQ ID NO:4; encoded by the nucleotide sequence of SEQ ID NO:42)).

In a preferred embodiment such an enzyme has an amino acid sequence as shown in SEQ ID NO: 4 or shows an amino acid sequence which is at least x % homologous to SEQ ID NO: 4 and has the activity of a pyridoxal phosphate phosphatase (EC 3.1.3.74) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 4.

In another embodiment the conversion of dihydroxyacetone phosphate (DHAP) into dihydroxyacetone (DHA) is achieved by making use of a fructose-1-phosphate phosphatase (EC 3.1.3.-). Fructose-1-phosphate phosphatases are enzymes which catalyze the dephosphorylation of fructose-1-phosphate.

This enzyme has, e.g., been described for *Escherichia coli*. Thus, in a preferred embodiment the corresponding enzyme from *E. coli* is employed in the method according to the present invention, more preferably the YqaB protein (UniProt Accession number P77475 (SEQ ID NO:5; encoded by the nucleotide sequence of SEQ ID NO:43)).

In a preferred embodiment such an enzyme has an amino acid sequence as shown in SEQ ID NO: 5 or shows an amino acid sequence which is at least x % homologous to SEQ ID NO: 5 and has the activity of a fructose-1-phosphate phosphatase (EC 3.1.3.-) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 5.

In another embodiment the conversion of dihydroxyacetone phosphate (DHAP) into dihydroxyacetone (DHA) is achieved by making use of a dihydroxyacetone phosphatase (EC 3.1.3.-). Dihydroxyacetone phosphatases are enzymes which catalyze the dephosphorylation of dihydroxyacetone phosphate (DHAP) to produce DHA.

This enzyme has, e.g., been described for *Corynebacterium glutamicum*. Thus, in a preferred embodiment the corresponding enzyme from *Corynebacterium glutamicum* is employed in the method according to the present invention, more preferably the HdpA protein (UniProt Accession number A4QFW4 (SEQ ID NO:6; encoded by the nucleotide sequence of SEQ ID NO:48)).

In a preferred embodiment such an enzyme has an amino acid sequence as shown in SEQ ID NO: 6 or shows an amino acid sequence which is at least x % homologous to SEQ ID NO: 6 and has the activity of a dihydroxyacetone phosphatase (EC 3.1.3.-) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 6.

In another embodiment the conversion of dihydroxyacetone phosphate (DHAP) into dihydroxyacetone (DHA) is achieved by making use of a hexitol phosphatase (EC 3.1.3.-). Hexitol phosphatases are enzymes which catalyze the dephosphorylation of D-mannitol 1-phosphate and D-sorbitol 6-phosphate.

This enzyme has, e.g., been described for *Escherichia coli*. Thus, in a preferred embodiment the corresponding enzyme from *E. coli* is employed in the method according to the present invention, more preferably the HxpA protein (UniProt Accession number P77625 (SEQ ID NO:7; encoded by the nucleotide sequence of SEQ ID NO:44)).

In a preferred embodiment such an enzyme has an amino acid sequence as shown in SEQ ID NO: 7 or shows an amino acid sequence which is at least x % homologous to SEQ ID NO: 7 and has the activity of a hexitol phosphatase (EC 3.1.3.-) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 7.

In another embodiment the conversion of dihydroxyacetone phosphate (DHAP) into dihydroxyacetone (DHA) is achieved by making use of an acid phosphatase (EC 3.1.3.2). Acid phosphatases are enzymes which catalyze the following reaction:

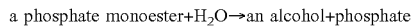

a phosphate monoester+$H_2O$→an alcohol+phosphate

This enzyme occurs in a large variety of organisms, including eukaryotic and prokaryotic organisms, such as animals, plants, fungi and bacteria. In principle any acid phosphatase (EC 3.1.3.2) can be employed in the method according to the present invention as long as it can convert dihydroxyacetone phosphate (DHAP) into dihydroxyacetone (DHA).

In another embodiment the conversion of dihydroxyacetone phosphate (DHAP) into dihydroxyacetone (DHA) is achieved by making use of an alkaline phosphatase (EC 3.1.3.1). Like acid phosphatases, alkaline phosphatases are enzymes which catalyze the following reaction:

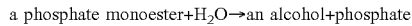

a phosphate monoester+$H_2O$→an alcohol+phosphate

This enzyme occurs in a large variety of organism, including eukaryotic and prokaryotic organisms, such as animals, plants, fungi and bacteria. In principle any alkaline phosphatase (EC 3.1.3.1) can be employed in the method according to the present invention as long as it can convert dihydroxyacetone phosphate (DHAP) into dihydroxyacetone (DHA).

In another embodiment the conversion of dihydroxyacetone phosphate (DHAP) into dihydroxyacetone (DHA) is achieved by making use of a glycerol-1-phosphate phosphatase (EC 3.1.3.21). Glycerol-1-phosphate phosphatases naturally catalyze the following reaction:

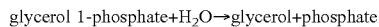

glycerol 1-phosphate+$H_2O$→glycerol+phosphate

This enzyme occurs in a large variety of organisms, including eukaryotic and prokaryotic organisms, such as animals, plants, fungi and bacteria. In principle any glycerol-1-phosphate phosphatase (EC 3.1.3.21) can be employed in the method according to the present invention as long as it can convert dihydroxyacetone phosphate (DHAP) into dihydroxyacetone (DHA).

In another embodiment the conversion of dihydroxyacetone phosphate (DHAP) into dihydroxyacetone (DHA) is achieved by making use of a 3-phosphoglycerate phosphatase (EC 3.1.3.38). 3-phosphoglycerate phosphatases naturally catalyze the following reaction:

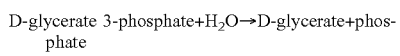

D-glycerate 3-phosphate+$H_2O$→D-glycerate+phosphate

This enzyme occurs in a large variety of organisms, including eukaryotic and prokaryotic organisms, such as plants, fungi and bacteria. In principle 3-phosphoglycerate phosphatase (EC 3.1.3.38) can be employed in the method according to the present invention as long as it can convert dihydroxyacetone phosphate (DHAP) into dihydroxyacetone (DHA).

As described above, the dihydroxyacetone (DHA) obtained in step (a) of the method according to the present invention can then be further converted together with glyceraldehyde-3-phosphate (G3P) into fructose-6-phosphate (F6P) as described in step (b) of the method. In the case of an in vitro reaction, the glyceraldehyde-3-phosphate (G3P) can simply be added to the reaction. In the case of an in vivo reaction, the glyceraldehyde-3-phosphate (G3P) is provided by other metabolic pathways. Since glyceraldehyde-3-phosphate (G3P) is an intermediate in glycolysis as well as the Entner-Douderoff-Pathway, it basically occurs in all organisms. Moreover, it is an isomer of dihydroxyacetone phosphate (DHAP) and can be produced from dihydroxyacetone phosphate (DHAP) by the action of a triose phosphate isomerase.

The conversion of dihydroxyacetone (DHA) and glyceraldehyde-3-phosphate (G3P) into fructose-6-phosphate (F6P) according to step (b) of the method according to the invention can, in one embodiment, be achieved by employing an enzyme referred to as aldehyde lyase (also sometimes referred to as carbon-carbon lyases). These enzymes are classified in EC 4.1.2.-. Such enzymes catalyze the cleavage of a C—C bond in a molecule having a carbonyl group and a hydroxyl group to form two molecules, each an aldehyde and a ketone. However, it has been found that these enzymes are also able to catalyze the condensation of glyceraldehyde-3-phosphate (G3P) and dihydroxyacetone (DHA) into fructose-6-phosphate (F6P).

In a preferred embodiment, an aldehyde lyase employed in a method according to the present invention for converting dihydroxyacetone (DHA) and glyceraldehyde-3-phosphate (G3P) into fructose-6-phosphate (F6P) is a fructose-6-phosphate aldolase, e.g a fructose-6-phosphate aldolase 1. An example and preferred embodiment is the fructose-6-phosphate aldolase 1 from *E. coli* which is encoded from the gene fsaA. The amino acid sequence of this protein is available, e.g., under UniProt accession number P78055 (SEQ ID NO:8; encoded by the nucleotide sequence of SEQ ID NO:34).

In another preferred embodiment, the aldehyde lyase employed in the method according to the present invention for converting dihydroxyacetone (DHA) and glyceraldehyde-3-phosphate (G3P) into fructose-6-phosphate (F6P) is a fructose-6-phosphate aldolase 2. An example and preferred embodiment is the fructose-6-phosphate aldolase 2 from *E. coli* which is encoded from the gene fsaB. The amino acid sequence of this protein is available, e.g., under UniProt accession number P32669 (SEQ ID NO:16; encoded by the nucleotide sequence of SEQ ID NO:36).

In a preferred embodiment such an enzyme has an amino acid sequence as shown in SEQ ID NO: 8, 9 or 16 or shows an amino acid sequence which is at least x % homologous to SEQ ID NO: 8, 9 or 16 and has the activity of a fructose-6-phosphate aldolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone (DHA) and glyceraldehyde-3-phosphate (G3P) into fructose-6-phosphate (F6P) as set forth herein above. Preferably, the degree of identity is determined by comparing the respective sequence with the amino acid sequence of SEQ ID NO: 8, 9 or 16. The amino acid sequence of SEQ ID NO: 9 (encoded by the nucleotide sequence of SEQ ID NO:35) is a mutated form of the sequence of SEQ ID NO: 8 with a higher enzymatic activity.

In another embodiment, the conversion of dihydroxyacetone (DHA) and glyceraldehyde-3-phosphate (G3P) into fructose-6-phosphate (F6P) according to step (b) of the method according to the invention can be achieved by employing an enzyme referred to as a transaldolase. These enzymes are classified in EC 2.2.1.2. Such enzymes catalyze the following reaction:

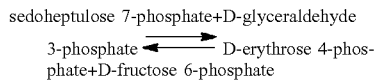

sedoheptulose 7-phosphate+D-glyceraldehyde 3-phosphate ⇌ D-erythrose 4-phosphate+D-fructose 6-phosphate This enzyme occurs in a variety of organism, including eukaryotic and prokaryotic organisms, such as plants, algae, animals, fungi and bacteria. The enzyme has, e.g., been described in *Acidithiobacillus ferrooxidans, Arthrobacter* sp., *Bifidobacterium bifidum, Blastobotrys adeninivorans, Bos taurus, Carcinus maenas, Chlorella* sp., *Chlorobium vibriforme* f. *thiosulfatophilum, Chromatium* sp., *Clostridium acetobutylicum, Cryptococcus neoformans, Cyberlindnera jadinii, Escherichia coli, Euglena* sp., *Francisella tularensis* (UniProt Accession number Q5NFX0), *Fusarium oxysporum, Gluconobacter oxydans* (UniProt Accession number Q76EM7), *Homo sapiens, Methanocaldococcus jannaschii, Moniiella megachiliensis, Mus musculus, Musca domestica, Oryctolagus cuniculus, Rattus norvegicus, Saccharomyces carlsbergensis, Saccharomyces cerevisiae, Scheffersomyces stipitis, Solanum lycopersicum, Spinacia olearacea, Tetranychus telarius, Thermoplasma acidophilum, Thermotoga maritima,* (UniProt Accession number Q9WYD1), *Streptococcus pyogenes* (UniProt Accession number Q99XT4; SEQ ID NO: 12 (encoded by the nucleotide sequence of SEQ ID NO:50)), *Clostridium beijerinckii* (UniProt Accession number A0A0B5QQ90; SEQ ID NO: 13 (encoded by the nucleotide sequence of SEQ ID NO:53)), *Caulobacter vibrioides* (UniProt accession number Q9A2F1; SEQ ID NO: 14 (encoded by the nucleotide sequence of SEQ ID NO:54)), *Streptococcus mutans* (UniProt accession number Q8DVJ4; SEQ ID NO: 15 (encoded by the nucleotide sequence of SEQ ID NO:56)), *E. coli* (UniProt accession number P0A870; SEQ ID NO: 17 (encoded by the nucleotide sequence of SEQ ID NO:37)), *Enterococcus faecalis* (UniProt accession number A0A0M2AGL1; SEQ ID NO: 18 (encoded by the nucleotide sequence of SEQ ID NO:52)), *Streptococcus suis* (UniProt accession number A0A0E4C393; SEQ ID NO: 19 (encoded by the nucleotide sequence of SEQ ID NO:55)), *Streptococcus pneumoniae* (UniProt accession number A0A0D6J3Z8; SEQ ID NO: 20 (encoded by the nucleotide sequence of SEQ ID NO:58)), *Streptococcus gordonii* (UniProt Accession number A8AZ46; SEQ ID NO: 10 (encoded by the nucleotide sequence of SEQ ID NO:51)), *Streptococcus agalactiae* (UniProt Accession number Q8E738; SEQ ID NO: 31 (encoded by the nucleotide sequence of SEQ ID NO:57)) and *Listeria monocytogenes* (UniProt Accession number A0A0H3GHX1; SEQ ID NO: 11 (encoded by the nucleotide sequence of SEQ ID NO:49)).

In principle, any transaldolase of EC 2.2.1.2 can be employed in the method according to the present invention as long as it has the capacity to convert dihydroxyacetone (DHA) and glyceraldehyde-3-phosphate (G3P) into fructose-6-phosphate (F6P). In a preferred embodiment an enzyme from a bacterium of the genus *Streptococcus* or of the genus *Listeria* is used, more preferably an enzyme of the species *Streptococcus gordonii* or of the species *Listeria monocytogenes* is used. In a preferred embodiment a protein from *Streptococcus gordonii* encoded by the SGO_1787 gene of *Streptococcus gordonii* (UniProt Accession number A8AZ46) is used.

In a preferred embodiment such an enzyme has an amino acid sequence as shown in any one of SEQ ID NOs: 10 to 15, SEQ ID NOs: 17 to 20, SEQ ID NO:64, and SEQ ID NO:31 or shows an amino acid sequence which is at least x % homologous to any one of SEQ ID NOs: 10 to 20, SEQ ID NO: 64 and SEQ ID NO:31 and has the activity of a transaldolase (EC 2.2.1.2) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone (DHA) and glyceraldehyde-3-phosphate (G3P) into fructose-6-phosphate (F6P) as set forth herein above. The enzyme from *Streptococcus suis* (UniProt accession number A0A0E4C393; SEQ ID NO: 19 (encoded by the nucleotide sequence of SEQ ID NO:55)) is particularly preferred.

The amino acid sequence of SEQ ID NO: 64 (encoded by the nucleotide sequence of SEQ ID NO:38) is a mutated form of the sequence of SEQ ID NO: 17 with a higher enzymatic activity (talB F178Y).

Preferably, the degree of identity is determined by comparing the respective sequence with the amino acid sequence of SEQ ID NO: 10 or 11.

In another aspect, the present invention relates to a method for the production of fructose-6-phosphate (F6P) from dihydroxyacetone phosphate (DHAP) and glyceraldehyde-3-phosphate (G3P) comprising the steps of:

(a') enzymatically converting glyceraldehyde-3-phosphate (G3P) into glyceraldehyde; and (b') enzymatically converting the thus produced glyceraldehyde together with dihydroxyacetone phosphate (DHAP) into fructose-1-phosphate (F1P); and (c') enzymatically converting the thus produced fructose-1-phosphate (F1P) into fructose-6-phosphate (F6P).

The enzymatic conversion of glyceraldehyde-3-phosphate (G3P) into glyceraldehyde according to step (a') of the method according to the present invention is a dephosphorylation reaction according to the following scheme:

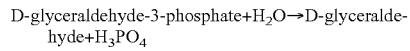

D-glyceraldehyde-3-phosphate+$H_2O$→D-glyceraldehyde+$H_3PO_4$

This hydrolytic cleavage of the phosphate group is an irreversible reaction. It can, for example, be achieved by employing an enzyme classified as EC 3.1.3.-. These enzymes are also referred to as phosphoric monoester hydrolases (or phosphomonoesterases). Phosphoric monoester hydrolases are enzymes which catalyze the hydrolysis of O—P bonds by a nucleophilic attack of phosphorus by cysteine residues or coordinated metal ions.

In a preferred embodiment the enzyme classified as EC 3.1.3.- is selected from the group consisting of:
- glyceraldehyde 3-phosphate phosphatase (EC 3.1.3.-);
- alkaline phosphatase (EC 3.1.3.1);
- acid phosphatase (EC 3.1.3.2);
- sugar phosphatase (EC 3.1.2.23); and
- hexitol phosphatase (EC 3.1.3.-)

Thus, in one embodiment the conversion of glyceraldehyde-3-phosphate (G3P) into glyceraldehyde is achieved by making use of a glyceraldehyde 3-phosphate phosphatase (EC 3.1.3.-). These enzymes catalyze the dephosphorylation of glyceraldehyde-3-phosphate.

This activity has, e.g. been described for the protein encoded by the PH1655 gene of *Pyrococcus horikoshii* or for the protein encoded by the MJ1437 gene of *Methanocaldococcus jannaschii*. Thus, in a preferred embodiment, a corresponding protein from *Pyrococcus horikoshii* (UniProt accession number O59346 (SEQ ID NO:21; encoded by the nucleotide sequence of SEQ ID NO:59)) or from *Methanocaldococcus jannaschii* (UniProt accession number Q58832 (SEQ ID NO:22; encoded by the nucleotide sequence of SEQ ID NO:60)) is used.

In a preferred embodiment such an enzyme has an amino acid sequence as shown in SEQ ID NO: 21 or as shown in SEQ ID NO: 22 or shows an amino acid sequence which is at least x % homologous to SEQ ID NO: 21 or SEQ ID NO: 22 and has the activity of a glyceraldehyde 3-phosphate phosphatase (EC 3.1.3.-) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting glyceraldehyde-3-phosphate (G3P) into glyceraldehyde as set forth herein above.

In another embodiment, the conversion of glyceraldehyde-3-phosphate (G3P) into glyceraldehyde is achieved by making use of an alkaline phosphatase (EC 3.1.3.1). Alkaline phosphatases are enzymes which catalyze the following reaction:

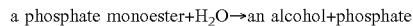

a phosphate monoester+H$_2$O→an alcohol+phosphate

This enzyme occurs in a large variety of organisms, including eukaryotic and prokaryotic organisms, such as animals, plants, fungi and bacteria. In principle any alkaline phosphatase (EC 3.1.3.1) can be employed in the method according to the present invention as long as it can convert glyceraldehyde-3-phosphate (G3P) into glyceraldehyde.

In another embodiment, the conversion of glyceraldehyde-3-phosphate (G3P) into glyceraldehyde is achieved by making use of an acid phosphatase (EC 3.1.3.2). Like alkaline phosphatases, acid phosphatases are enzymes which catalyze the following reaction:

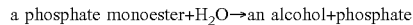

a phosphate monoester+H$_2$O→an alcohol+phosphate

This enzyme occurs in a large variety of organisms, including eukaryotic and prokaryotic organisms, such as animals, plants, fungi and bacteria. In principle any acid phosphatase (EC 3.1.3.2) can be employed in the method according to the present invention as long as it can convert glyceraldehyde-3-phosphate (G3P) into glyceraldehyde.

In a further preferred embodiment the conversion of glyceraldehyde-3-phosphate (G3P) into glyceraldehyde is achieved by making use of a sugar phosphatase (EC 3.1.3.23). Sugar phosphatases (EC 3.1.3.23) are enzymes which catalyze the following reaction:

sugar phosphate+H$_2$O→sugar+phosphate

This enzyme occurs in a variety of organisms, including eukaryotic and prokaryotic organisms, such as plants, protozoans and bacteria. The enzyme has, e.g., been described in *Arabidopsis thaliana* (UniProt Accession number Q9ZVJ5), *Plasmodium falciparum* (UniProt Accession number Q8IJ74), *Streptococcus equinus*, *Streptococcus pyogenes*, *Saccharomyces cerevisia*, *Neisseria meningitidis*, *Lactococcus lactis*, *Klebsiella aerogenes*, *Escherichia coli* (UniProt Accession number P75792 (SEQ ID NO:1; encoded by the nucleotide sequence of SEQ ID NO:39)), *Escherichia acidilactici*, *Enterococcus faecalis* and *Bacillus subtilis*.

In principle, any sugar phosphatase of EC 3.1.3.23 can be employed in the method according to the present invention as long as it has the capacity to convert glyceraldehyde-3-phosphate (G3P) into glyceraldehyde. In a preferred embodiment an enzyme from a bacterium of the genus *Escherichia* is used, more preferably an enzyme of the species *E. coli* is used. Even more preferably a YbiV protein from *E. coli* is used (UniProt Accession number P75792 (SEQ ID NO:1; encoded by the nucleotide sequence of SEQ ID NO:39)).

In a preferred embodiment such an enzyme has an amino acid sequence as shown in SEQ ID NO: 1 or shows an amino acid sequence which is at least x % homologous to SEQ ID NO: 1 and has the activity of sugar phosphatase (EC 3.1.3.23) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting dihydroxyacetone phosphate (DHAP) into dihydroxyacetone (DHA) as set forth herein above.

Preferably, the degree of identity is determined by comparing the respective sequence with the amino acid sequence of SEQ ID NO: 1.

In another embodiment the conversion of glyceraldehyde-3-phosphate (G3P) into glyceraldehyde is achieved by making use of a hexitol phosphatase (EC 3.1.3.-). Hexitol phosphatases are enzymes which catalyze the dephosphorylation of D-mannitol 1-phosphate and D-sorbitol 6-phosphate.

This enzyme has, e.g., been described for *Escherichia coli*. Thus, in a preferred embodiment the corresponding enzyme from *E. coli* is employed in the method according to the present invention, more preferably the HxpB protein (UniProt Accession number P77247 (SEQ ID NO:23; encoded by the nucleotide sequence of SEQ ID NO:45)). In a preferred embodiment such an enzyme has an amino acid sequence as shown in SEQ ID NO: 23 or shows an amino acid sequence which is at least x % homologous to SEQ ID NO: 23 and has the activity of a hexitol phosphatase (EC 3.1.3.-) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting glyceraldehyde-3-phosphate (G3P) into glyceraldehyde as set forth herein above.

Preferably, the degree of identity is determined by comparing the respective sequence with the amino acid sequence of SEQ ID NO: 23.

As described above, the glyceraldehyde obtained in step (a') of the method according to the present invention can then be further converted together with dihydroxyacetone phosphate (DHAP) into fructose-6-phosphate (F1P) as described in step (b') of the method. In the case of an in vitro reaction, the dihydroxyacetone phosphate (DHAP) can simply be added to the reaction. In the case of an in vivo reaction, the dihydroxyacetone phosphate (DHAP) is provided by other metabolic pathways. Since dihydroxyacetone phosphate (DHAP) is an intermediate in glycolysis as well as the Entner-Douderoff-Pathway, it basically occurs in all organisms. Moreover, it is an isomer of glyceraldehyde-3-phosphate (G3P) and can be produced from glyceraldehyde-3-phosphate (G3P) by the action of a triose phosphate isomerase.

The conversion of dihydroxyacetone phosphate (DHAP) and glyceraldehyde into fructose-1-phosphate (F1P) according to step (b') of the method according to the invention is an aldol condensation and proceeds according to the following reaction:

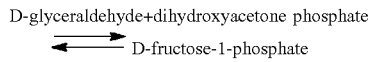
D-glyceraldehyde+dihydroxyacetone phosphate ⇌ D-fructose-1-phosphate

This conversion can, e.g., be achieved by making use of a fructose bisphosphate aldolase (EC 4.1.2.13).

Fructose-bisphosphate aldolases (EC 4.1.2.13) are enzymes which can catalyze the following reaction:

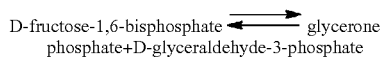
D-fructose-1,6-bisphosphate ⇌ glycerone phosphate+D-glyceraldehyde-3-phosphate The enzyme has been identified in a variety of organisms and fructose-1,6-bisphosphate aldolases are divided into two classes, which rely on different reaction mechanisms. Class I fructose-1,6-bisphosphate aldolases are mainly found in animals and higher plants, while Class II fructose-1,6-bisphosphate aldolases are found mainly in algae, bacteria and yeasts. The enzymes belonging to Class II require a bivalent metal ion as a cofactor.

Both type I and type II fructose-1,6-bisphosphate aldolases have been isolated from different prokaryotic and eukaryotic sources and thus, fructose-1,6-bisphosphate aldolase is an ubiquitous glycolytic enzyme that plays a crucial role in glycolysis, gluconeogenesis, and fructose metabolism (Brovetto M. et al. Chem. Rev. 111 (2011), 4346-4403).

Thus, in a preferred embodiment, the fructose-1,6-bisphosphate aldolase (EC 4.1.2.13) originates from a prokaryotic organism, preferably a bacterium. The enzyme has, e.g., been described to occur in *Peptoniphilus asaccharolyticus, Escherichia coli, Thermus aquaticus, Mycobacterium tuberculosis, Aspergillus oryzae, Bacillus cereus, Bacillus subtilis, Clostridium* sp., *Corynebacterium* sp., *Heliobacter pylori, Lactobacillus* sp., *Mycobacterium* sp., *Penicillinum* sp., *Pseudomonas* sp., *Plasmodium falciparum, Saccharomyces* sp. and *Methylococcus cuniculus*.

Moreover, in a preferred embodiment, the fructose 1,6-bisphosphate aldolase (EC 4.1.2.13) originates from a eukaryotic organism. The enzyme has, e.g., been described to occur in *Homo sapiens, Drosophila melanogaster, Oryctolagus cuniculus, Gallus gallus, Zea mays, Bos taurus, Mus musculus,* and *Medicago sativa*.

The study of Siebers et al. firstly revealed that no genes encoding classical Class I and Class II enzymes have been identified in any of the sequenced archaea genomes (Siebers B. et al., J Bol. Chem. 276 (2001), 28710-28718). Later biochemical and structural characterization of aldolases from the two hyperthermophilic archaea, *Thermoproteus tenax* and *Pyrococcus furiosus*, showed that these enzymes use a Schiff-base mechanism and thus belong to the class I aldolases (Siebers et al., loc. cit.; Lorentzen E. et al., Biochem. Soc. Trans. 32 (2004), 259-263).

Class I fructose-1,6-bisphosphate aldolases can be classified into three isoenzyme forms, distinguishable on the basis of immunological reactivity as well as turnover with respect to fructose-1,6-biphosphate and fructose 1-phosphate substrates (Blonski et al., Biochem. J. 323 (1997), 71-77). Isoenzyme A, from rabbit muscle, has been the most extensively studied of the class I fructose-1,6-bisphosphate aldolases (Gefflaut et al., Prog. Biophys. Mol. Biol. 63 (1995), 301-340). Several dozen different isoenzymes have been sequenced and several aldolase isoenzyme structures have been determined, including those from rabbit muscle (Sygusch et al., Proc. Natl. Acad. Sci. 84 (1987), 7846-7850), human muscle (Gamblin et al., FEBS Lett. 262 (1987), 282-286, Arakaki et al., Protein Sci. 13 (2004), 3077-3084) and *Drosophila* (Hester et al., FEBS Lett. 292 (1991), 237-242). With the exception of the 20 amino acid residues comprising the C-terminal region, the molecular architecture of these isoenzymes has been highly conserved. The polypeptide fold of each enzyme subunit of the homotetramer corresponds to that of a β-barrel, with the active site located in the centre of the β-barrel (Sygusch et al., Proc. Natl. Acad. Sci. 84 (1987), 7846-7850). Unlike other β-barrel isoenzymes, the active site is composed of a substantial number of charged amino acid residues, i.e. Asp-33, Lys-107, Lys-146, Glu-187 and Lys-229 (Blonski et al., Biochem. J. 323 (1997), 71-77).

The class II FBP-aldolases require a divalent cation, usually $Zn^{2+}$ and are activated by monovalent cations (Horecker et al., In The Enzymes (Boyer, P. D., ed.), 1972, 3rd edit., vol. 7, 213-258, Academic Press, New York). They share around 15% sequence identity with the class I enzymes (Naismith et al., J. Mol. Biol. 225 (1992), 1137-1141). In a preferred embodiment, the fructose-1,6-bisphosphate aldolase employed in the method of the invention is provided in the presence of a divalent cation, preferably $Zn^{2+}$ and is activatey by monovalent cations.

Class II FBP enzymes can be further categorized into class IIA and class IIB families. Traditionally, class IIA and class IIB FBP enzymes were categorized according to sequence homology and their oligomeric state. Class IIA FBP enzymes were considered dimers, while class IIB FBAs could be dimers, tetramers or octamers. (Izard and Sygush, J. Biol. Chem 279 (2004), 11825-11833; Galkin et al., Biochemistry 48 (2009), 3186-3196; Nakahara et al., Plant Cell Physiol. 44 (2003), 326-333). Alignment of sequences of FBP-proteins showed that members belonging to each family exhibit 40% sequence similarity and amino-acid sequence identity between the type A and B class II FBP aldolases is of the order of 25-30% (Plaumann et al., Curr. Genet. 31 (1997), 430-438). Subsequent sequence alignments of the eight known Class II FBP aldolases showed that Arg-331 is one of the highly conserved residues. Chemical modification and site-directed mutagenesis have confirmed the critical role of this amino acid in the active site (Qamar et al., Protein Sci. 5 (1996), 154-161).

The crystal structure has been determined for several enzymes, i.e. from *E. coli* (Hall et al., J. Mol. Biol. 287 (1999), 383-394), *Thermus aquaticus* (Izard and Sygush; loc. cit.), *Thermus caldophilus* (Lee et al., Biochem. Biophys. Res. Commun. 347 (2006), 616-625), *Giardia lamblia* (Galkin et al.; loc. cit.), *Mycobacterium tuberculosis* (Pegan et al., J. Mol. Biol. 386 (2009), 1038-1053). The secondary structure of *Mycobacterium tuberculosis* FBP aldolase resembles that of the other bacterial class II aldolases (Pegan et al., loc. cit.). The enzyme has an eight-stranded β-sheet core in which each β-strand (β1-β8) is followed in general by an α-helix (α1-α8a), giving rise to an overall (β/α)8-barrel fold, also known as the TIM barrel fold (reference in InterPro database is IPR013785).

In principle, any fructose 1,6-bisphosphate aldolase (EC 4.1.2.13) can be employed in the conversion of D-erythrose into glycolaldehyde according to a method of the invention.

In a preferred embodiment, the fructose-1,6-bisphosphate aldolase (EC 4.1.2.13) employed in a method according to the present invention is the fructose-1,6-bisphosphate aldolase from *Escherichia coli* (strain K12) (i.e., a class II fructose-bisphosphate aldolase) (Uniprot P0AB71) showing the amino acid sequence as depicted in SEQ ID NO: 24 (encoded by the nucleotide sequence of SEQ ID NO:46 of the gene fbaA) or the fructose-1,6-bisphosphate aldolase from *Escherichia coli* (strain K12) (i.e., a class I fructose-bisphosphate aldolase) (Uniprot P0A991) showing the amino acid sequence as depicted in SEQ ID NO: 25 (encoded by the nucleotide sequence of SEQ ID NO:47 of the gene fbaB) or the fructose-1,6-bisphosphate aldolase B from *Homo sapiens* (Uniprot P05062) showing the amino acid sequence as depicted in SEQ ID NO: 26 (encoded by the nucleotide sequence of SEQ ID NO:61 of the gene ALDOB) or the fructose-1,6-bisphosphate aldolase A from *Homo sapiens* (Uniprot P04075) showing the amino acid sequence as depicted in SEQ ID NO: 27 or the fructose-1,6-bisphosphate aldolase C from *Homo sapiens* (Uniprot P09972) showing the amino acid sequence as depicted in SEQ ID NO: 28.

Thus, in a preferred embodiment, the fructose-1,6-bisphosphate aldolase (EC 4.1.2.13) employed in the method of the invention has the amino acid sequence as shown in any one of SEQ ID NOs: 24 to 28 or shows an amino acid sequence which is at least x % homologous to any one of SEQ ID NOs: 24 to 28 and has the activity of a fructose-1,6-bisphosphate aldolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting D-erythrose into glycolaldehyde as set forth herein above. Preferably, the degree of identity is determined as described above.

The enzymatic activity of a fructose-1,6-bisphosphate aldolase (EC 4.1.2.13) can be assessed with methods known to the person skilled in the art. Such methods are, e.g., described in Blonski K. et al., Biochem. J. 323 (1997), 71-77 and Szwergold et al., Arch. Biochem. Biophys. 317 (1995), 244-252.

As described above, the fructose-1-phosphate (F1P) obtained in step (b') of the method according to the present invention can then enzymatically be further converted into fructose-6-phosphate (F6P) (see step (c'). This conversion is an isomerization and proceeds according to the following reaction:

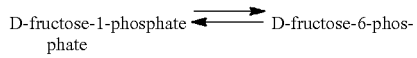

D-fructose-1-phosphate ⇌ D-fructose-6-phosphate

The conversion can be achieved by employing, for example, a phosphoglucomutase (EC 5.4.2.2), a phosphomannomutase (EC 5.4.2.8) or a beta-phosphoglucomutase (EC 5.4.2.6).

Thus, in one embodiment the conversion of fructose-1-phosphate (F1P) into fructose-6-phosphate (F6P) according to step (c') of the method according to the invention is achieved by making use of a phosphoglucomutase (EC 5.4.2.2). Phosphoglucomutases are enzymes which naturally catalyze the following reaction:

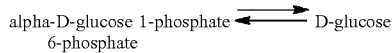

alpha-D-glucose 1-phosphate ⇌ D-glucose 6-phosphate

This enzyme occurs in a large variety of organisms, including eukaryotic and prokaryotic organisms, such as animals, plants, fungi and bacteria. In principle any phosphoglucomutase (EC 5.4.2.2) can be employed in the method according to the present invention as long as it can convert fructose-1-phosphate (F1P) into fructose-6-phosphate (F6P). In a preferred embodiment, the enzyme is an enzyme encoded by the pgm gene of *Aeromonas hydrophila*, preferably *Aeromonas hydrophila* subsp. *hydrophila*, such as the protein having the amino acid sequence as shown in UniProt accession number A0KIH4 (SEQ ID NO:29; encoded by the nucleotide sequence of SEQ ID NO:62 of the gene pgm).

In a preferred embodiment such an enzyme has an amino acid sequence as shown in SEQ ID NO: 29 or shows an amino acid sequence which is at least x % homologous to SEQ ID NO: 29 and has the activity of a phosphoglucomutase (EC 5.4.2.2) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting fructose-1-phosphate (F1P) into fructose-6-phosphate (F6P) as set forth herein above.

Preferably, the degree of identity is determined by comparing the respective sequence with the amino acid sequence of SEQ ID NO: 29.

In another embodiment the conversion of fructose-1-phosphate (F1P) into fructose-6-phosphate (F6P) according to step (c') of the method according to the invention is achieved by making use of a phosphomannomutase (also referred to as phosphoglucomutase) (EC 5.4.2.8). Phosphomannomutases (EC 5.4.2.8) have been reported to naturally catalyze the following reactions:

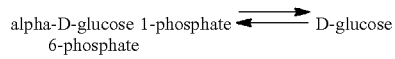

alpha-D-glucose 1-phosphate ⇌ D-glucose 6-phosphate and

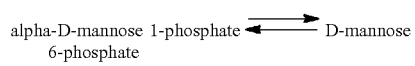

alpha-D-mannose 1-phosphate ⇌ D-mannose 6-phosphate

This enzyme occurs in a large variety of organisms, including eukaryotic and prokaryotic organisms, such as animals, plants, fungi and bacteria. In principle any phosphomannomutase (EC 5.4.2.8) can be employed in the method according to the present invention as long as it can convert fructose-1-phosphate (F1P) into fructose-6-phosphate (F6P). In a preferred embodiment, the enzyme is an enzyme encoded by the AHA_2903 gene of *Aeromonas hydrophila*, preferably *Aeromonas hydrophila* subsp. *hydrophila*, such as the protein having the amino acid sequence as shown in UniProt accession number A0KMA6 (SEQ ID NO:30; encoded by the nucleotide sequence of SEQ ID NO:63 of the gene AHA 2903).

In a preferred embodiment such an enzyme has an amino acid sequence as shown in SEQ ID NO: 30 or shows an amino acid sequence which is at least x % homologous to SEQ ID NO: 30 and has the activity of a phosphomannomutase (EC 5.4.2.8) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting fructose-1-phosphate (F1P) into fructose-6-phosphate (F6P) as set forth herein above.

Preferably, the degree of identity is determined by comparing the respective sequence with the amino acid sequence of SEQ ID NO: 30.

In another embodiment the conversion of fructose-1-phosphate (F1P) into fructose-6-phosphate (F6P) according to step (c') of the method according to the invention is achieved by making use of a beta-phosphoglucomutase (also referred to as phosophomannomutase) (EC 5.4.2.6). Beta-phosphoglucomutases (EC 5.4.2.6) have been reported to naturally catalyze the following reaction:

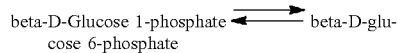

beta-D-Glucose 1-phosphate ⇌ beta-D-glucose 6-phosphate

This enzyme occurs in a large variety of organisms, including prokaryotic organisms, such as bacteria. In principle any beta-phosphoglucomutase (EC 5.4.2.6) can be employed in the method according to the present invention as long as it can convert fructose-1-phosphate (F1P) into fructose-6-phosphate (F6P). In a preferred embodiment, the enzyme is an enzyme encoded by the pgm gene of *Escherichia coli* (strain K12), such as the protein having the amino acid sequence as shown in UniProt accession number P36938 (SEQ ID NO:32 encoded by the gene termed pgm) or an enzyme encoded by the ycjU gene of *Escherichia coli* (strain K12), such as the protein having the amino acid sequence as shown in UniProt accession number P77366 (SEQ ID NO:33 encoded by the gene termed YcjU).

In a preferred embodiment such an enzyme has an amino acid sequence as shown in SEQ ID NO: 32 or SEQ ID NO:33 or shows an amino acid sequence which is at least x % homologous to SEQ ID NO: 32 or SEQ ID NO:33 and has the activity of a beta-phosphoglucomutase (EC 5.4.2.6) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting fructose-1-phosphate (F1P) into fructose-6-phosphate (F6P) as set forth herein above.

Preferably, the degree of identity is determined by comparing the respective sequence with the amino acid sequence of SEQ ID NO: 32 or SEQ ID NO:33.

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing the enzymes described above for the conversions of the method according to the present invention as described herein above. A method which employs a microorganism for carrying out a method according to the invention is referred to as an "in vivo" method. It is possible to use a microorganism which naturally produces the enzymes described above for the conversions of the method according to the present invention or a microorganism which had been genetically modified so that it expresses (including overexpresses) one or more of such enzymes. Thus, the microorganism can be an engineered microorganism which expresses enzymes described above for the conversions of the method according to the present invention, i.e. which has in its genome a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express enzymes described above for the conversions of the method according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme. Thus, the enzymes and (micro)organisms employed in connection with the present invention are preferably non-naturally occurring enzymes or (microorganisms), i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have the respective enzyme activity but which is genetically modified so as to comprise a nucleotide sequence allowing the expression of a corresponding enzyme. Similarly, the microorganism may also be a microorganism which naturally has the respective enzyme activity but which is genetically modified so as to enhance such an activity, e.g. by the introduction of an exogenous nucleotide sequence encoding a corresponding enzyme or by the introduction of a promoter for the endogenous gene encoding the enzyme to increase endogenous production to overexpressed (non-natural) levels.

If a microorganism is used which naturally expresses a corresponding enzyme, it is possible to modify such a microorganism so that the respective activity is overexpressed in the microorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above. The genetic modification of microorganisms to express an enzyme of interest will also be further described in detail below.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

As described above, the method according to the present invention can particularly be useful and advantageous when implemented in a microorganism as described in WO 2013/007786. This document describes a recombinant microorganism which has phosphoketolase activity and in which the EMPP is deactivated or diminished by abolishing or reducing phosphofructokinase and in which the oxidative branch of the PPP is deactivated or diminished by abolishing or reducing glucose-6-phosphate dehydrogenase. These measures lead to an increase in the amount of fructose-6-phosphate (F6P) which is converted by the phosphoketolase and fed into the non-oxidative branch of the PPP. In this case the glyceraldehyde-3-phosphate (G3P) which results from the non-oxidative branch of the PPP is recycled to fructose-1,6-bisphosphate (FBP) via the condensation with dihydroxyacetone phosphate (DHAP). This reaction is catalyzed by fructose-bisphosphate aldolase (EC 4.1.2.13). The fructose-1,6-bisphosphate (FBP) is then converted into fructose-6-phosphate (F6P) by the action of the enzyme fructose bisphosphatase (EC 3.1.3.11). The method according to the present invention circumvents the regulation of fructose-bisphosphate aldolase (EC 4.1.2.13) and fructose bisphosphatase (EC 3.1.3.11) and their inhibition at higher levels of glucose or sucrose in the fermentation medium. Thus, the method according to the present invention allows the conversion of dihydroxyacetone phosphate (DHAP) and glyceraldehyde-3-phosphate (G3P) into fructose-6-phosphate (F6P) in such a microorganism even under conditions of high glucose or sucrose concentrations in the culture medium or in the reaction vessel. Thus, in a preferred embodiment the above described method for the production of fructose-6-phosphate according to the invention is implemented in a microorganism as described in WO 2013/007786.

Accordingly, in a preferred embodiment, the method according to the present invention is implemented in a microorganism which is not only characterized in recombinantly expressing the enzymes described above in connection with the method but which is furthermore characterized in that it:
a) has phosphoketolase activity;
b) (i) has a diminished or inactivated Embden-Meyerhof-Parnas pathway (EMPP) by inactivation of the gene(s) encoding phosphofructokinase or by reducing phosphofructokinase activity as compared to a non-modified microorganism; or
   (ii) does not possess phosphofructokinase activity;
and
c) (i) has a diminished or inactivated oxidative branch of the pentose phosphate pathway (PPP) by inactivation of the gene(s) encoding glucose-6-phosphate dehydrogenase or by reducing glucose-6-phosphate dehydrogenase activity as compared to a non-modified microorganism; or
   (ii) does not possess glucose-6-phosphate dehydrogenase activity.

Such a microorganism is characterised by having phosphoketolase activity, so as to increase the flux of acetyl-CoA produced. Usually, a microorganism converts glucose via the Embden-Meyerhof-Parnas pathway into pyruvate which can then be converted into acetyl-CoA by the enzyme pyruvate dehydrogenase. However, this conversion is accompanied by the release of $CO_2$ and, thus, one carbon atom is lost which might have been used in the production of useful metabolites. In order to increase the amount of acetyl-CoA in a microorganism it is therefore desirable that acetyl-CoA is formed via a different pathway to avoid the loss of carbon atoms. By using a microorganism having phosphoketolase activity, phosphate and fructose-6-phosphate are converted to erythrose-4-phosphate and acetylphosphate and the phosphotransacetylase further converts acetylphosphate into acetyl-CoA without loss of a carbon atom. Thus, in the end, the yield of acetyl-CoA can be increased by using a microorganism having phosphoketolase activity. Such a microorganism is capable of converting glucose into acetyl-CoA without loss of a carbon atom. Recombinant microorganisms in which a phosphoketolase is naturally or heterologously expressed are disclosed in U.S. Pat. Nos. 7,785,858 and 7,253,001.

The term "phosphoketolase activity" as used herein means an enzymatic activity that is capable of converting D-xylulose-5-phosphate into D-glyceraldehyde-3-phosphate according to the following reaction:

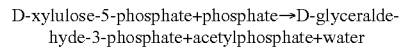

D-xylulose-5-phosphate+phosphate→D-glyceraldehyde-3-phosphate+acetylphosphate+water or that is capable to catalyze the above shown reaction and that is also able to convert D-fructose-6-phosphate to D-erythrose-4-phosphate according to the following reaction:

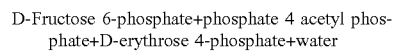

D-Fructose 6-phosphate+phosphate 4 acetyl phosphate+D-erythrose 4-phosphate+water The former phosphoketolases are usually classified in EC 4.1.2.9 and the latter in EC 4.1.2.22. Both types of phosphoketolases can be employed in the scope of the present invention. FIG. 1 shows schemes for the overall reactions using the two options of the phosphoketolase as described herein.

This enzymatic activity can be measured by assays known in the art. An example for such an assay is given in the Example section below.

In the context of the present invention, a microorganism which has phosphoketolase activity can, e.g., be a microorganism which naturally has phosphoketolase activity or a microorganism that does not naturally have phosphoketolase activity and has been genetically modified to express a phosphoketolase or a microorganism which naturally has phosphoketolase activity and which has been genetically modified, e.g. transformed with a nucleic acid, e.g. a vector, encoding a phosphoketolase in order to increase the phosphoketolase activity in said microorganism.

Microorganisms that inherently, i.e. naturally, have phosphoketolase activity are known in the art and any of them can be used in the context of the present invention.

It is also possible in the context of the present invention that the microorganism is a microorganism which naturally does not have phosphoketolase activity but which is genetically modified so as to comprise a nucleotide sequence allowing the expression of a phosphoketolase. Similarly, the microorganism may also be a microorganism which naturally has phosphoketolase activity but which is genetically modified so as to enhance the phosphoketolase activity, e.g. by the introduction of an exogenous nucleotide sequence encoding a phosphoketolase.

The genetic modification of microorganisms to express an enzyme of interest will be described in detail below.

The phosphoketolase expressed in the microorganism can be any phosphoketolase, in particular a phosphoketolase from prokaryotic or eukaryotic organisms. Prokaryotic phosphoketolases are described, e.g., from *Lactococcus lactis*.

The phosphoketolase expressed in the microorganism can be a naturally occurring phosphoketolase or it can be a phosphoketolase which is derived from a naturally occurring phosphoketolase, e.g. by the introduction of mutations or other alterations which, e.g., alter or improve the enzymatic activity, the stability, etc.

The microorganism is preferably further characterised by having a diminished or inactivated Embden-Meyerhof-Parnas pathway (EMPP) by inactivation of the gene(s) encoding a phosphofructokinase or by reducing the phosphofructokinase activity as compared to a non-modified microorganism or by not possessing phosphofructokinase activity. Thus, the microorganism is either a microorganism which naturally has an EMPP including phosphofructokinase activity but which has been modified, in particular genetically modified, so that the phosphofructokinase activity is either completely abolished or so that it is reduced compared to the corresponding non-modified microorganism, or the microorganism is a microorganism which naturally does not possess a phosphofructokinase activity.

As already mentioned above, when glucose is processed via the EMPP to acetyl-CoA, one carbon atom is lost by the release of $CO_2$ in the last step. By introducing the phosphoketolase, this loss can be avoided. Since fructose-6-phosphate is a substrate for the phosphoketolase, it is desirable that the pool of fructose-6-phosphate is kept at a high level in the microorganism in order to increase the yield in acetyl-CoA. Since fructose-6-phosphate is also a substrate for an enzyme of the Embden-Meyerhof-Parnas pathway, i.e. the phosphofructokinase, the recombinant microorganism has a reduced phosphofructokinase activity as compared to a non-modified microorganism or the gene(s) encoding a phosphofructokinase has/have been inactivated. This ensures the flux of fructose-6-phosphate is directed to the phosphoketolase and to the production of acetyl-CoA without loss of $CO_2$ because fructose-6-phosphate or most of fructose-6-phosphate can no longer be processed via the Embden-Meyerhof-Parnas pathway. Recombinant microorganisms in which a phosphoketolase is naturally or heterologously expressed and which have reduced phosphofructokinase activity are disclosed in U.S. Pat. No. 7,785,858.

The "phosphofructokinase activity" means an enzymatic activity that converts ATP and fructose-6-phosphate to ADP and fructose-1,6-bisphosphate (EC 2.7.1.11). This enzymatic activity can be measured by assays known in the art as, for example, described by Kotlarz et al. (Methods Enzymol. (1982) 90, 60-70).

The term "a microorganism which is characterised by having a diminished or inactivated Embden-Meyerhof-Parnas pathway (EMPP) by inactivation of the gene(s) encoding a phosphofructokinase or by reducing the phosphofructokinase activity as compared to a non-modified microorganism" preferably refers to a microorganism in which the inactivation of the gene(s) encoding a phosphofructokinase or the reduction of the phosphofructokinase activity as compared to a non-modified microorganism is achieved by a genetic modification of the microorganism which leads to said inactivation or reduction.

In a preferred embodiment, the recombinant microorganism is a recombinant microorganism that has an inactivated Embden-Meyerhof-Parnas pathway (EMPP) by inactivation of the gene(s) encoding a phosphofructokinase. The inactivation of the gene(s) encoding a phosphofructokinase in the context of the present invention means that the gene(s) coding for phosphofructokinase which are present in the microorganism is (are) inactivated so that they are no longer expressed and/or do not lead to the synthesis of functional phosphofructokinase. Inactivation can be achieved by many different ways known in the art. The inactivation can, e.g., be achieved by the disruption of the gene(s) encoding the phosphofructokinase or by clean deletion of said gene(s) through the introduction of a selection marker. Alternatively, the promoter of the gene(s) encoding the phosphofructokinase can be mutated in a way that the gene is no longer transcribed into mRNA. Other ways to inactivate the gene(s) encoding the phosphofructokinase known in the art are: to express a polynucleotide encoding RNA having a nucleotide sequence complementary to the transcript of the phosphofructokinase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the phosphofructokinase.

The term "inactivation" in the context of the present invention preferably means complete inactivation, i.e. that the microorganism does not show phosphofructokinase activity. This means in particular that the microorganism does not show phosphofructokinase activity independent from the used growth conditions. Preferably, "inactivation" means that the gene(s) encoding phosphofructokinase which are present in the microorganism are genetically modified so as to prevent the expression of the enzyme. This can be achieved, e.g., by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism is a recombinant microorganism that has a diminished Embden-Meyerhof-Parnas pathway (EMPP) by reducing the phosphofructokinase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above.

In the context of the present invention, a "reduced activity" means that the expression and/or the activity of an enzyme, in particular of the phosphofructokinase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a phosphofructokinase are known in the art.

In another embodiment the microorganism is a microorganism which does not possess a phosphofructokinase activity. This preferably means that such a microorganism naturally does not possess a phosphofructokinase activity. This means that such a microorganism does naturally not contain in its genome a nucleotide sequence encoding an enzyme with phosphofructokinase activity. Examples for such microorganisms are *Zymomonas mobilis* (J. S. Suo et al., Nat. Biotechnol. 23:63 (2005)) and *Ralstonia eutropha* (C. Fleige et al., Appl. Microb. Cell Physiol. 91:769 (2011)).

The microorganism may be further characterised by having a diminished or inactivated oxidative branch of the pentose phosphate pathway (PPP) by inactivation of the gene(s) encoding a glucose-6-phosphate dehydrogenase or by reducing the glucose-6-phosphate dehydrogenase activity as compared to a non-modified microorganism or by not possessing glucose-6-phosphate dehydrogenase activity. Thus, the microorganism is preferably either a microorganism which naturally has a PPP including glucose-6-phosphate dehydrogenase activity but which has been modified, in particular genetically modified, so that the glucose-6-phosphate dehydrogenase activity is either completely abolished or so that it is reduced compared to the corresponding non-modified microorganism, or the microorganism is a microorganism which naturally does not possess a glucose-6-phosphate dehydrogenase activity.

Diminishing or inactivating the oxidative branch of the pentose phosphate pathway further increases the yield in acetyl-CoA since glucose-6-phosphate will no longer be drawn through the pentose phosphate cycle. All or almost all glucose-6-phosphate in the microorganism will be converted into fructose-6-phosphate which will then be further converted into acetyl-CoA.

The "glucose-6-phosphate dehydrogenase activity" means an enzymatic activity that converts glucose-6-phosphate and $NADP^+$ to 6-phosphoglucono-δ-lactone and NADPH (EC 1.1.1.49). This enzymatic activity can be measured by assays known in the art as, for example, described by Noltmann et al. (J. Biol. Chem. (1961) 236, 1225-1230).

The term "a microorganism which is characterised by having a diminished or inactivated oxidative branch of the pentose phosphate pathway (PPP) by inactivation of the gene(s) encoding a glucose-6-phosphate dehydrogenase or by reducing the glucose-6-phosphate dehydrogenase activity as compared to a non-modified microorganism" preferably refers to a microorganism in which the inactivation of the gene(s) encoding a glucose-6-phosphate dehydrogenase or the reduction of the glucose-6-phosphate dehydrogenase activity as compared to a non-modified microorganism is achieved by a genetic modification of the microorganism which leads to said inactivation or reduction.

In a preferred embodiment, the recombinant microorganism is a recombinant microorganism that has an inactivated oxidative branch of the pentose phosphate pathway (PPP) by inactivation of the gene(s) encoding a glucose-6-phosphate dehydrogenase. The inactivation of the gene(s) encoding a glucose-6-phosphate dehydrogenase in the context of the present invention means that the gene(s) coding for glucose-6-phosphate dehydrogenase which is (are) present in the microorganism is (are) inactivated so that they are no longer expressed and/or do not lead to the synthesis of functional glucose-6-phosphate dehydrogenase. Inactivation can be achieved by many different ways known in the art. The inactivation can, e.g., be achieved by the disruption of the gene(s) encoding the glucose-6-phosphate dehydrogenase or by clean deletion of said gene(s) through the introduction of a selection marker. Alternatively, the promoter of the gene(s) encoding the glucose-6-phosphate dehydrogenase can be mutated in a way that the gene(s) is/are no longer transcribed into mRNA. Other ways to inactivate the gene(s) encoding the glucose-6-phosphate dehydrogenase known in the art are: to express a polynucleotide encoding RNA having a nucleotide sequence complementary to the transcript of the glucose-6-phosphate dehydrogenase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the glucose-6-phosphate dehydrogenase.

The term "inactivation" in the context of the present invention preferably means complete inactivation, i.e. that the microorganism does not show glucose-6-phosphate dehydrogenase activity. This means in particular that the microorganism does not show glucose-6-phosphate dehydrogenase activity independent from the used growth conditions.

Preferably, "inactivation" means that the gene(s) encoding glucose-6-phosphate dehydrogenase which are present in the microorganism are genetically modified so as to prevent the expression of the enzyme. This can be achieved, e.g., by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism is a recombinant microorganism that has a diminished oxidative branch of the pentose phosphate pathway (PPP) by reducing the glucose-6-phosphate dehydrogenase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above.

In the context of the present invention, a "reduced activity" means that the expression and/or the activity of an enzyme, in particular of the glucose-6-phosphate dehydrogenase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a glucose-6-phosphate dehydrogenase are known in the art.

In another embodiment the microorganism is a microorganism which does not possess a glucose-6-phosphate dehydrogenase activity. This preferably means that such a microorganism naturally does not possess a glucose-6-phosphate dehydrogenase activity. This means that such a microorganism does naturally not contain in its genome a nucleotide sequence encoding an enzyme with glucose-6-phosphate dehydrogenase activity. Examples for such microorganisms are *Acinetobacter baylyi* (Barbe et al., Nucl. Acids Res. 32 (2004), 5766-5779), archae of the hyperthermophilic phylum such as *Sulfolobus solfataricus* (Nunn et al., J. Biol. Chem. 285 (2010), 33701-33709), *Thermoproteus tenax*, *Thermoplasma acidophilum* and *Picrophilus torridus* (Reher and Schönheit, FEBS Lett. 580 (2006), 1198-1204).

The microorganism may in principle also be characterised by having fructose-1,6-bisphosphate phosphatase activity. However, as described above, since this enzyme may be inhibited by high levels of glucose, it is preferable that its action is replaced by the method according to the present invention for producing fructose-6-phosphate (F6P) from dihydroxyacetone phosphate (DHAP) and glyceraldehyde-3-phosphate (G3P). The fructose-6-phosphate can then again be converted via the phosphoketolase pathway to acetyl-CoA. Indeed, the product acetyl phosphate of phosphoketolase interconverts into acetyl-CoA through the action of the enzyme phosphate acetyltransferase EC 2.3.1.8. Thus, the recombinant microorganism is capable of producing acetyl-CoA from glucose at a stoichiometry approaching 3:1. The sum of the reactions is given in equation 2:

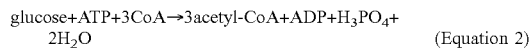

(Equation 2)

In another embodiment, the microorganism is further characterised in that the EMPP is further diminished or inactivated by inactivation of the gene(s) encoding the glyceraldehyde 3-phosphate dehydrogenase or by reducing the glyceraldehyde 3-phosphate dehydrogenase activity as compared to a non-modified microorganism. Further diminishing the EMPP at a step further downstream by diminishing or inactivating the glyceraldehyde 3-phosphate dehydrogenase ensures that none or almost none glyceraldehyde 3-phosphate that may be produced in the microorganism will be processed via the glycolysis to acetyl-CoA whereby one carbon atom would be lost by the release of $CO_2$ in the last step catalysed by the pyruvate dehydrogenase. Therefore, blocking the EMPP by diminishing or inactivating the glyceraldehyde 3-phosphate dehydrogenase activity further ensures that the overall flux is directed towards the phosphoketolase.

The "glyceraldehyde 3-phosphate dehydrogenase activity" means an enzymatic activity that converts glyceraldehyde 3-phosphate, phosphate and $NAD^+$ to 3-phospho-D-glyceroyl phosphate and $NADH+H^+$ (EC 1.2.1.12). This activity can be measured by assays known in the art as, for example, described by D'Alessio et al. (J. Biol. Chem. (1971) 246, 4326-4333).

The term "a microorganism which is characterised by having a further diminished or inactivated Embden-Meyerhof-Parnas pathway (EMPP) by inactivation of the gene(s) encoding a glyceraldehyde 3-phosphate dehydrogenase or by reducing the glyceraldehyde 3-phosphate dehydrogenase activity as compared to a non-modified microorganism" preferably refers to a microorganism in which the inactivation of the gene(s) encoding a glyceraldehyde 3-phosphate dehydrogenase or the reduction of the glyceraldehyde 3-phosphate dehydrogenase activity as compared to a non-modified microorganism is achieved by a genetic modification of the microorganism which leads to said inactivation or reduction.

In a preferred embodiment, the recombinant microorganism is a recombinant microorganism in which the EMPP is further diminished or inactivated by inactivation of the gene(s) encoding the glyceraldehyde 3-phosphate dehydrogenase or by reducing the glyceraldehyde 3-phosphate dehydrogenase activity as compared to a non-modified microorganism. The inactivation of the gene(s) encoding a glyceraldehyde 3-phosphate dehydrogenase in the context of the present invention means that the gene(s) coding for glyceraldehyde 3-phosphate dehydrogenase which is (are) present in the microorganism is (are) inactivated so that they are no longer expressed and/or do not lead to the synthesis of functional glyceraldehyde 3-phosphate dehydrogenase. Inactivation can be achieved by many different ways known in the art. The inactivation can, e.g., be achieved by the disruption of the gene(s) encoding the glyceraldehyde 3-phosphate dehydrogenase or by clean deletion of said gene(s) through the introduction of a selection marker. Alternatively, the promoter of the gene encoding the glyceraldehyde 3-phosphate dehydrogenase can be mutated in a way that the gene(s) is/are no longer transcribed into mRNA. Other ways to inactivate the gene(s) encoding the glyceraldehyde 3-phosphate dehydrogenase known in the art are: to express a polynucleotide encoding RNA having a nucleotide sequence complementary to the transcript of the glyceraldehyde 3-phosphate dehydrogenase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the glyceraldehyde 3-phosphate dehydrogenase.

The term "inactivation" in the context of the present invention preferably means complete inactivation, i.e. that the microorganism does not show glyceraldehyde 3-phosphate dehydrogenase activity. This means in particular that the microorganism does not show glyceraldehyde 3-phosphate dehydrogenase activity independent from the used growth conditions.

Preferably, "inactivation" means that the gene(s) encoding glyceraldehyde 3-phosphate dehydrogenase which are present in the microorganism are genetically modified so as to prevent the expression of the enzyme. This can be achieved, e.g., by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism is a recombinant microorganism that has a diminished EMPP by reducing the glyceraldehyde 3-phosphate dehydrogenase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above.

In the context of the present invention, a "reduced activity" means that the expression and/or the activity of an enzyme, in particular of the glyceraldehyde 3-phosphate dehydrogenase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a glyceraldehyde 3-phosphate dehydrogenase are known in the art.

In another embodiment, where the recombinant microorganism is a bacterium, the gene(s) encoding the PEP-dependent PTS transporter have been inactivated. In the context of the present invention, inactivation means that the gene(s) coding for PEP-dependent PTS transporter which is (are) present in the microorganism is (are) inactivated so that they are no longer expressed and/or do not lead to the synthesis of functional PEP-dependent PTS transporter. The inactivation of the gene(s) encoding the PEP-dependent PTS transporter should be such that the bacteria are no longer capable of transporting glucose via the PEP-dependent PTS transporter. PEP-dependent PTS transporter (e.g. from *E. coli, B. subtilis*) are known in the art. An example for inactivation of the PEP-dependent PTS transporter is shown in the Example section below.

Inactivation can be achieved by many different ways known in the art. The inactivation can, e.g., be achieved by the disruption of the gene(s) encoding the PEP-dependent PTS transporter or by clean deletion of said gene(s) through the introduction of a selection marker. Alternatively, the promoter of the gene(s) encoding the PEP-dependent PTS transporter can be mutated in a way that the gene(s) is (are) no longer transcribed into mRNA. Other ways to inactivate the gene(s) encoding the PEP-dependent PTS transporter known in the art are: to express a polynucleotide encoding RNA having a nucleotide sequence complementary to the transcript of the PEP-dependent PTS transporter gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the PEP-dependent PTS transporter.

In a preferred embodiment, the method of the present invention makes use of an organism, preferably a microorganism, which is capable of consuming glucose.

In another preferred embodiment, the method of the present invention makes use of an organism, preferably a microorganism, which is capable of consuming fructose.

In another preferred embodiment, the method of the present invention makes use of an organism, preferably a microorganism, which is capable of consuming xylose.

In another preferred embodiment, the method of the present invention makes use of an organism, preferably a microorganism, which is capable of consuming mannose. In another preferred embodiment, the method of the present invention makes use of an organism, preferably a microorganism, which is capable of consuming more than one sugar. Preferably, said more than one sugar comprises sucrose, glucose, mannose and/or xylose. In a more preferred embodiment, the method of the present invention makes use of an organism, preferably a microorganism, which is capable of consuming two or more sugars selected from the group consisting of sucrose, glucose, mannose and xylose. Organisms and/or microorganisms which are capable of consuming glucose, fructose, xylose and/or mannose do naturally occur and are known in the art.

In another embodiment, said organism and/or microorganism is genetically modified in order to be capable of consuming glucose, fructose, xylose and/or mannose and/or genetically modified in order to increase the organism's and/or microorganism's capability of consuming glucose, fructose, xylose and/or mannose. Corresponding genetic modifications are known in the art.

In one embodiment, the method of the present invention makes use of an organism, preferably a microorganism which is capable of consuming sugar through a Phosphotransferase Transport System (PTS).

In another embodiment, the method of the present invention makes use of an organism, preferably a microorganism which is capable of consuming sugar through a non-Phosphotransferase Transport System (non-PTS).

Organisms and/or microorganisms which are capable of consuming sugar through a Phosphotransferase Transport System (PTS) and/or through a non-Phosphotransferase Transport System (non-PTS) are known in the art.

In another embodiment, said organism and/or microorganism is genetically modified in order to be capable of consuming sugar through a Phosphotransferase Transport System (PTS) or through a non-Phosphotransferase Transport System (non-PTS). In another preferred embodiment, said organism and/or microorganism is genetically modified in order to increase the organism's and/or microorganism's capability of consuming sugar through a Phosphotransferase Transport System (PTS) or through a non-Phosphotransferase Transport System (non-PTS). Corresponding genetic modifications are known in the art.

In another preferred embodiment, the method of the present invention makes use of an organism, preferably a microorganism having a diminished or inactivated Phosphotransferase Transport System (PTS).

Without being bound to theory, such an organism, preferably a microorganism, may preferably be genetically modified by deleting or inactivating (a) gene(s) of said Phosphotransferase Transport System (PTS).

Corresponding genetic modifications are known in the art.

In another preferred embodiment, the method of the present invention makes use of an organism, preferably a microorganism having an enhanced non-Phosphotransferase Transport System (non-PTS) for sugar uptake.

Without being bound to theory, such an organism, preferably a microorganism, may preferably be genetically modified by overexpressing (a) gene(s) of said non-Phosphotransferase Transport System (non-PTS) for sugar uptake.

Corresponding genetic modifications are known in the art.

In another preferred embodiment, the method of the present invention makes use of an organism, preferably a microorganism having a diminished or inactivated Phosphotransferase Transport System (PTS) and an enhanced non Phosphotransferase Transport System (non-PTS) for sugar uptake.

In another preferred embodiment, the method of the present invention makes use of an organism, preferably a microorganism which is capable of consuming sucrose through a non-Phosphotransferase Transport System (non-PTS).

In another preferred embodiment, the method of the present invention makes use of an organism, preferably a microorganism consuming sucrose, wherein said organism, preferably said microorganism, has genetically been modified by the introduction of at least one gene of a non-Phosphotransferase Transport System (non-PTS). Without being bound to theory, such an organism and/or microorganism has genetically been modified by introducing a gene selected from the group consisting of cscA, cscB, and cscK from *Escherichia coli* W (M. Bruschi et al., Biotechnology Advances 30 (2012) 1001-1010).

In another preferred embodiment, the method of the present invention makes use of an organism, preferably a microorganism which has genetically been modified to have a diminished or inactivated Phosphotransferase Transport System (PTS) and an overexpression of at least one gene selected from the group consisting of galP, glk and glf.

In a preferred embodiment, the method of the present invention makes use of an organism, preferably a microorganism, which is genetically modified in order to avoid the leakage of acetyl-CoA, thereby increasing the intracellular concentration of acetyl-CoA. Genetic modifications leading to an increase in the intracellular concentration of acetyl-CoA are known in the art. Without being bound to theory, such an organism, preferably a microorganism, may preferably be genetically modified by deleting or inactivating one or more of the following genes:

ΔackA (acetate kinase), Δldh (lactate dehydrogenase), ΔadhE (alcohol dehydrogenase), ΔfrdB and/or ΔfrdC (fumarate reductase and fumarate dehydrogenase), ΔpoxB (pyruvate oxidase), Δpgk (phosphoglycerate kinase), ΔiclR (DNA-binding transcriptional repressor IclR).

Further deletions which may be advantageous in the context of the present invention are deletions in the genes encoding 6-phosphogluconate dehydratase (e.g. the edd gene in *E. coli*) and/or in the genes encoding 2-keto-3-deoxy-6-phosphogluconate aldolase (e.g. the eda gene in *E. coli*).

Alternatively, or in addition to any of the above deletions, the organism or microorganism may genetically be modified by overexpressing the gene panK/coaA encoding pantothenate kinase, thereby increasing the CoA/acetyl-CoA intracellular pool.

These modifications which avoid the leakage of acetyl-CoA are known in the art and corresponding modified organisms have been used in methods for the bioconversion of exogenous isoamyl alcohol into isoamyl acetate by an *E. coli* strain expressing ATF2 (Metab. Eng. 6 (2004), 294-309).

Further genes which may be overexpressed in the organism or microorganism include the following:
 pckA (phosphoenolpyruvate carboxykinase)
 tktA (transketolase 1)
 tktB (transketolase 2)
 talA (transaldolase A)
 talB (transaldolase B)
 rpiA (ribose-5-phosphate isomerase A)
 rpiB (ribose-5-phosphate isomerase B)
 rpE (ribulose-phosphate 3-epimerase)
 pgi (glucose-6-phosphate isomerase)
 galP (galactose: H$^+$ symporter)
 glk (glucokinase)
 glf (glucose facilitated diffusion protein)
 pta (phosphate acetyltransferase)

The recombinant microorganism may further be characterized in that it is capable of converting acetyl-CoA into acetone. Methods for providing such a recombinant microorganism are for instance disclosed in EP 2 295 593. The term "which is capable of converting acetyl-CoA into acetone" in the context of the present invention means that the organism/microorganism has the capacity to produce acetone within the cell due to the presence of enzymes providing enzymatic activities allowing the production of acetone from acetyl-CoA.

Acetone is produced by certain microorganisms, such as *Clostridium acetobutylicum*, *Clostridium beijerinckii*, *Clostridium cellulolyticum*, *Bacillus polymyxa* and *Pseudomonas putida*. The synthesis of acetone is best characterized in *Clostridium acetobutylicum*. It starts out with a reaction (reaction step 1) in which two molecules of acetyl-CoA are condensed into acetoacetyl-CoA. This reaction is catalyzed by acetyl-CoA acetyltransferase (EC 2.3.1.9). Acetoacetyl-CoA is then converted into acetoacetate by a reaction with acetic acid or butyric acid resulting also in the production of acetyl-CoA or butyryl-CoA (reaction step 2). This reaction is catalyzed e.g. by acetoacetylCoA transferase (EC 2.8.3.8). AcetoacetylCoA transferase is known from various organisms, e.g. from *E. coli* in which it is encoded by the atoAD gene or from *Clostridium acetobutylicum* in which it is encoded by the ctfAB gene. However, also other enzymes can catalyze this reaction, e.g. 3-oxoacid CoA transferase (EC 2.8.3.5) or succinate CoA ligase (EC 6.2.1.5).

Finally, acetoacetate is converted into acetone by a decarboxylation step (reaction step 3) catalyzed by acetoacetate decarboxylase (EC 4.1.1.4).

The above described reaction steps 1 and 2 and the enzymes catalyzing them are not characteristic for the acetone synthesis and can be found in various organism. In contrast, reaction step 3 which is catalyzed by acetoacetate decarboxylase (EC 4.1.1.4) is only found in those organisms which are capable of producing acetone.

In a preferred embodiment the recombinant microorganism is a microorganism, which naturally has the capacity to produce acetone. Thus, preferably the microorganism belongs to the genus *Clostridium*, *Bacillus* or *Pseudomonas*, more preferably to the species *Clostridium acetobutylicum*, *Clostridium beijerinckii*, *Clostridium cellulolyticum*, *Bacillus polymyxa* or *Pseudomonas putida*.

In another preferred embodiment, the recombinant microorganism is a microorganism, derived from an organism/microorganism which naturally does not produce acetone but which has been genetically modified so as to produce acetone, i.e. by introducing the gene(s) necessary for allowing the production of acetone in the microorganism. In principle any microorganism can be genetically modified in this way. The enzymes responsible for the synthesis of acetone have been described above. Genes encoding corresponding enzymes are known in the art and can be used to genetically modify a given microorganism so as to produce acetone. As described above, the reaction steps 1 and 2 of the acetone synthesis occur naturally in most organisms. However, reaction step 3 is characteristic and crucial for acetone synthesis. Thus, in a preferred embodiment, a genetically modified microorganism derived from a microorganism which naturally does not produce acetone is modified so as to contain a nucleotide sequence encoding an enzyme catalyzing the conversion of acetoacetate into acetone by decarboxylation, e.g. an acetoacetate decarboxylase (EC 4.1.1.4). Nucleotide sequences from several organisms encoding this enzyme are known in the art, e.g. the adc gene from *Clostridium acetobutylicum* (Uniprot accession numbers P23670 and P23673), *Clostridium beijerinckii* (*Clostridium* MP; Q9RPK1), *Clostridium pasteurianum* (Uniprot accession number P81336), *Bradyrhizobium* sp. (strain BTAi1/ATCC BAA-1182; Uniprot accession number A5EBU7), *Burkholderia mallei* (ATCC 10399 A9LBS0), *Burkholderia mallei* (Uniprot accession number A3MAE3), *Burkholderia mallei* FMH A5XJB2, *Burkholderia cenocepacia* (Uniprot accession number A0B471), *Burkholderia ambifaria* (Uniprot accession number Q0b5P1), *Burkholderia phytofirmans* (Uniprot accession number B2T319), *Burkholderia* spec. (Uniprot accession number Q38ZU0), *Clostridium botuli-* num (Uniprot accession number B2TLN8), *Ralstonia pickettii* (Uniprot accession number B2UIG7), *Streptomyces nogalater* (Uniprot accession number Q9EYI7), *Streptomyces avermitilis* (Uniprot accession number Q82NF4), *Legionella pneumophila* (Uniprot accession number Q5ZXQ9), *Lactobacillus salivarius* (Uniprot accession number Q1WVG5), *Rhodococcus* spec. (Uniprot accession number Q0S7W4), *Lactobacillus plantarum* (Uniprot accession number Q890G0), *Rhizobium leguminosarum* (Uniprot accession number Q1M911), *Lactobacillus casei* (Uniprot accession number Q03B66), *Francisella tularensis* (Uniprot accession number QOBLC9), *Saccharopolyspora erythreae* (Uniprot accession number A4FKR9), *Korarchaeum cryptofilum* (Uniprot accession number B1L3N6), *Bacillus amyloliquefaciens* (Uniprot accession number A7Z8K8), *Cochliobolus heterostrophus* (Uniprot accession number Q8NJQ3), *Sulfolobus islandicus* (Uniprot accession number C3ML22) and *Francisella tularensis* subsp. *holarctica* (strain OSU18).

More preferably, the microorganism is genetically modified so as to be transformed with a nucleic acid molecule encoding an enzyme capable of catalyzing the above mentioned reaction step 2 of the acetone synthesis, i.e. the conversion of acetoacetyl CoA into acetoacetate.

Even more preferably, the microorganism is genetically modified so as to be transformed with a nucleic acid molecule encoding an enzyme capable of catalyzing the above mentioned reaction step 1 of the acetone synthesis, i.e. the condensation of two molecules of acetyl CoA into acetoacetatyl CoA.

In a particularly preferred embodiment the microorganism is genetically modified so as to be transformed with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis.

Methods for preparing the above mentioned genetically modified microorganisms are well known in the art. Thus, generally, the microorganism is transformed with a DNA construct allowing expression of the respective enzyme in the microorganism. Such a construct normally comprises the coding sequence in question linked to regulatory sequences allowing transcription and translation in the respective host cell, e.g. a promoter and/enhancer and/or transcription terminator and/or ribosome binding sites etc. The prior art already describes microorganisms which have been genetically modified so as to be able to produce acetone. In particular, genes from, e.g., *Clostridium acetobutylicum* have been introduced into *E. coli* thereby allowing the synthesis of acetone in *E. coli*, a bacterium which naturally does not produce acetone (Bermejo et al., Appl. Environ. Microbiol. 64 (1998); 1079-1085; Hanai et al., Appl. Environ. Microbiol. 73 (2007), 7814-7818). In particular Hanai et al. (loc. cit.) shows that it is sufficient to introduce a nucleic acid sequence encoding an acetoacetate decarboxylase (such as that from *Clostridium acetobutylicum*) in order to achieve acetone production in *E. coli* indicating that the endogenous enzymes in *E. coli* catalyzing the above-mentioned reaction steps 1 and 2 (i.e. the expression products of the *E. coli* atoB and atoAD genes) are sufficient to provide substrate for the acetone production.

In another aspect, the recombinant microorganism is further characterized in that it is capable of converting acetyl-CoA into acetone and converting acetone into isobutene. Methods for providing such a recombinant microorganism are for instance disclosed in EP-A 2 295 593 (EP 09 17 0312), WO 2011/032934, WO 2015/101493, WO 2014/086780, WO 2010/001078, WO 2012/052427, WO 2017/071124, WO 2015/004211, WO 2014/064198 and WO 2014/086781.

In another aspect, the recombinant microorganism is further characterized in that it is capable of converting acetyl-CoA into isobutene using a metabolic route that does not include an acetone intermediate. Methods for providing such a recombinant microorganism are, for instance, disclosed in WO2016042012, WO2017/085167, WO2018/206262, WO2013/186215, WO2016/034691, WO2017/191239, US2019/0100742, WO 2016/042011, WO 2017/162738, WO2015082447, WO 2010/001078, WO 2012/052427, WO 2017/071124, WO 2015/004211, WO 2014/064198 and WO 2014/086781.

In another aspect, the recombinant microorganism is characterized in that it is capable of converting acetyl-CoA into acetone and converting acetone into propene. Methods for providing such a recombinant microorganism are for instance disclosed in Hanai et al., Appl. Environ. Microbiol. 73 (2007), 7814-7818.

In another aspect, the recombinant microorganism is characterized in that it is capable of converting acetyl-CoA into acetone and converting acetone into isopropanol.

Acetone conversion to isopropanol needs a secondary-alcohol dehydrogenase that converts acetone to isopropanol in an NADPH-dependent reaction (Chen, J.-S., FEMS Microbiol. Rev. 17:263-273 (1995)).

Accordingly, in another aspect, the recombinant microorganism is characterized in that it is capable of converting acetone into isopropanol by the (over)expression of a secondary-alcohol dehydrogenase.

To increase NADPH availability, expression of transhydrogenase enzymes (like PntAB and UdhA (SthA)) can be modified (Jan et al., Biotechnol Prog. 29(5):1124-30 (2013)).

Accordingly, in another aspect, the recombinant microorganism is characterized in that the availability of NADPH is increased by, e.g., the (over)expression of one or more transhydrogenase enzymes, preferably PntAB and UdhA (SthA).

In a preferred embodiment, it is envisaged to effect further gene deletions in order to increase acetone and, consequently isopropanol production. It can, for example, be advantageous in this context to delete one or more, preferably all of the following genes: fsaA (coding for fructose-6-phosphate aldolase 1) and fsaB (coding for fructose-6-phosphate aldolase 2).

Preferably, in order to further increase isopropanol production, further genes which may be modified to be overrexpressed are the pntAB (pyridine nucleotide transhydrogenase subunits alpha and beta, Uniprot P07001 and P0AB67, NCBI Reference Sequences: NP_416120.1 and NP_416119.1) genes, preferably from E. coli.

In a more preferred embodiment, the organism or microorganism is characterized in that it overexpresses one or more of the following genes for the conversion of acetyl-CoA into acetone and/or isopropanol:

for the above step 1: thlA (acetyl-CoA transferase; NCBI reference WP_010966157.1; UniProt Accession Number P45359); preferably the thlA gene from *Clostridium acetobutylicum* for the above step 2: atoD, atoA (acetate CoA-transferase; NCBI reference NP_416725.1 and NP_416726.1; UniProt Accession Number P76458 and P76459, respectively); preferably the atoD, atoA genes from *Escherichia coli* for the above step 3: adc (Acetoacetate decarboxylase; NCBI reference NP_149328.1; UniProt Accession Number P23670); preferably the adc gene from *Clostridium acetobutylicum* for a step 4: adh (NADP-dependent isopropanol dehydrogenase; NCBI reference AF_157307.2; UniProt Accession Number P25984); preferably the adh gene from *Clostridium beijerinckii*

One skilled in the art would recognize that further genetic modifications to the microorganisms of the present invention could lead to improvements in the efficacy by which the microorganisms of the present invention convert feedstock to product. For example, natural microorganisms commonly produce products such as formate, acetate, lactate, succinate, ethanol, glycerol, 2,3-butanediol, methylglyoxal and hydrogen; all of which would be deleterious to the production of, e.g., acetone, isobutene or propene from sugars. Elimination or substantial reduction of such unwanted by-products may be achieved by elimination or reduction of key enzymes activities leading their production. Such activities include, but are not limited to, the group consisting of:

acetyl-CoA+formate=CoA+pyruvate (for example, catalyzed by formate C-acetyltransferase, also known as pyruvate formate-lyase (EC 2.3.1.54); for E. coli—pflB, NCBI-GeneID: 945514);

ATP+acetate=ADP+acetyl phosphate (for example, catalyzed by acetate kinase (EC 2.7.2.1); for E. coli—ackA, NCBI-GeneID: 946775);

(R)-lactate+$NAD^+$=pyruvate+NADH+$H^+$ (for example, catalyzed by L-lactate dehydrogenase (EC 1.1.1.28); for E. coli—ldhA, NCBI-GeneID: 946315);

succinate+acceptor=fumarate+reduced acceptor (for example, catalyzed by succinate dehydrogenase (EC 1.3.99.1); for E. coli—comprising frdA and frdB, NCBI-GeneID: 948667 and 948666, respectively);

a 2-oxo carboxylate (e.g. pyruvate)=an aldehyde (e.g. acetaldehyde+$CO_2$ (for example, catalyzed by pyruvate decarboxylase (EC 4.1.1.1));

acetaldehyde+CoA+$NAD^+$=acetyl-CoA+NADH+$H^+$ (for example, catalyzed by acetaldehyde dehydrogenase (acetylating) (EC 1.2.1.10); for E. coli—adhE, NCBI-GeneID: 945837);

sn-glycerol 3-phosphate+$NAD(P)^+$=glycerone phosphate+$NAD(P)H$+$H^+$ (for example, catalyzed by glycerol-3-phosphate dehydrogenase [$NAD(P)^+$] (EC 1.1.1.94); for E. coli—gpsA, NCBI-GeneID: 948125);

2 pyruvate=2-acetolactate+$CO_2$ (for example, catalyzed by acetolactate synthase (EC 2.2.1.6); for E. coli—ilvH and ilvI, NCBI-GeneID: 947267 and 948793, respectively);

glycerone phosphate=methylglyoxal+phosphate (for example, catalyzed by methylglyoxal synthase (EC 4.2.3.3); for E. coli—mgsA, NCBI-GeneID: 945574); and formate+$H^+$=$CO_2$+$H_2$ (for example, catalyzed by formate hydrogenlyase (EC 1.2.1.2 together with EC 1.12.1.2); for E. coli—fdhF (EC 1.2.1.2), NCBI-GeneID: 948584).

Thus, in a preferred embodiment, the microorganism may further be characterized in that one or more of the above listed enzyme activities are eliminated or reduced.

One skilled in the art would further recognize that genetic modifications to regulatory elements in the microorganisms of the present invention could lead to improvements in the efficacy by which the microorganisms of the present invention convert feedstock to product. Within E. coli, such genetic modifications include, but are not limited to, the group consisting of:

deleting the fnr gene (NCBI-GeneID: 945908), a global regulator of anaerobic growth, and deleting the rpoS gene (NCBI-GeneID: 947210), a RNA polymerase, sigma S (sigma 38) factor; and deleting the icIR gene (DNA-binding transcriptional repressor IcIR).

Thus, in another preferred embodiment the microorganism shows at least one of these deletions.

Thus, as described above, the method of the present invention can be implemented in recombinant microorganisms as described above which can be used for the conversion of glucose into acetyl-CoA. Acetyl CoA (also known as acetyl Coenzyme A) in chemical structure is the thioester between coenzyme A (a thiol) and acetic acid and is an important precursor molecule for the production of useful metabolites. Acetyl-CoA can then be further converted by the recombinant microorganism into useful metabolites such as L-glutamic acid, L-glutamine, L-proline, L-arginine, L-leucine, succinate and polyhydroxybutyrate.

The recombinant microorganism can also be used for converting acetyl-CoA into acetone.

The recombinant microorganism can also be used for converting acetyl-CoA into isobutene.

The recombinant microorganism can also be used for converting acetyl-CoA into propene.

The recombinant microorganism can also be used for converting acetyl-CoA into isopropanol.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic.

These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

When carried out by making use of a microorganism, the method according to the present invention may, e.g. be designed as a continuous fermentation culturing method or as a batch culture or any suitable culture method known to the person skilled in the art.

The present invention also relates to a method for the production of acetone and/or isobutene and/or propene from glucose or any of the other above-mentioned carbon sources in which the above-described recombinant microorganism is cultivated under conditions allowing for the production of acetone and/or isobutene and/or propene and in which the acetone and/or isobutene and/or propene is isolated. The microorganisms are cultivated under suitable culture conditions allowing the occurrence of the enzymatic reaction(s). The specific culture conditions depend on the specific microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another preferred embodiment the method according to the invention furthermore comprises the step of collecting gaseous products, in particular isobutene or propene, degassing out of the reaction, i.e. recovering the products which degas, e.g., out of the culture. Thus in a preferred embodiment, the method is carried out in the presence of a system for collecting isobutene or propene under gaseous form during the reaction.

As a matter of fact, short alkenes such as isobutene and propene adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

The enzymes used in the method according to the invention can be a naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. Preferably, the nucleic acid molecule introduced into the microorganism is a nucleic acid molecule which is heterologous with respect to the microorganism, i.e. it does not naturally occur in said microorganism.

In the context of the present invention, an "increased activity" preferably means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention furthermore relates to a recombinant microorganism which has been transformed with
(a) a nucleotide sequence encoding a phosphoric monoester hydrolase (EC 3.1.3.-); and
(b) a nucleotide sequence encoding an enzyme selected from the group consisting of
  (i) an aldehyde lyase (EC 4.1.2.-); and/or
  (ii) a transaldolase (EC 2.2.1.2).

In a preferred embodiment the phosphoric monoester hydrolase (EC 3.1.3.-) encoded by the corresponding nucleotide sequence is heterologous with respect to the microorganism which means that it does naturally not occur in this microorganism. More preferably the encoded enzyme originates from another microorganism, in particular from a microorganism from a different genus or a different species. In another embodiment the enzyme is artificial in that it does not occur in nature. This includes improved variants of the enzyme which have been prepared by mutagenesis approaches or genetic engineering.

In another preferred embodiment the aldehyde lyase (EC 4.1.2.-) or the transaldolase (EC 2.2.1.2) encoded by the corresponding nucleotide sequence is heterologous with respect to the microorganism which means that it does naturally not occur in this microorganism. More preferably the encoded enzyme originates from another microorganism, in particular from a microorganism from a different genus or a different species. In another embodiment the enzyme is artificial in that it does not occur in nature. This includes improved variants of the enzyme which have been prepared by mutagenesis approaches or genetic engineering.

In a particularly preferred embodiment both the enzymes mentioned in (a) and (b), above, are heterologous with respect to the microorganism.

The present invention also relates to the use of such a microorganism according to the present invention for first converting dihydroxyacetone phosphate (DHAP) into dihydroxyacetone (DHA) by the enzyme mentioned in (a) and then further converting the produced dihydroxyacetone (DHA) together with glyceraldehyde-3-phosphate (G3P) into fructose-6-phosphate (F6P) by an enzyme mentioned in (b).

The present invention furthermore relates to a recombinant microorganism which has been transformed with
(a) a nucleotide sequence encoding a phosphoric monoester hydrolase (EC 3.1.3.-); and
(b) a nucleotide sequence encoding a fructose bisphosphate aldolase (EC 4.1.2.13);
wherein said microorganism also possesses phosphoglucomutase (EC 5.4.2.2) or phosphomannomutase (EC 5.4.2.8) activity.

In a preferred embodiment the phosphoric monoester hydrolase (EC 3.1.3.-) encoded by the corresponding nucleotide sequence is heterologous with respect to the microorganism which means that it does naturally not occur in this microorganism. More preferably the encoded enzyme originates from another microorganism, in particular from a microorganism from a different genus or a different species. In another embodiment the enzyme is artificial in that it does not occur in nature. This includes improved variants of the enzyme which have been prepared by mutagenesis approaches or genetic engineering.

In another preferred embodiment the fructose bisphosphate aldolase (EC 4.1.2.13) encoded by the corresponding nucleotide sequence is heterologous with respect to the microorganism which means that it does naturally not occur in this microorganism. More preferably the encoded enzyme originates from another microorganism, in particular from a microorganism from a different genus or a different species. In another embodiment the enzyme is artificial in that it does not occur in nature. This includes improved variants of the enzyme which have been prepared by mutagenesis approaches or genetic engineering.

In a particularly preferred embodiment both the enzymes mentioned in (a) and (b), above, are heterologous with respect to the microorganism.

In a further preferred embodiment, such a microorganism has furthermore been transformed with
(c) a nucleotide sequence encoding an enzyme selected from the group consisting of:
  (i) Phosphoglucomutase (EC 5.4.2.2); or
  (ii) Phosphomannomutase (EC 5.4.2.8).

In a preferred embodiment the phosphoglucomutase (EC 5.4.2.2) or the phosphomannomutase (EC 5.4.2.8) encoded by the corresponding nucleotide sequence is heterologous with respect to the microorganism which means that it does naturally not occur in this microorganism. More preferably the encoded enzyme originates from another microorganism, in particular from a microorganism from a different genus or a different species. In another embodiment the enzyme is artificial in that it does not occur in nature. This includes improved variants of the enzyme which have been prepared by mutagenesis approaches or genetic engineering.

In a particularly preferred embodiment all three the enzymes mentioned in (a), (b) and (c), above, are heterologous with respect to the microorganism.

The present invention also relates to the use of such a microorganism according to the present invention for first converting glyceraldehyde-3-phosphate (G3P) into glyceraldehyde by the enzyme mentioned in (a) and then further converting the produced glyceraldehyde together with dihydroxyacetone phosphate (DHAP) into fructose-1-phosphate (F1P) by an enzyme mentioned in (b) and then further converting the produced fructose-1-phosphate (F1P) into fructose-6-phosphate (F6P) by an enzyme mentioned in (c).

A recombinant microorganism according to the present invention may furthermore display one or more of the features as described above for the microorganism in which the method according to the present invention can be implemented.

Accordingly, in a preferred embodiment, the microorganism is a recombinant microorganism which has been transformed with
(a) a nucleotide sequence encoding a phosphoric monoester hydrolase (EC 3.1.3.-); and
(b) a nucleotide sequence encoding an enzyme selected from the group consisting of
  (i) an aldehyde lyase (EC 4.1.2.-); and/or
  (ii) a transaldolase (EC 2.2.1.2);
and/or
which has been transformed with
(a) a nucleotide sequence encoding a phosphoric monoester hydrolase (EC 3.1.3.-); and (b) a nucleotide sequence encoding a fructose bisphosphate aldolase (EC 4.1.2.13);
wherein said microorganism also possesses phosphoglucomutase (EC 5.4.2.2) or phosphomannomutase (EC 5.4.2.8) activity
and which is furthermore characterized in that it:
a) has phosphoketolase activity;
b) (i) has a diminished or inactivated Embden-Meyerhof-Parnas pathway (EMPP) by inactivation of the gene(s) encoding phosphofructokinase or by reducing phosphofructokinase activity as compared to a non-modified microorganism; or
(ii) does not possess phosphofructokinase activity;
and
c) (i) has a diminished or inactivated oxidative branch of the pentose phosphate pathway (PPP) by inactivation of the gene(s) encoding glucose-6-phosphate dehydrogenase or by reducing glucose-6-phosphate dehydrogenase activity as compared to a non-modified microorganism; or
(ii) does not possess glucose-6-phosphate dehydrogenase activity.

As regards the enzymes which may be expressed by the microorganism and the preferred embodiments, the same applies as has been set forth above in connection with a method according to the invention and the microorganism of the invention.

The present invention furthermore relates to a combination of enzymes comprising
(a) a phosphoric monoester hydrolase (EC 3.1.3.-); and
(b) an enzyme selected from the group consisting of
(i) an aldehyde lyase (EC 4.1.2.-); and/or
(ii) a transaldolase (EC 2.2.1.2).

The present invention furthermore relates to a combination of enzymes comprising
(a) a phosphoric monoester hydrolase (EC 3.1.3.-); and
(b) a fructose bisphosphate aldolase (EC 4.1.2.13); and
(c) an enzyme selected from
(i) a phosphoglucomutase (EC 5.4.2.2); or
(ii) a phosphomannomutase (EC 5.4.2.8).

The present invention also relates to a composition comprising a microorganism according to the present invention or the combination of enzymes according to the present invention.

The present invention furthermore relates to the use of a combination of enzymes or of a microorganism or of a composition according to the present invention for first converting dihydroxyacetone phosphate (DHAP) into dihydroxyacetone (DHA) by the enzyme mentioned in (a) and then further converting the produced dihydroxyacetone (DHA) together with glyceraldehyde-3-phosphate (G3P) into fructose-6-phosphate (F6P) by an enzyme mentioned in (b) as described above, or for first converting glyceraldehyde-3-phosphate (G3P) into glyceraldehyde by the enzyme mentioned in (a) and then further converting the produced glyceraldehyde together with dihydroxyacetone phosphate (DHAP) into fructose-1-phosphate (F1P) by an enzyme mentioned in (b) and then further converting the produced fructose-1-phosphate (F1P) into fructose-6-phosphate (F6P) by an enzyme mentioned in (c) as described above.

As regards the enzymes and the microorganism recited in the above uses, the same applies as has been set forth above in connection with a method according to the invention, in particular as regards the preferred embodiments.

Figure 3:
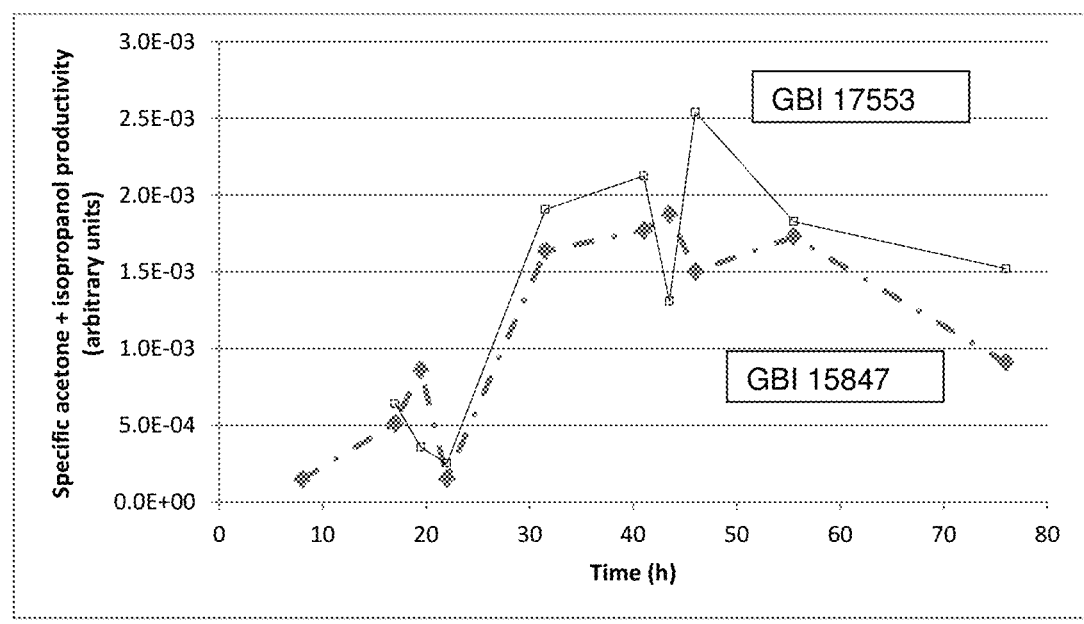

FIG. 3 shows the specific productivity of acetone and isopropanol for strains overexpressing the enzymes responsible for conversion of glyceraldehyde-3-phosphate (G3P) and dihydroxy-acetone phosphate (DHAP) into fructose-6-phosphate (F6P) (GBI 17553, solid line) and for strains which do not overexpress the enzymes responsible for conversion of glyceraldehyde-3-phosphate (G3P) and dihydroxy-acetone phosphate (DHAP) into fructose-6-phosphate (GBI 15847, dotted line).

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

General Methods and Materials

Procedure for ligations and transformations are well known in the art. Techniques suitable for use in the following examples may be found in Sambrook J., et al., Molecular Cloning: A Laboratory Manual, 2nd Edition, Cold Spring Harbor, N.Y., 1989, and Sambrook J., supra.

Materials and methods suitable for the maintenance and growth of bacterial cultures are well known in the art. Techniques suitable for use in the following examples may be found in Manual of Methods for General Bacteriology (Philipp Gerhardt, R. G. E. Murray, Ralph N. Costilow, Eugene W. Nester, Willis A. Wood, Noel R. Krieg and G. Briggs Philips, eds).

All reagents and materials used for the growth and maintenance of bacterial cells were obtained from Sigma-Aldrich Company (St. Louis, Mo.) unless otherwise specified.

Enzymes Overexpression and Purification.
a) Enzymes from *E. coli*
Plasmids from the ASKA collection have been used (Kitagawa, M et al. DNA Res. 12:291-299 (2005)) for overexpression of enzymes from *E. coli*.
Strain BL21(DE3) cells (Novagen) were cultivated in LB medium and were made electrocompetent. Electrocompetent BL21 cells were transformed with the corresponding plasmids for expression of the desired enzymes (see Table 1) and then plated on LB plates containing Chloramphenicol (25 ug/ml). Plates were incubated overnight at 30° C.
The transformed cells were grown with shaking (160 rpm) using ZYM-5052 auto-induction medium (Studier F W, Prot. Exp. Pur. 41:207-234 (2005)) for 20 h at 30° C. The cells were collected by centrifugation at 4° C., 4,000 rpm for 20 min and the pellets were stored at −80° C.

TABLE 1

Enzymes from *E. coli* overexpressed using plasmids from the ASKA collection and the corresponding coding sequence.

| Genes from *E. coli* for Enzymes overexpression | Nucleotide sequence | Protein encoded |
|---|---|---|
| fsaA | atgGAACTGTATCTGGATACTTCAGACGTTGTTGCGGTGAAGGCGC TGTCACGTATTTTTCCGCTGGCGGGTGTGACCACTAACCCAAGCAT TATCGCCGCGGGTAAAAAACCGCTGGATGTTGTGCTTCCGCAACTT CATGAAGCGATGGGCGGTCAGGGGCGTCTGTTTGCCCAGGTAATGG CTACCACTGCCGAAGGGATGGTTAATGACGCGCTTAAGCTGCGTTC TATTATTGCGGATATCGTGGTGAAAGTTCCGGTGACCGCCGAGGGG CTGGCAGCTATTAAGATGTTAAAAGCGGAAGGGATTCCGACGCTGG GAACCGCGGTATATGGCGCAGCACAAGGGCTGCTGTCGGCGCTGGC AGGTGCGGAATATGTTGCGCCTTACGTTAATCGTATTGATGCTCAG GGCGGTAGCGGCATTCAGACTGTGACCGACTTACACCAGTTATTGA AAATGCATGCGCCGCAGGCGAAAGTGCTGGCAGCGAGTTTCAAAAC CCCGCGTCAGGCGCTGGACTGCTTACTGGCAGGATGTGAATCAATT ACTCTGCCACTGGATGTGGCACAACAGATGATTAGCTATCCGGCGG TTGATGCCGCTGTGGCGAAGTTTGAGCAGGACTGGCAGGGAGCGTT TGGCAGAACGTCGATTtaa SEQ ID NO: 34 | SEQ ID NO: 8 Uniprot accession number P78055 |
| fsaA mutated A129S | ATGAGAGGATCTCACCATCACCATCACCATACGGATCCGGCCCTGA GGGCCGAACTGTATCTGGATACTTCAGACGTTGTTGCGGTGAAGGC GCTGTCACGTATTTTTCCGCTGGCGGGTGTGACCACTAACCCAAGC ATTATCGCCGCGGGTAAAAAACCGCTGGATGTTGTGCTTCCGCAAC TTCATGAAGCGATGGGCGGTCAGGGGCGTCTGTTTGCCCAGGTAAT GGCTACCACTGCCGAAGGGATGGTTAATGACGCGCTTAAGCTGCGT TCTATTATTGCGGATATCGTGGTGAAAGTTCCGGTGACCGCCGAGG GGCTGGCAGCTATTAAGATGTTAAAAGCGGAAGGGATTCCGACGCT GGGAACCGCGGTATATGGCGCAGCACAAGGGCTGCTGTCGGCGCTG GCAGGTGCGGAATATGTTagcCCTTACGTTAATCGTATTGATGCTC AGGGCGGTAGCGGCATTCAGACTGTGACCGACTTACACCAGTTATT GAAAATGCATGCGCCGCAGGCGAAAGTGCTGGCAGCGAGTTTCAAA ACCCCGCGTCAGGCGCTGGACTGCTTACTGGCAGGATGTGAATCAA TTACTCTGCCACTGGATGTGGCACAACAGATGATTAGCTATCCGGC GGTTGATGCCGCTGTGGCGAAGTTTGAGCAGGACTGGCAGGGAGCG TTTGGCAGAACGTCGATTGGCTATGCGGACGCTAA SEQ ID NO: 35 | SEQ ID NO: 9 |
| fsaB | atgGAACTGTATCTGGACACCGCTAACGTCGCAGAAGTCGAACGTC TGGCACGCATATTCCCCATTGCCGGGGTGACAACTAACCCGAGCAT TATCGCTGCCAGCAAGGAGTCCATATGGGAAGTGCTGCCGCGTCTG CAAAAAGCGATTGGTGATGAGGGCATTCTGTTTGCTCAGACCATGA GCCGCGACGCGCAGGGGATGGTGGAAGAAGCGAAGCGCCTGCGCGA CGCTATTCCGGGTATTGTGGTGAAAATCCCGGTGACTTCCGAAGGT CTGGCAGCAATTAAAATACTGAAAAAAGAGGGTATTACTACACTTG GCACTGCTGTATATAGCGCCGCACAAGGGTTATTAGCCGCACTGGC AGGGGCAAAATACGTTGCTCCGTATGTTAACGCGTAGATGCCCAG GGCGGAGACGGCATTCGTACGGTTCAGGAGCTGCAAACGCTGTTAG AAATGCACGCGCCAGAAAGCATGGTGCTGGCAGCCAGCTTTAAAAC GCCGCGTCAGGCGCTGGACTGTTTACTGGCAGGATGTGAATCCATC ACCCCTGCCCTTAGATGTAGCGCAACAAATGCTCAACACCCCTGCGG TAGAGTCAGCTATAGAGAAGTTCGAACACGACTGGAATGCCGCATT TGGCACTACTCATCTCtaa SEQ ID NO: 36 | SEQ ID NO: 16 Uniprot accession number P32669 |
| talB | atgACGGACAAATTGACCTCCCTTCGTCAGTACACCACCGTAGTGG CCGACACTGGGGACATCGCGGCAATGAAGCTGTATCAACCGCAGGA TGCCACAACCAACCCTTCTCTCATTCTTAACGCAGCGCAGATTCCG GAATACCGTAAGTTGATTGATGATGCTGTCGCCTGGGCGAAACAGC AGAGCAACGATCGCGCGCAGCAGATCGTGGACGCGACCGACAAACT GGCAGTAAATATTGGTCTGGAAATCCTGAAACTGGTTCCGGGCCGT ATCTCAACTGAAGTTGATGCGCGTCTTTCCTATGACACCGAAGCGT CAATTGCGAAAGCAAAACGCCTGATCAAACTCTACAACGATGCTGG TATTAGCAACGATCGTATTCTGATCAAACTGGCTTCTACCTGGCAG GGTATCCGTGCTGCAGAACAGCTGGAAAAAGAAGGCATCAACTGTA ACCTGACCCTGCTGTTCTCCTTCGCTCAGGCTCGTGCTTGTGCGGA AGCGGGCGTGTTCCTGATCTCGCCGTTTGTTGGCCGTATTCTTGAC TGGTACAAAGCGAATACCGATAAGAAAGAGTACGCTCCGGCAGAAG ATCCGGGCGTGGTTTCTGTATCTGAAATCTACCAGTACTACAAGGA GCACGGTTATGAAACCGTGGTTATGGGCGCAAGCTTCCGTAACATC GGCGAAATTCTGGAACTGGCAGGCTGCGACCGTCTGACCATCGCAC CGGCACTGCTGAAAGAGCTGGCGGAGAGCGAAGGGGCTATCGAACG TAAACTGTCTTACACCGGCGAAGTGAAAGCGCGTCCGGCGCGTATC ACTGAGTCCGAGTTCCTGTGGCAGCACAACCAGGATCCAATGGCAG TAGATAAACTGGCGGAAGGTATCCGTAAGTTTGCTATTGACCAGGA AAAACTGGAAAAAATGATCGGCGATCTGCTGtaa SEQ ID NO: 37 | SEQ ID NO: 17 Uniprot accession number P0A870 |

TABLE 1-continued

Enzymes from *E. coli* overexpressed using plasmids from the ASKA collection and the corresponding coding sequence.

| Genes from *E. coli* for Enzymes overexpression | Nucleotide sequence | Protein encoded |
|---|---|---|
| talB mutated F178Y | atgACGGACAAATTGACCTCCCTTCGTCAGTACACCACCGTAGTGG<br>CCGACACTGGGGACATCGCGGCAATGAAGCTGTATCAACCGCAGGA<br>TGCCACAACCAACCCTTCTCTCATTCTTAACGCAGCGCAGATTCCG<br>GAATACCGTAAGTTGATTGATGATGCTGTCGCCTGGGCGAAACAGC<br>AGAGCAACGATCGCGCGCAGCAGATCGTGGACGCGACCGACAAACT<br>GGCAGTAAATATTGGTCTGGAAATCCTGAAACTGGTTCCGGGCCGT<br>ATCTCAACTGAAGTTGATGCGCGTCTTTCCTATGACACCGAAGCGT<br>CAATTGCGAAAGCAAAACGCCTGATCAAACTCTACAACGATGCTGG<br>TATTAGCAACGATCGTATTCTGATCAAACTGGCTTCTACCTGGCAG<br>GGTATCCGTGCTGCAGAACAGCTGGAAAAAGAAGGCATCAACTGTA<br>ACCTGACCCTGCTGTTCTCCTTCGCTCAGGCTCGTGCTTGTGCGGA<br>AGCGGGCGTGTTCCTGATCTCGCCGTaTGTTGGCCGTATTCTTGAC<br>TGGTACAAAGCGAATACCGATAAGAAAGAGTACGCTCCGGCAGAAG<br>ATCCGGGCGTGGTTTCTGTATCTGAAATCTACCAGTACTACAAAGA<br>GCACGGTTATGAAACCGTGGTTATGGGCGCAAGCTTCCGTAACATC<br>GGCGAAATTCTGGAACTGGCAGGCTGCGACCGTCTGACCATCGCAC<br>CGGCACTGCTGAAAGAGCTGGCGGAGAGCGAAGGGGCTATCGAACG<br>TAAACTGTCTTACACCGGCGAAGTGAAAGCGCGTCCGGCGCGTATC<br>ACTGAGTCCGAGTTCCTGTGGCAGCACAACCAGGATCCAATGGCAG<br>TAGATAAACTGGCGGAAGGTATCCGTAAGTTTGCTATTGACCAGGA<br>AAAACTGGAAAAAATGATCGGCGATCTGCTGtaa<br>SEQ ID NO: 38 | SEQ ID NO: 64 |
| ybiV | atgAGCGTAAAAGTTATCGTCACAGACATGGACGGTACTTTTCTTA<br>ACGACGCCAAAACGTACAACCAACCACGTTTTATGGCGCAATATCA<br>GGAACTGAAAAAGCGCGGCATTAAGTTCGTTGTTGCCAGCGGTAAT<br>CAGTATTACCAGCTTATTTCATTCTTTCCTGAGCTAAAGGATGAGA<br>TCTCTTTTGTCGCGGAAAACGGCGCACTGGTTTACGAACATGGCAA<br>GCAGTTGTTCCACGGCGAACTGACCCGACATGAATCGCGGATTGTT<br>ATTGGCGAGTTGCTAAAAGATAAGCAACTCAATTTTGTCGCCTGCG<br>GTCTGCAAAGTGCATATGTCAGCGAAAATGCCCCCGAAGCATTTGT<br>CGCACTGATGGCAAAACACTACCATCGCCTGAAACCTGTAAAAGAT<br>TATCAGGAGATTGACGACGTACTGTTCAAGTTTTCGCTCAACCTGC<br>CGGATGAACAAATCCCGTTAGTGATCGACAAACTGCACGTAGCGCT<br>CGATGGCATTATGAAACCCGTTACCAGTGGTTTTGGCTTTATCGAC<br>CTGATTATTCCCGGTCTACATAAAGCAAACGGTATTTCGCGGTTAC<br>TGAAACGCTGGGATCTGTCACCGCAAAATGTGGTAGCGATTGGCGA<br>CAGCGGTAACGATGCGGAGATGCTGAAAATGGCGCGTTATTCCTTT<br>GCGGATGGGCAATGCTGCGGAAAACATTAAACAAATCGCCCGTTACG<br>CTACCGATGATAATAATCATGAAGGCGCGCTGAATGTGATTCAGGC<br>GGTGCTGGATAACACATCCCCTTTTAACAGCtga<br>SEQ ID NO: 39 | SEQ ID NO: 1<br>Uniprot accession number P75792 |
| yieH | atgTCCCGGATAGAAGCGGTATTTTTCGACTGCGACGGTACGCTGG<br>TCGACAGTGAAGTCATTTGCTCTCGCGCATATGTAACGATGTTTCA<br>GGAATTTGGTATTACGCTCGATCCTGAAGAGGTATTCAAACGTTTC<br>AAAGGTGTAAAACTGTACGAAATTATCGATATTGTTTCCCTTGAAC<br>ATGGTGTTACGTTAGCGAAAACAGAAGCTGAACACGTTTACCGTGC<br>AGAAGTCGCTCGGCTGTTCGATTCAGAACTGGAAGCCATCGAAGGG<br>GCTGGAGCGCTCCTGTCAGCGATCACTGCGCCAATGTGTGTGGTAT<br>CTAACGGCCCAAATAACAAAATGCAGCATTCTATGGGCAAGCTGAA<br>TATGTTGCACTACTTCCCGGATAAACTGTTCAGCGGCTACGATATT<br>CAGCGCTGGAAGCCAGACCCGGCGTTAATGTTCCATGCGGCAAAAG<br>CGATGAATGTAAATGTAGAAAACTGCATTCTGGTTGATGACTCAGT<br>TGCCGGTGCACAATCTGGTATCGACGCAGGTATGGAAGTGTTCTAC<br>TTCTGCGCCGACCCGCACAATAAGCCGATCGTTCACCCGAAAGTCA<br>CCACCTTTACCCATCTTTCGCAGTTACCTGAACTGTGGAAAGCGCG<br>TGGTTGGGATATTACGGCAtag SEQ ID NO: 40 | SEQ ID NO: 3<br>Uniprot accession number P31467 |
| yidA | atgGCTATTAAACTCATTGCTATCGATATGGATGGCACCCTTCTGC<br>TGCCCGATCACACCATTTCACCCGCCGTTAAAAATGCGATTGCCGC<br>AGCTCGCGCCCGTGGCGTGAATGTCGTGCTAACGACGGGTCGCCCG<br>TATGCAGGTGTGCACAACTACCTGAAAGAGCTGCATATGGAACAGC<br>CGGGCGACTACTGCATTACTTATAACGGCGCGCTGGTACAGAAGGC<br>CGCTGATGGTAGCACCGTGGCGCAAACTGCTCTCAGCTATGACGAC<br>TATCGTTTCCTGGAAAACTCTCTCGCGAAGTCGGTTCTCATTTCC<br>ACGCCCTGGACCGCACCACGCTGTACACCGCCAACCGTGATATCAG<br>CTACTACACGGTGCATGAATCTTCGTTGCCACCATTCCGCTGGTG<br>TTCTGCGAAGCGGAGAAAATGGACCCCAATACCCAGTTCCTGAAAG<br>TGATGATGATTGATGAACCCGCCATCCTCGACCAGGCTATCGCGCG<br>TATTCCGCAGGAAGTGAAAGAGAAATATACCGTGCTGAAAGTGCG<br>CCGTACTTCCTCGAAATCCTCGATAAACGCGTTAACAAAGGTACGG<br>GGGTGAAATCACTGGCCGACGTGTTAGGTATTAAACCGGAAGAAAT | SEQ ID NO: 2<br>Uniprot accession number P0A8Y5 |

TABLE 1-continued

Enzymes from *E. coli* overexpressed using plasmids from the ASKA collection and the corresponding coding sequence.

| Genes from *E. coli* for Enzymes overexpression | Nucleotide sequence | Protein encoded |
|---|---|---|
| | CATGGCGATTGGCGATCAGGAAAACGATATCGCAATGATTGAATAT GCAGGCGTCGGTGTGGCGATGGATAACGCTATTCCTTCAGTGAAAG AAGTGGCGAACTTTGTCACCAAATCTAACCTTGAAGATGGCGTGGC GTTTGCTATTGAGAAGTATGTGCTGAATtaa SEQ ID NO: 41 | |
| yigL | atgTACCAGGTTGTTGCGTCTGATTTAGATGGCACGTTACTTTCTC CGGACCATACGTTATCCCCTTACGCCAAAGAAACTCTGAAGCTGCT CACCGCGCGCGGCATCAACTTTGTGTTTGCGACCGGTCGTCACCAC GTTGATGTGGGGCAAATTCGCGATAATCTGGAGATTAAGTCTTACA TGATTACCTCCAATGGTGCGCGCGTTCACGATCTGGATGGTAATCT GATTTTTGCTCATAACCTGGATCGCGACATTGCCAGCGATCTGTTT GGCGTAGTCAACGACAATCCGGACATCATTACTAACGTTTATCGCG ACGACGAATGGTTTATGAATCGCCATCGCCCGGAAGAGATGCGCTT TTTTAAAGAAGCGGTGTTCCAATATGCGCTGTATGAGCCTGGATTA CTGGAGCCGGAAGGCGTCAGCAAAGTGTTCTTCACCTGCGATTCCC ATGAACAACTGCTGCCGCTGGAGCAGGCGATTAACGCTCGTTGGGG CGATCGCGTCAACGTCAGTTTCTCTACCTTAACCTGTCTGGAAGTG ATGGCGGGCGGCGTTTCAAAAGGCCATGCGCTGGAAGCGGTGGCGA AGAAACTGGGCTACAGCCTGAAGGATTGTATTGCGTTTGGTGACGG GATGAACGACGCCGAAATGCTGTCGATGGCGGGGAAAGGCTGCATT ATGGGCAGTGCGCACCAGCGTCTGAAAGACCTTCATCCCGAGCTGG AAGTGATTGGTACTAATGCCGACGACGCGGTGCCGCATTATCTGCG TAAACTCTATTTATCGtaa SEQ ID NO: 42 | SEQ ID NO: 4 Uniprot accession number P27848 |
| yqaB | atgTACGAGCGTTATGCAGGTTTAATTTTTGATATGGATGGCACAA TCCTGGATACGGAGCCTACGCACCGTAAAGCGTGGCGCGAAGTATT AGGGCACTACGGTCTTCAGTACGATATTCAGGCGATGATTGCGCTT AATGGATCGCCCACCTGGCGTATTGCTCAGGCAATTATTGAGCTGA ATCAGGCCGATCTCGACCCGCATGCGTTAGCGCGTGAAAAAACAGA AGCAGTAAGAAGTATGCTGCTGGATAGCGTCGAACCGCTTCCTCTT GTTGATGTGGTGAAAAGTTGGCATGGTCGTCGCCCAATGGCTGTAG GAACGGGGAGTGAAAGCGCCATCGCTGAGGCATTGCTGGCGCACCT GGGATTACGCCATTATTTTGACGCCGTCGTCGCTGCCGATCACGTC AAACACCATAAACCCGCGCCAGACACATTTTTGTTGTGCGCGCAGC GTATGGGCGTGCAACCGACGCAGTGTGTGGTCTTTGAAGATGCCGA TTTCGGTATTCAGGCGGCCCGTGCAGCAGGCATGGACGCCGTGGAT GTTCGCTTGCTGtga SEQ ID NO: 43 | SEQ ID NO: 5 Uniprot accession number P77475 |
| hxpA | gtgCGGTGCAAAGGTTTTCTGTTTGATCTTGATGGAACGCTGGTGG ATTCCCTGCCTGCGGTAGAACGGGCGTGGAGCAACTGGGCCAGACG TCATGGGTTAGCGCCGGAAGAGGTGCTGGCTTTCATTCACGGTAAA CAGGCGATCACCTCTCTGCGCCATTTTATGGCGGGCAAATCGAGG CTGATATTGCCGCCGAGTTTACGCGTCTGGAGCACATCGAGGCCAC GGAAACCGAAGGTATTACCGCGCTTCCGGGGGCAATCGCCTTACTC AGTCATTTGAATAAAGCAGGTATTCCGTGGGCCATTGTGACTTCTG GCTCCATGCCGGTAGCGCGAGCGCGCCATAAAATAGCTGGGCTTCC CGCACCAGAGGTGTTTGTAACCGCTGAGCGAGTGAAGCGCGGAAAA CCAGAACCTGATGCGTATCTGTTAGGCGCGCAGCTGCTGGGGCTTG CGCCGCAGGAGTGTGTGGTGGTGGAAGATGCTCCCGCTGGCGTGCT TTCTGGCCTGGCGGCGGGTTGTCATGTCATTGCGGTTAACGCTCCG GCAGATACCCCGCGCCTGAATGAGGTCGATTTGGTCCTCCACAGTC TGGAGCAAATTACTGTGACCAAACAGCCAAATGGCGATGTTATTAT TCAGtga SEQ ID NO: 44 | SEQ ID NO: 7 Uniprot accession number P77625 |
| hxpB | atgTCAACCCCGCGTCAGATTCTTGCTGCAATTTTTGATATGGATG GATTACTTATCGACTCAGAACCTTTATGGGATCGAGCCGAACTGGA TGTGATGGCAAGCCTGGGGGTGGATATCTCCCGTCGTAACGAGCTG CCGGACACCTTAGGTTTACGCATCGATATGGTGGTCGATCTTTGGT ACGCCCGGCAACCGTGGAATGGGCCAAGCCGTCAGGAAGTAGTAGA ACGGGTTATTGCCCGTGCCATTTCACTGGTTGAAGAGACACGTCCA TTATTACCAGGCGTGCGCGAAGCCGTTGCGTTATGCAAAGAACAAG GTTTATTGGTGGGACTGGCCTCCGCGTCACCACTACATATGCTGGA AAAAGTGTTGACCATGTTTGACTTACGCGACAGTTTCGATGCCCTC GCCTCGGCCGAAAAACTGCCTTACAGCAAGCCGCATCCGCAAGTAT ATCTCGACTGCGCAGCAAAACTGGGCGTTGACCCTCTGACCTGCGT AGCGCTGGAAGATTCGGTAAATGGCATGATCGCCTCTAAAGCAGCC CGCATGCGTTCCATCGTCGTTCCTGCGCCAGAAGCGCAAAATGATC CACGTTTTGTATTAGCAGACGTCAAACTTTCATCGCTGACAGAACT CACCGCAAAAGACCTTCTCGGTtaa SEQ ID NO: 45 | SEQ ID NO: 23 Uniprot accession number P77247 |

TABLE 1-continued

Enzymes from E. coli overexpressed using plasmids from the ASKA collection and the corresponding coding sequence.

| Genes from E. coli for Enzymes overexpression | Nucleotide sequence | Protein encoded |
|---|---|---|
| fbaA | atgTCTAAGATTTTTGATTTCGTAAAACCTGGCGTAATCACTGGTG<br>ATGACGTACAGAAAGTTTTCCAGGTAGCAAAAGAAAACAACTTCGC<br>ACTGCCAGCAGTAAACTGCGTCGGTACTGACTCCATCAACGCCGTA<br>CTGGAAACCGCTGCTAAAGTTAAAGCGCCGGTTATCGTTCAGTTCT<br>CCAACGGTGGTGCTTCCTTTATCGCTGGTAAAGGCGTGAAATCTGA<br>CGTTCCGCAGGGTGCTGCTATCCTGGGCGCGATCTCTGGTGCGCAT<br>CACGTTCACCAGATGGCTGAACATTATGGTGTTCCGGTTATCCTGC<br>ACACTGACCACTGCGCGAAGAAACTGCTGCCGTGGATCGACGGTCT<br>GTTGGACGCGGGTGAAAAACACTTCGCAGCTACCGGTAAGCCGCTG<br>TTCTCTTCTCACATGATCGACCTGTCTGAAGAATCTCTGCAAGAGA<br>ACATCGAAATCTGCTCTAAATACCTGGAGCGCATGTCCAAAATCGG<br>CATGACTCTGGAAATCGAACTGGGTTGCACCGGTGGTGAAGAAGAC<br>GGCGTGGACAACAGCCACATGGACGCTTCTGCACTGTACACCCAGC<br>CGGAAGACGTTGATTACGCATACACCGAACTGAGCAAAATCAGCCC<br>GCGTTTCACCATCGCAGCGTCCTTCGGTAACGTACACGGTGTTTAC<br>AAGCCGGGTAACGTGGTTCTGACTCCGACCATCCTGCGTGATTCTC<br>AGGAATATGTTTCCAAGAAACACAACCTGCCGCACAACAGCCTGAA<br>CTTCGTATTCCACGGTGGTTCCGGTTCTACTGCTCAGGAAATCAAA<br>GACTCCGTAAGCTACGGCGTAGTAAAAATGAACATCGATACCGATA<br>CCCAATGGGCAACCTGGGAAGGCGTTCTGAACTACTACAAAGCGAA<br>CGAAGCTTATCTGCAGGGTCAGCTGGGTAACCCGAAAGGCGAAGAT<br>CAGCCGAACAAGAAATACTACGATCCGCGCGTATGGCTGCGTGCCG<br>GTCAGACTTCGATGATCGCTCGTCTGGAGAAAGCATTCCAGGAACT<br>GAACGCGATCGACGTTCTGtaa SEQ ID NO: 46 | SEQ ID NO: 24<br>Uniprot accession number P0AB71 |
| fbaB | atgACAGATATTGCGCAGTTGCTTGGCAAAGACGCCGACAACCTTT<br>TACAGCACCGTTGTATGACAATTCCTTCTGACCAGCTTTATCTCCC<br>CGGACATGACTACGTAGACCGCGTAATGATTGACAATAATCGCCCG<br>CCAGCGGTGTTACGTAATATGCAGACGTTGTACAACACCGGGCGTC<br>TGGCTGGCACAGGATATCTTTCTATTCTGCCGGTTGACCAGGGCGT<br>TGAGCACTCTGCCGGAGCTTCATTTGCTGCTAACCCGCTCTACTTT<br>GACCCGAAAAACATTGTTGAACTGGCGATCGAAGCGGGCTGTAACT<br>GTGTGGCGTCAACTTACGGCGTGCTGGCGTCGGTATCGCGGCGTTA<br>TGCGCATCGCATTCCATTCCTCGTCAAACTTAATCACAACGAGACG<br>CTAAGTTACCCGAATACCTACGATCAAACGCTGTATGCCAGCGTGG<br>AGCAGGCGTTCAACATGGGCGCGGTTGCGGTTGGTGCGACTATCTA<br>TTTTGGCTCGGAAGAGTCACGTCGCCAGATTGAAGAAATTTCTGCG<br>GCTTTTGAACGTGCGCACGAGCTGGGTATGGTGACAGTGCTGTGGG<br>CCTATTTGCGTAACTCCGCCTTTAAGAAAGATGGCGTTGATTACCA<br>TGTTTCCGCCGACCTGACCGGTCAGGCAAACCATCTGGCGGCAACC<br>ATCGGTGCAGATATCGTCAAACAAAAAATGGCGGAAAATAACGGCG<br>GCTATAAAGCAATTAATTACGGTTACACCGACGATCGTGTTTACAG<br>CAAATTGACCAGCGAAAACCCGATTGATCTGGTGCGTTATCAGTTA<br>GCTAACTGCTATATGGGTCGGGCTGGGTTGATAAACTCCGGCGGTG<br>CTGCGGGCGGTGAAACTGACCTCAGCGATGCAGTGCGTACTGCGGT<br>TATCAACAAACGCGCAGGCGGAATGGGGCTGATTCTTGGACGTAAA<br>GCGTTCAAGAAATCGATGGCTGACGGCGTGAAACTGATTAACGCCG<br>TGCAGGACGTTTATCTCGATAGCAAAATTACTATCGCCtga<br>SEQ ID NO: 47 | SEQ ID NO: 25<br>Uniprot accession number P0A991 |

The expression of the recombinant enzymes was checked on a protein gel, after purification of the recombinant protein using a His trap (Protino Ni-IDA 1000 kit, Macherey Nagel). Purification was processed according to the manufacturer's recommendations.

b) Enzymes from Other Organisms than *E. coli*

The target genes (see Table 2) from several organisms were codon-optimized by GeneArt® (Invitrogen) for optimal expression in *Escherichia coli*. In addition, a His-tag was added at the 5' end of the gene and an additional stop codon was added at the 3' end. The gene construction is flanked by NdeI and EcoRI restriction sites and provided within plasmid pET25b+ (Merck-millipore).

Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41:207-234(2005)) for 20 h at 30° C. The cells were collected by centrifugation at 4° C., 4,000 rpm for 20 min and the pellets were stored at −80° C.

TABLE 2

Enzymes from several organisms and corresponding coding sequence (codon optimized for expression E. coli).

| Genes for Enzymes overexpression | Nucleotide sequence | Protein encoded |
|---|---|---|
| hdpA (from Corynebarium glutamicum (strain R)) | ATGCATCATCATCACCATCACATGACCGTGAATATTAG CTATCTGACCGATATGGATGGCGTGCTGATTAAAGAAG GTGAAATGATTCCGGGTGCCGATCGTTTTCTGCAAAGC CTGACAGATAATAACGTGGAATTTATGGTGCTGACCAA CAACAGCATTTTTACACCGCGTGATCTGAGCGCACGTC TGAAAACCAGCGGTCTGGATATTCCGCCTGAACGTATT TGGACCAGCGCAACCGCCACCGCACATTTTCTGAAAAG TCAGGTGAAAGAAGGCACCGCATACGTTGTTGGTGAAA GCGGTCTGACCACCGCACTGCATACCGCAGGTTGGATT CTGACAGATGCAAATCCGGAATTTGTTGTTCTGGGTGA AACCCGTACCTATAGCTTTGAAGCAATTACCACCGCCA TTAATCTGATTTTAGGTGGTGCACGTTTCATTTGTACC AATCCGGATGTTACCGGTCCGAGTCCGAGCGGTATTCT GCCTGCAACCGGTAGCGTTGCAGCACTGATTACCGCAG CAACCGGTGCAGAACCGTATTACATTGGTAAACCGAAT CCTGTGATGATGCGTAGCGCACTGAATACCATTGGTGC ACATAGCGAACATACCGTTATGATTGGTGATCGTATGG ATACCGATGTTAAAAGTGGTCTGGAAGCAGGTCTGAGT ACCGTTCTGGTTCGTAGCGGTATTTCAGATGATGCAGA AATTCGTCGTTATCCGTTTCGTCCGACACATGTGATTA ATAGCATTGCCGATCTGGCAGATTGTTGGGATGATCCG TTTGGTGATGGTGCATTTCATGTTCCGGATGAACAGCA GTTTACCGATTAA SEQ ID NO: 48 | SEQ ID NO: 6 Uniprot accession number A4QFW4 |
| LMRG_00181 (from Listeria monocytogenes serotype 1/2a (strain 10403S)) | ATGCATCTGGATAGCGCAAATCTGGATGACGTGAAAAA AATCCAGGCAAGCAGCATCTTTAAAGGCATTACCACCA ATCCGAGCATTCTGGTTAAAGAAAAATGTAATCGTCAG ACCGCCATTAACCGTATTCTGGAACTGACCGATAAACA GGTTTTTGTTCAGACCGTTGGCTTTACCTATGAAGAAA TTCTGGCAGATGCACGTATGCTGCTGACCATGTTTGGT AAAGACAAAATCGCAATCAAAATTCCGGCACATGAAGC AGGCACCAATGTTATTGATACCCTGAAAAAAGAGGACA AAACCATTCAGATTCTGGGCACCGCAATTTATAGCGCA GATCAGGCAATTACCGCAGCACTGGCAGGCGCAGATTT TGTTGCACCGTATGTTAATCGTATGAGCGCAGCAAATA TCGACCCGTTTAAAGAAATTACCCAGATGCGCCACTTC TTCGATAAAAAAGCACTGAAAACCCAGATTATGGCAGC CAGCTTTAAACATAGCGGTCAGGTTATGCAGGCCTATG AAAGCGGTGCAGATACCGTTACCATTCCGTATGAAATC TATAGCCAGATGACCAATAAAGTTCTGGCAGTTGAAGC CATTCGCGTGTTTAATGAAGATGCAGTTCTGTACGAGA AATGA SEQ ID NO: 49 | SEQ ID NO: 11 Uniprot accession number A0A0H3GHX1 |
| mipB (from Streptococcus pyogenes serotype M1) | ATGGAATATATGCTGGATACCCTGGATCTGGAAGCAAT CAAAAAATGGCATCACATTCTGCCGCTGGCAGGCGTTA CCAGCAATCCGAGCATTGCAAAAAAAGAAGGCGAGATC GATTTTTTTGAACGCATTCGTGAAGTGCGTGCCATTAT TGGTGATAAAGCAAGCATTCATGTTCAGGTTATTGCCC AGGATTATGAAGGCATTCTGAAAGATGCAGCAGAAATT CGTCGTCAGTGTGGTGATAGCGTTTATGTTAAAGTTCC GGTTACCACCGAAGGTCTGGCAGCAATTAAAACCCTGA AAGCAGAAGGTTATCATATTACCGCAACCGCAATTTAT ACCACCTTTCAGGGCCTGCTGGCAATTGAAGCCGGTGC AGATTATCTGGCTCCGTATTATAACCGTATGGAAATC TGAACATTGATCCGGAAGCAGTTATTGAACAGCTGGCC GAAGCAATTAATCGTGAAAATGCCAATAGCAAAATTCT GGCAGCCAGCTTTAAAAACGTTGCCCAGGTGAATAAAA GTTTTGCACTGGGTGCACAGGCAATTACCGCAGGTCCG GATGTTTTTGAAGCAGGTTTTGCCATGCCGAGCATTCA GAAAGCAGTTGATGATTTTGGTAAAGACTGGGAAGCAA TTCATCACCGCAAAAGCATCTGA SEQ ID NO: 50 | SEQ ID NO: 12 Uniprot accession number Q99XT4 |
| SGO_1787 (from Streptococcus gordonii) | ATGGAATTTATGCTGGATACCCTGAACCTGGAAGAAAT CAAAAAATGGTCAGAAGTTCTGCCGCTGGCAGGCGTTA CCAGCAATCCGACCATTGCAAAAAAAGAAGGCAAAATC GACTTTTTCGAACGCATTAGCGCAGTGCGTGAAATTAT TGGTGAAGGTCCGAGCATTCATGTTCAGGTTGTTGCAA AAGATTATGAGGGCATTCTGAAAGATGCAGCCACCATT CGTAAAAAATGTGGTGATGCCGTGTATATCAAAATTCC GGTTACACCGGATGGTCTGGCAGCAATTAAAACCCTGA AAGCAGAAGGCTATAAAATCACCGCAACCGCAATTTAT ACCACCTTTCAGGGCCTGCTGGCAATTGAAGCAGAAGC AGATTATCTGGCACCGTATTATAACCGTATGGAAATC TGAACATCGATTCCGATGCAGTTATTAGTCAGCTGGCA | SEQ ID NO: 10 Uniprot accession number A8AZ46 |

TABLE 2-continued

Enzymes from several organisms and corresponding coding sequence (codon optimized for expression E. coli).

| Genes for Enzymes overexpression | Nucleotide sequence | Protein encoded |
|---|---|---|
| | CAGGCCATTGAACGTGATCATAGCGATAGCAAAATTCT<br>GGCAGCCAGCTTTAAAAACGTTGCACAGGTTAATCGTG<br>CATTTGCAGATGGTGCACAGGCAGTTACCGCAGGTCCG<br>GATGTTTTTGCAGCAGCATTTGCAATGCCGAGTATTGC<br>AAAAGCAGTTGATGATTTTGCAACCGATTGGAGCGATA<br>TTCACAGCCAAGAATATGTGTGA SEQ ID NO: 51 | |
| UMC_00018<br>(from *Enterococcus faecalis* EnGen0302) | ATGGAATTTATGCTGGACACCATTAACCTGGAAGCCAT<br>TCGTAAATATCAGAAAATTCTGCCGCTGGCAGGCGTTA<br>CCAGCAATCCGAGCATTGTTAAACAGGCAGGCAAAATT<br>GATTTTTTTGCCCAGATGAAAGAAATCAAAAAGACCAT<br>TGGTCAGGCAAGCCTGCATGTTCAGGTTGTTGGTCAGA<br>CCACCGAAGAAATGCTGGAAGATGCACAGACCCATTGTG<br>CAGCAGCTGGGTCAAGAAACCTTTATCAAAATTCCGGT<br>TAATGAAGCAGGTCTGGCAGCAATTAAACAGCTGAAAC<br>AGGCAAATTATCGTATTACCGCAACCGCCATTTATACC<br>GAATTTCAGGGTTATCTGGCAATTGCAGCCGGTGCAGA<br>TTACCTGGCACCGTATTATAACCGTATGGAAAATCTGA<br>CCATCGACAGCCAGAAAGTTATTGAACATCTGGCAGCC<br>GAAATTAAACGTACCAATGCCAAAAGCAAAATTCTGGC<br>AGCGAGCTTTAAAAACGTTGCGCAGATTAATCAGGCAT<br>GTCAGATGGGTGCACAGGCAGTTACCATTGCACCGGAA<br>CTGGTTACCCAAGGTCTGGCCATGCCTGCAATTCAGAA<br>AGCAGTTACCGATTTTCAAGAAGATTGGGTTGCAGTTT<br>TTGGTGTGGAAACCGTTAATGAACTGGCCTGA<br>SEQ ID NO: 52 | SEQ ID NO: 18<br>Uniprot accession number A0A0M2AGL1 |
| tal<br>(from *Clostridium beijerinckii* (*Clostridium* MP)) | ATGCGCTTTTTTCTGGATACCGCCAACGTGGATCATAT<br>TAAAGAAGCAAATGAAATGGGCGTGATTTGTGGTGTTA<br>CCACCAATCCGAGCCTGGTTGCAAAAGAAGGTCGCGAT<br>TTTAACGAAGTGATCAAAGAAATTACCGAGATTGTGGA<br>TGGTCCGATTAGCGGTGAAGTTGTTGCCGAAGATGCAC<br>AGGGTATGATTAAAGAGGGACGCGAAATTGCAGCCATC<br>CATAAAAACATGATTGTGAAAATTCCGATGACCGCAGA<br>AGGTCTGAAAGCAACCAAAGTTCTGAGCAGCGAAGGTA<br>TTAAAACCAATGTGACCCTGATTTTTAGCGCAACCCAG<br>AGCCTGCTGGCAGCAAATGCCGGTGCAACCTATGTTAG<br>CCCGTTTCTGGGTCGTGTTGATGATATTAGCATGATTG<br>GTATGGATCTGGTTCGTGATATTGCCGAAATTTTTGCC<br>GTTCATGGTATCGAAACCGAAATCATTGCAGCAAGCGT<br>TCGTAATCCGATTCATGTTATTGAAGCAGCAAAAGCGG<br>GTGCCGATATTGCAACCATTCCGTATGCACTGGTTATG<br>CAGATGCTGAATCATCCGCTGACCGATCAAGGTCTGGA<br>AAAATTCAAAGCAGATTGGGCAGCAGCATTCGGCAAAT<br>GA SEQ ID NO: 53 | SEQ ID NO: 13<br>Uniprot accession number A0A0B5QQ90 |
| tal<br>(from *Caulobacter vibriodes* (strain ATCC 19089)) | ATGCAGATTTTTCTGGATAGCACCGACACCAAAGTTAT<br>TGCCGATCTGGCAAGCACCGGTCTGATTGATGGTGTTA<br>CCACCAATCCGACACTGATTGCAAAAAGCGGTCGTCCG<br>ATGCTGGAAGTGATTGCAGAAATTTGTGATATTGTTCC<br>GGGTCCGATTAGCGCAGAAGTTGCAGCAACCACCGCAG<br>ATGCAATGATTGCCGAAGGTCAGAAACTGGCAAAAATT<br>GCACCGAATGTTGTTGTGAAAATTCCGCTGACACGTGA<br>TGGCCTGATTGCATGTGCAGCATTTGCAGATGAAGAAA<br>TCAAAACCAATGTGACCCTGTGTTTTAGCCCGACACAG<br>GCACTGCTGGCAGCAAAAGCCGGTGCAACCTATATTAG<br>CCCGTTTATTGGTCGTCTGGATGATTATGGCTTTGATG<br>GTATGGATCTGATTCGTGATATTCGTGCCATCTATGAT<br>AACTATGGCTATGAAACCGAAATTCTGGCAGCCAGCGT<br>TCGTAATGCAGCACATGTTAAAGAAGCAGCAATTGTTG<br>GCGCAGATGTTGTTACCATTCCTCCGGCAGTTTTTAGC<br>GATCTGTATAAACATCCGCTGACCGATAAAGGTCTGGA<br>ACAGTTCCTGAAAGATTGGGCATCAACCGGTCAGAGCA<br>TTCTGTAA SEQ ID NO: 54 | SEQ ID NO: 14<br>Uniprot accession number Q9A2F1 |
| fsa_like<br>(from *Streptococcus suis*) | ATGGAATTTATGCTGGACACCCTGAACATTGAAGAAAT<br>TCGTAAATGGGCAGAAGTGCTGCCGCTGGCAGGCGTTA<br>CCAGCAATCCGACCATTGCACGTAAAGAAGGTGACATA<br>GATTTTTTTGAACGCCTGCATCTGATTCGCGATATTAT<br>TGGTCCGAATGCAAGCCTGCATGTTCAGGTTGTTGCAA<br>AAGATTATGAAGGTATTCTGGCCGACGCGAAAAAAATC<br>CGTGAACTGGCACCGGAAAACATCTATATCAAAGTTCC<br>GGTTACACCGGCAGGTCTGGCAGCAATGAAAACCCTGA<br>AGCACAGGGTTATCAGATTACCGCAACCGCAATTTAT | SEQ ID NO: 19<br>Uniprot accession number A0A0E4C393 |

TABLE 2-continued

Enzymes from several organisms and corresponding coding sequence (codon optimized for expression E. coli).

| Genes for Enzymes overexpression | Nucleotide sequence | Protein encoded |
|---|---|---|
| | ACCGTTTTTCAGGGTCTGCTGGCAATTGAAGCCGGTGC<br>AGATTATCTGGCTCCGTATTATAACCGTATGGCCAACC<br>TGAATATTGATAGCAATGCAGTTATTGCACAGCTGAGC<br>GAAGCAATTGATCGTGAATGTAGCGAAAGCAAAATTCT<br>GGCAGCCAGCTTTAAAAACGTTGATCAGGTTAATCAGG<br>CCTTTGCAAATGGTGCACAGGCAATTACCGCAGGCGCA<br>GATATTTTTGAAGCAGCATTTAGTATGCCGAGCATTGA<br>AAAAGCCGTTAACGATTTTGCAGATGATTGGAGCGCAA<br>TTCATGGTCGTTATACCATCTGA SEQ ID NO: 55 | |
| SMU_494<br>(from Streptococcus mutans serotype c (strain ATCC 700610) | ATGGAATTTATGCTGGATACCCTGAACCTGGCCGATAT<br>TGAAAAATGGGCAGCAATTCTGCCGCTGGCAGGCGTTA<br>CCAGCAATCCGAGCATTGCAAAAAAAGAAGGCAAAATC<br>GACTTCTTTGAACAGGTTAAACGTGTGCGTGCAATTAT<br>TGGTGAAGAACCGAGCATTCATGCACAGGTTGTTGCAG<br>CAGATGTTGAAGGTATTATCAAAGATGCCCACAAACTG<br>CAAGATGAATTAGGTGGTAATCTGTATGTTAAAGTTCC<br>GGTTAGCCCGACCGGTCTGACCGCAATGAAACAGCTGA<br>AAGAAGAAGGTTTTCAGATTACCGCAACCGCCATTTAT<br>ACCGTTTTTCAGGGTCTGCTGGCAATTGAAGCCGGTGC<br>AGATTATCTGGCTCCGTATTATAACCGTATGGAAAACC<br>TGAACATTGATCCGATTGAAGTTATTGGTCAGCTGGCA<br>CAGGCCATTGAATGTCAGCAGGCAAGCGCAAAAATTCT<br>GGCAGCCAGCTTTAAAAACGTTACCCAGGTTGCAAAAG<br>CACTGGCAGCCGGTGCCAAAGCAGTTACCGCAGGCGCA<br>GATATTTTTGCAGCAGGTTTTGCAAATCCGAGTATTCA<br>GAAAGCCGTTGATGATTTTGCAGCCGATTGGGAAAGCA<br>CCCAGGGTCGTCCGTATATCTAA SEQ ID NO: 56 | SEQ ID NO: 15<br>Uniprot accession number Q8DVJ4 |
| fsa_like<br>(from Streptococcus agalactiae serotype III (strain NEM316)) | ATGGAATTTCTGCTGGATACCCTGAATCTGGAAGCAAT<br>CAAAAAAATGGCATCACATTCTGCCGCTGGCAGGCGTTA<br>CCAGCAATCCGACCATTGCAAAAAAAGAAGGCGACATC<br>CATTTTTTTCAGCCATTCGTGATGTGCGCGAAATTAT<br>TGGTCGTGAAGCAAGCCTGCATGTTCAGGTTGTTGCAA<br>AAGATTATCAGGGCATTCTGGATGATGCAGCCAAAATT<br>CGTCAAGAAACCGATGATGACATCTACATTAAAGTTCC<br>GGTTACACCGGATGGTCTGGCAGCAATTAAAACCCTGA<br>AAGCAGAAGGTTATAACATTACCGCAACCGCCATTTAT<br>ACCAGTATGCAGGGTCTGCTGGCAATTAGTGCCGGTGC<br>AGATTATCTGGCTCCGTATTTTAACCGTATGGAAAACC<br>TGGATATTGATGCGACCCAGGTTATTAAAGAACTGGCA<br>CAGGCAATTGAACGTACCGGTAGCAGCAGCAAAATTCT<br>GGCAGCCAGCTTTAAAAACGCAAGCCAGGTTACCAAAG<br>CACTGAGCCAGGGTGCACAGAGTATTACCGCAGGTCCG<br>GATATTTTTGAAAGCGTTTTTGCCATGCCGAGCATTGC<br>CAAAGCAGTTAATGATTTTGCAGATGATTGGAAAGCCA<br>GCCAGCATAGCGAACATATCTAA SEQ ID NO: 57 | SEQ ID NO: 31<br>Uniprot accession number Q8E738 |
| fsaA<br>(from Streptococcus pneumoniae) | ATGGAATTTATGCTGGATACCCTGAACCTGGATGAAAT<br>CAAAAAAATGGTCAGAAATTCTGCCGCTGGCAGGCGTTA<br>CCAGCAATCCGACCATTGCAAAACGTGAAGGTAGCATC<br>AACTTTTTCGAACGCATTAAAGATGTGCGCGAACTGAT<br>TGGTAGCACCCCGAGCATTCATGTTCAGGTTATTAGCC<br>AGGATTTTGAGGGCATTCTGAAAGATGCACATAAAATT<br>CGTCGTCAAGCCGGTGATGACATCTTTATCAAAGTTCC<br>GGTTACACCGGCAGGTCTGCGTGCAATTAAAGCACTGA<br>AAAAAGAAGGCTATCATATTACCGCAACCGCCATTTAT<br>ACCGTTATTCAGGGTCTGCTGGCAATTGAAGCCGGTGC<br>AGATTATCTGGCTCCGTATTATAACCGTATGGAAAATC<br>TGAACATCGACAGCAATAGCGTTATTCGTCAGCTGGCA<br>CTGGCCATTGATCGTCAGAATAGCCCGAGCAAAATTCT<br>GGCAGCCAGCTTTAAAAACGTTGCCCAGGTTAATAATG<br>CACTGGCAGCGGGTGCACATGCAGTTACCGCAGGCGCA<br>GATGTTTTTGAAAGCGCATTTGCAATGCCGAGTATTCA<br>GAAAGCAGTGGATGATTTTTCCGATGATTGGTTTGTTA<br>CCCAGAATAGTCGCAGCATCTGA SEQ ID NO: 58 | SEQ ID NO: 20<br>Uniprot accession number A0A0D6J3Z8 |
| PH1655<br>(from Pyrococcus horikoshii (strain ATCC 700860)) | ATGCATCATCATCATCATCACATGGTGAAAGTGATCTT<br>TTTCGATCTGGATGATACCCTGGTTGATACCAGCAAAC<br>TGGCAGAAATTGCACGTAAAAATGCCATCGAAAAATATG<br>ATTCGTCATGGTCTGCCGGTTGATTTGAAACCGCATA<br>TAGTGAACTGATCGAGCTGATTAAAGAATACGGTAGCA<br>ACTTTCCGTATCACTTCGATTATCTGCTGCGTCGTCTG<br>GATCTGCCGTATAATCCGAAATGGATTAGTGCCGGTGT | SEQ ID NO: 21<br>Uniprot accession number O59346 |

TABLE 2-continued

Enzymes from several organisms and corresponding coding sequence (codon optimized for expression E. coli).

| Genes for Enzymes overexpression | Nucleotide sequence | Protein encoded |
|---|---|---|
| | TATCGCATATCACAATACCAAATTTGCCTATCTGCGTG<br>AAGTTCCGGGTGCGCGTAAAGTTCTGATTCGTCTGAAA<br>GAACTGGGTTATGAACTGGGCATTATTACCGATGGTAA<br>TCCGGTTAAACAGTGGGAAAAAATTCTGCGTCTGGAAC<br>TGGATGATTTTTTTGAACATGTGATCATCAGCGATTTC<br>GAGGGTGTTAAAAAACCGCATCCGAAAATCTTCAAAAA<br>AGCCCTGAAAGCCTTTAACGTGAAACCGGAAGAGGCAC<br>TGATGGTTGGTGATCGTCTGTATAGCGATATTTATGGT<br>GCAAAACGTGTGGGTATGAAAACCGTTTGGTTTCGCTA<br>TGGTAAACATAGTGAACGCGAACTGGAATATCGTAAAT<br>ATGCCGATTATGAGATCGACAATCTGGAAAGCCTGCTG<br>GAAGTTCTGGCACGTGAAAGCAGCAGCAACAAAAAAGT<br>TCATCCGCCTCGTCAGCAGATTTGA<br>SEQ ID NO: 59 | |
| MJ1437<br>(from *Methanocaldococcus*<br>*jannaschii* (strain ATCC<br>43067)) | ATGCATCATCATCACCATCACATGATTAAAGGCATCCT<br>GTTTGATCTGGATGATACCCTGTATAACAGCAGCGAAT<br>TTGTTGAAATTGCACGTCGTGAAGCAGTGAAAAGCATG<br>ATTGATGCAGGTCTGAACATCGATTTTGAAGAAGCCAT<br>GAACATCCTGAACAAGATCATCAAAGATAAGGGCAGCA<br>ACTATGGCAAACATTTCGATGATCTGGTTAAAGCCGTT<br>CTGGGTAAATATGATCCGAAAATTATCACCACCGGCAT<br>TATCACCTATCACAATGTGAAAGTTGCCACTGCTGCGTC<br>CGTATCCGCATACCATTAAAACCCTGATGGAACTGAAA<br>GCAATGGGTCTGAAACTGGGTGTTATTACCGATGGTCT<br>GACCATTAAACAGTGGGAAAAACTGATTCGTCTGGGCA<br>TTCATCCGTTTTTTGATGATGTGATTACCAGCGAAGAA<br>TTTGGTCTGGGCAAACCGCATCTGGAATTTTTCAAATA<br>TGGCCTGAAACGTATGGGCCTGAAAGCCGAAGAAACCG<br>TTTATGTTGGTGATCGTGTGGACAAAGATATTAAGCCT<br>GCAAAAGAACTGGGCATGATTACCGTTCGTATTCTGAA<br>AGGCAAATACAAAGACATGGAAGATGATGAGTATAGCG<br>ACTACACCATTAATAGCCTGCAAGAGCTGGTTGACATT<br>GTGAAAAACCTGAAAAAGGATTAA<br>SEQ ID NO: 60 | SEQ ID NO: 22<br>Uniprot accession<br>number Q58832 |
| ALDOB<br>(from *Homo sapiens*<br>(Human)) | ATGCATCATCATCACCATCACATGGCACATCGTTTTCC<br>GGCACTGACCCAAGAACAGAAAAAAGAACTGAGCGAAA<br>TTGCCCAGAGCATTGTTGCAAATGGTAAAGGTATTCTG<br>GCAGCAGATGAAAGCGTTGGTACAATGGGTAATCGTCT<br>GCAACGTATTAAAGTGGAAAACACCGAAGAAAATCGTC<br>GTCAGTTTCGTGAAATTCTGTTTAGCGTTGATAGCAGC<br>ATTAATCAGAGTATTGGTGGCGTGATTCTGTTCCATGA<br>AACCCTGTATCAGAAAGATAGCCAGGGTAAACTGTTTC<br>GCAACATCCTGAAAGAAAAAGGTATTGTGGTGGGCATC<br>AAACTGGATCAAGGTGGTGCACCGCTGGCAGGCACCAA<br>TAAAGAAACCACCATTCAAGGTCTGGATGGTCTGAGCG<br>AACGTTGTGCACAGTACAAAAAAGATGGTGTGGATTTT<br>GGTAAATGGCGTGCAGTTCTGCGTATTGCAGATCAGTG<br>TCCGAGCAGCCTGGCAATTCAAGAAATGCAAATGCAC<br>TGGCACGTTATGCAAGCATTTGTCAGCAGAATGGTCTG<br>GTTCCGATTGTTGAACCGGAAGTTATTCCGGATGGTGA<br>CCATGATCTGGAACATTGTCAGTATGTTACCGAAAAAG<br>TGCTGGCAGCCGTTTATAAAGCACTGAATGATCATCAT<br>GTTTACCTGGAAGGCACCCTGCTGAAACCGAATATGGT<br>TACCGCAGGTCATGCATGTACCAAAAAATACACACCGG<br>AACAGGTTGCAATGGCAACCGTTACCGCACTGCATCGT<br>ACCGTTCCGGCAGCAGTTCCGGGTATTTGTTTTCTGAG<br>CGGTGGTATGAGCGAAGAAGATGCAACCCTGAATCTGA<br>ATGCAATTAATCTGTGTCCGCTGCCGAAACCGTGGAAA<br>CTGAGCTTTAGCTATGGTCGTGCACTGCAAGCAAGCGC<br>ACTGGCAGCATGGGGTGGTAAAGCAGCAAATAAAGAAG<br>CAACCCAAGAGGCCTTTATGAAACGTGCAATGGCCAAT<br>TGTCAGGCAGCAAAAGGCCAGTATGTTCATACCGGTAG<br>CAGCGGTGCCGCAAGCACCCAGAGCCTGTTTACCGCAT<br>GTTATACCTATTGA SEQ ID NO: 61 | SEQ ID NO: 26<br>Uniprot accession<br>number P05062 |
| pgm<br>(from *Aeromonas*<br>*hydrophila* subsp.<br>*hydrophila* (strain ATCC<br>7966)) | ATGGCACAGCATAGCCATGCAGGTCAGCCTGCACGTCT<br>GAGCGATCTGACCAATATTCCGCGTCTGGTTAGCGCAT<br>ATTATCTGAATAAACCGGATATGAGCCGTCCGGAACAG<br>CGTGTTGCATTTGGCACCAGCGGTCATCGTGGTAGCGC<br>ACTGCATAATGCATTTACCGAAAGCCATATTCTGGCAG<br>TTACCCAGGCACTGGTTGAATATCGTCAGCAGGCAGGT<br>ATTACCGGTCCGCTGTTTGTTGGTATGGATACCCATGC | SEQ ID NO: 29<br>Uniprot accession<br>number A0KIH4 |

TABLE 2-continued

Enzymes from several organisms and corresponding coding
sequence (codon optimized for expression E. coli).

| Genes for Enzymes overexpression | Nucleotide sequence | Protein encoded |
|---|---|---|
| | ACTGAGCGAAAGCGCATTTGCAAGCGCAGTTGAAGTTC<br>TGGCAGCAAATGGTGTTGAAACCCGTATTCAGGCAGGT<br>CTGGGTTTTACCCCGACACCGGTTATTAGCCATGCCAT<br>TCTGCGTCATAATGCAGGTAAACCGGCAGCACGTGCAG<br>ATGGTGTTGTTATTACCCCGAGCCATAATCCGCCTGAA<br>GATGGTGGCTTTAAATACAATCCGCCTCATGGTGGTCC<br>TGCCGAAGGTGAAATTACAAAATGGGTTGAAGATCGTG<br>CCAATGCAATTCTGGAAGCCGGTCTGGCAGGCGTTAAA<br>CGTATGGCATTTGCAGAAGCACTGAAAAGCCCGTTTGT<br>TGCACTGCATGATTATGTTACCCCGTATGTTGATGATC<br>TGAAAAACGTTCTGGATATGGATGCCATTAAACAGGCA<br>GGCATTAAAATCGGTGTTGATCCGTTAGGTGGTAGCGG<br>TGTTGCCTATTGGGATGTTATTGCAAAAACCTATGGCC<br>TGAATATCGAGGTGGTGAACTATAAAGTTGATCCGACC<br>TTTAGCTTTATGACCCTGGATAAAGATGGCAAAATTCG<br>TATGGATTGTAGCAGTCCGTTTGCAATGGCAAGCCTGA<br>TTGCACTGAAAGACAAATTTGATATTGCGCTGGGTAAC<br>GATCCGGATTATGATCGTCATGGTATTGTTACCAAAAG<br>CGGTCTGATGAATCCGAATCATTATCTGGCCGTTGCAA<br>TTCAGTACCTGTTTACCCATCGTACCGGTTGGAGCAAA<br>GAAAGCGCTGTTGGCAAAACCCTGGTTAGCAGCAGCAT<br>GATTGATCGTGTTGCCGGTGAAATTGGTCGTACCCTGA<br>AAGAAGTTCCGGTTGGTTTTAAATGGTTTGTGGATGGT<br>CTGTATAGCGGTGAATTTGGTTTTGGTGGTGAAGAAAG<br>TGCCGGTGCCAGCTTTCTGCGTAAAGATGGTACAGTTT<br>GGACCACCGATAAAGACGGTTTTATTCTGGCCCTGCTG<br>GCAGCAGAAATTCTGGCCGTGACCGGTAAAGATCCGCA<br>GACACATTATGATGCACTGGAAGCAAAATTTGGTCGTA<br>GCAGCTATCGTCGTATTGATGCACCGGCAAATAGCGCA<br>CAGAAAGCAGTTCTGAGCAAATTAGATCCGGCACTGGT<br>GGAAGCAAGCACCTTAGCCGGTGAACCGATTATTGCCA<br>AACTGACCAAAGCACCGGGTAATGATCAGCAATTGGT<br>GGTCTGAAAGTTGTTACCGAAAATGGTTGGTTTGCAGC<br>ACGTCCGAGCGGCACCGAAAGCATCTATAAAATCTATA<br>TGGAATCCTTCAAAGGCGAAGCACATCTGGATCTGATT<br>CAGCAAGAAGCACAGCAGATTGTTAGCGCAGCACTGGC<br>AAAAGCCGGTGTTTAATAA SEQ ID NO: 62 | |
| AHA_2903<br>(from Aeromonas<br>hydrophila subsp.<br>hydrophila (strain ATCC<br>7966)) | ATGAATCTGACCTGTTTCAAAGCCTATGACATTCGTGG<br>TAAACTGGGTGATGAACTGAATATCGAAATTGCCTATC<br>GTATTGGTCGTGCAACCGCACAGTATCTGAAAGCAACC<br>CGTATTGCAGTTGGTGGTGATGTTCGTCTGACCAGCGA<br>AGGTCTGAAACAGGCACTGGCAAATGGTATTCTGGATG<br>CAGGTTGTGATGTTATTGATCTGGGTGTTACCGGCACC<br>GAAGAAACCTATTTCGCAGCATTTACCCTGGATATTGA<br>TGGTGCAATTGAAGTTACCGCAAGCCATAATCCGATGG<br>ATTACAATGGTATGAAACTGGTTGGTCGTGATGCATGT<br>CCGATTAGCGGTGATAGCGGTCTGAATGATATTCGTGC<br>ACTGGCAGAAAAAGGTGATTTTAGCGTTAGCTTTCGTC<br>GTGGCACCCTGAGCAAAAAAAGCATCCTGGATGCCTAT<br>GTTGATCATCTGCTGACCTATATCAAACCGCATCAGCT<br>GCGTCCGCTGAAATTAGTTGTTAATGCAGGTAATGGTG<br>CAGCCGGTCATGTTATCGATGTGATTGAACAGCGTTTT<br>AACATTCTGAACATCCCGGTGGAATTTATCAAAATCCA<br>TCATGAAGAAAACGGCAACTTTCCGAATGGCATTCCGA<br>ATCCGCTGCTGCCGGAAAATCGTGATGTTACCAGTGAA<br>GCAGTTAAACTGCATCATGCAGATATGGGTATTGCATG<br>GGATGGTGATTTTGATCGCTGTTTTCTGTTTGATGAGA<br>ACGGCATTTTTATCGAGGGCTATTATATCGTTGGTCTG<br>CTGGCAGAAGCATTTCTGGTTGAAAATCCGCATGAACG<br>CATTATTCATGATCCGCGTCTGACCTGGAATACCATCG<br>ATATTGTTGAAAAAGCGGTGGTATTCCGGTTCAGTCA<br>AAAACCGGTCATGCCTTTATCAAAGAACGTATGCGTAG<br>CGAAAATGCCATTTATGGTGGTGAAATGAGCGCACATC<br>ATTATTTTCGCGATTTTGGTTATTGCGATAGCGGTATG<br>ATTCCGTGGCTGCTGGTTATTAATCTGCTGAGCCTGAA<br>AAATAGCACCCTGTCAAGCCTGGTTGCAGAACGTGTTA<br>AAGCATATCCGTGTAGCGGTGAAATTAACTATCGTGTT<br>GATAACGCCCTGGAAATCATCAAAAAACTGGAAGAGGT<br>TTATGTTCCGCTGGCCGTTAAAGTTGAATATGTTGATG<br>GTCTGAGCATCGAGATGAATGATTGGCGTTTTAATGTG<br>CGCATTAGCAATACAGAACCTCTGCTGCGTCTGAATGT | SEQ ID NO: 30<br>Uniprot accession<br>number A0KMA6 |

TABLE 2-continued

Enzymes from several organisms and corresponding coding sequence (codon optimized for expression E. coli).

| Genes for Enzymes overexpression | Nucleotide sequence | Protein encoded |
|---|---|---|
| | TGAAAGCAAAAACAACATTAGCAAACTGACCAGTGGTC TGAATAGCCTGCATAAGATGATTAACAACATCTAA SEQ ID NO: 63 | |

The expression of the recombinant enzymes was checked on a protein gel, after purification of the recombinant protein using a His trap (Protino Ni-IDA 1000 kit, Macherey Nagel). Purification was processed according to the manufacturer's recommendations.

Example 1: Fructose-6-Phosphate Aldolase and Fructose Bisphosphatase Activity Inhibition Tests A series of tests was conducted in order to determine if AMP has an inhibitory effect on the enzymatic activity of fructose-6-phosphate aldolase and/or fructose bisphosphatase. The protocol used to test the enzymatic activities was adapted from C. Guérard-Hélaine, V. De Berardinis, M. Besnard-Gonnet, E. Darii, M. Debacker, et al. Genome Mining for Innovative Biocatalysts: New Dihydroxyacetone Aldolases for the Chemist's Toolbox. *Chem Cat Chem*, Wiley, 7:1871-1879 (2015).

a) Impact of AMP Concentration on Fructose Bisphosphatase Activity

Figure 1:
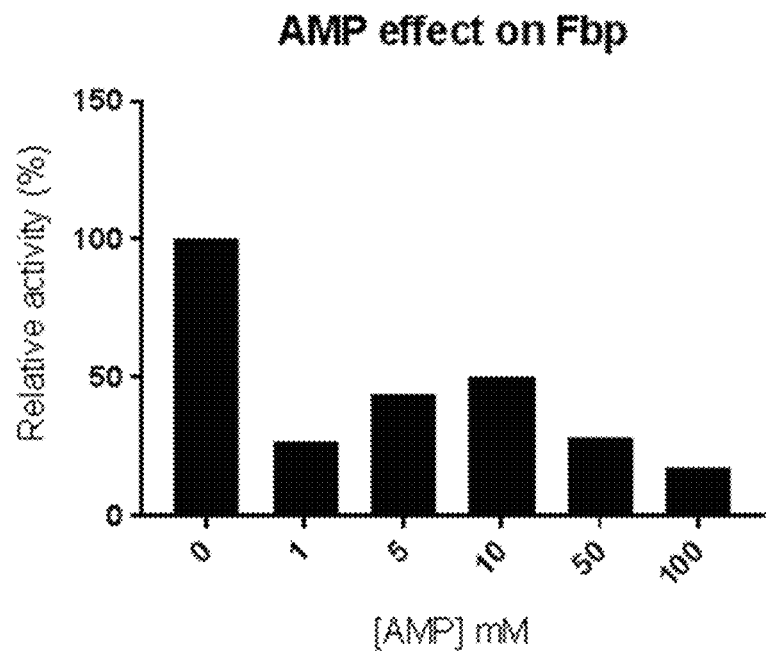
FIG. 1 shows the impact of the AMP concentration on fructose bisphosphatase activity.

120 µl of each kinetic assay contained Tris HCl buffer (50 mM; pH 7.5), 20 mM NaCl, 10 mM MgCl2, 1 mM NADP+, AMP (several concentrations tested), 1 mM Fructose 1,6-bisphosphate (F1,6bisP), 0.2 mg/ml FBP enzyme, and the auxiliary enzymes (glucose-6-phosphate isomerase (PGI) and NADP$^+$-dependent glucose-6-phosphate dehydrogenase (zwf) (0.5 mg/ml each)). The mix was incubated at 30° C. for up to 20 minutes and the reaction was monitored by spectrophotometry at 340 nm (measuring NADPH formation), assuming that 1 reduced NADPH molecule was produced per Fructose-6-Phosphate molecule. Results are shown in FIG. 1. A strong inhibitory impact of AMP on fructose bisphosphatase activity was observed.

b) Impact of AMP Concentration on Fructose-6-Phosphate Aldolase Activity of FsaA A129S 120 µl of each kinetic assay contained Tris HCl buffer (50 mM; pH 8.5), 1 mM NADP+, AMP (several concentrations tested), 200 mM DHA, 3 mM D,L-G3P, 0.4 mg/ml FsaA A129S, and the auxiliary enzymes (glucose-6-phosphate isomerase (PGI) and NADP$^+$-dependent glucose-6-phosphate dehydrogenase (zwf) (0.5 mg/ml each)).

Figure 2:
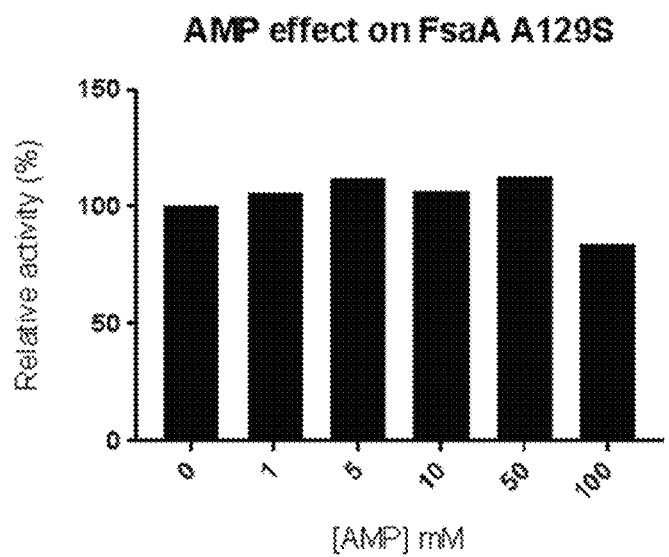
FIG. 2 shows the impact of the AMP concentration on Fsa A129S.

The mix was incubated at 30° C. for up to 20 minutes and the reaction was monitored by spectrophotometry at 340 nm (measuring to NADPH formation), assuming that 1 reduced NADPH molecule was produced per Fructose-6-Phosphate molecule. Results are shown in FIG. 2. No inhibitory effect of AMP could be observed with FSAA A129S.

Example 2: In Vitro Conversion of Glyceraldehyde-3-Phosphate (G3P) and Dihydroxy-Acetone Phosphate (DHAP) into Fructose-6-Phosphate (F6P) Through a Dihydroxy-Acetone (DHA) Intermediate A series of tests were conducted in order to determine the best enzyme combinations to convert G3P and DHAP into F6P. These enzyme combinations should perform the 2 steps:
1) DHAP→DHA
2) DHA+G3P→F6P a) Enzyme Catalyzing the Conversion of DHA and G3P into F6P The protocol used to test the enzymatic activities was adapted from C. Guérard-Hélaine, V. De Berardinis, M. Besnard-Gonnet, E. Darii, M. Debacker, et al., Genome Mining for Innovative Biocatalysts: New Dihydroxyacetone Aldolases for the Chemist's Toolbox. *Chem Cat Chem*, Wiley, 7:1871-1879 (2015).

120 µl of each kinetic assay contained Tris HCl buffer (50 mM pH 8.5), 3 mM D,L-G3P, 200 mM DHA, 1 mM NADP+, 0.4 mg/ml of enzyme, and the auxiliary enzymes (glucose-6-phosphate isomerase (PGI) and NADP$^+$-dependent glucose-6-phosphate dehydrogenase (zwf) (0.5 mg/ml each)). The mix was incubated at 30° C. and the reaction was monitored by spectrophotometry at 340 nm (measuring NADPH formation), assuming that 1 reduced NADPH molecule was produced per F6P molecule. Results are shown in Table 3.

TABLE 3

Production of F6P from DHA and G3P, with different enzymes

| Gene coding for the enzyme | SEQ ID NO | Uniprot number | Activity |
|---|---|---|---|
| LMRG_00181 | 49 | A0A0H3GHX1 | ++++ |
| mipB | 50 | Q99XT4 | ++++ |
| SGO_1787 | 51 | A8AZ46 | ++++ |
| fsaA A129S | 35 | — | +++ |
| fsa-like | 57 | Q8E738 | +++ |
| UMC_00018 | 52 | A0A0M2AGL1 | ++ |
| SMU_494 | 56 | Q8DVJ4 | ++ |
| fsa-like | 55 | A0A0E4C393 | ++ |
| fsa | 58 | A0A0D6J3Z8 | ++ |
| fsaB | 36 | P32669 | ++ |
| talB F178Y | 38 | — | ++ |
| tal | 53 | A0A0B5QQ90 | + |
| tal | 54 | Q9A2F1 | + |
| Control (no substrate) | | | − |
| Control (no enzyme) | | | − | a) Enzyme Catalyzing the Conversion of DHAP into DHA

The protocol used to test the enzymatic activities was adapted from C. Guérard-Hélaine, V. De Berardinis, M. Besnard-Gonnet, E. Darii, M. Debacker, et al., Genome Mining for Innovative Biocatalysts: New Dihydroxyacetone Aldolases for the Chemist's Toolbox. *Chem Cat Chem*, Wiley, 7:1871-1879 (2015)).

120 µl of each kinetic assay contained Tris HCl buffer (50 mM pH 8.5), 10 mM MgCl2, 100 mM DHAP, 0.8 mM NADP+, 0.6 mg/ml of enzyme, 0.8 mg/ml fructose-6-phosphate aldolase 1 from *E. coli* MG1655 (FSAA mutated A129S) and the auxiliary enzymes (glucose-6-phosphate isomerase (PGI) and NADP+-dependent glucose-6-phosphate dehydrogenase (zwf) (0.5 mg/ml each)). The mix was incubated at 30° C. and the reaction was monitored by spectrophotometry at 340 nm (measuring NADPH formation), assuming that 1 reduced NADPH molecule was produced per F6P molecule. Results are shown in Table 3.

TABLE 4

Production of DHA from DHAP with different enzymes

| Gene coding for the enzyme | SEQ ID NO | Uniprot Number | Activity |
|---|---|---|---|
| ybiV | 39 | P75792 | +++ |
| yieH | 40 | P31467 | +++ |
| yidA | 41 | P0A8Y5 | ++ |
| yigL | 42 | P27848 | ++ |
| yqaB | 43 | P77475 | + |
| hdpA | 48 | A4QFW4 | + |
| hxpA | 44 | P77625 | + |
| Control (no substrate) | | | − |
| Control (no enzyme) | | | − |

Example 3: In Vitro Conversion of Glyceraldehyde-3-Phosphate (G3P) and Dihydroxy-Acetone-Phosphate (DHAP) into Fructose-6-Phosphate (F6P) Through a Glyceraldehyde Intermediate A series of tests were conducted in order to determine the best enzyme combinations to convert G3P and DHAP into F6P. The best enzymes combination should perform the 3 steps:
1) G3P→Glyceraldehyde
2) Glyceraldehyde+DHAP→F1P
3) F1P→F6P a) Enzymes Catalyzing the Conversion of G3P into Glyceraldehyde 200 µl of each kinetic assay contained Tris HCl buffer (50 mM pH 7.5), 100 mM NaCl, 10 mM MgCl2, G3P (1-10-50 mM) and 2 mg/ml of the tested enzyme (see table 7). The mix was incubated overnight at 30° C. and the reaction was quenched with 1 volume acetonitrile. The final products were analysed by LCMS. LC-MS analyses were performed on an Ultimate 3000 (Dionex, Thermo Fisher Scientific) coupled to a Q-Orbitrap mass spectrometer (Thermo Fisher Scientific) fitted with an electrospray (ESI) source and operating in negative ion mode. The chromatographic separations were performed using a HILIC amide (1.9 µm, 2.1×150 mm) column maintained at 25° C. (Waters) operated under gradient elution, as follows. Mobile phases were: (A) 10 mM ammonium formiate pH 9.45 (adjusted with ammonium hydroxide), while mobile phase (B) was 100% acetonitrile and the flow rate was 500 µL/min. Elution started with an isocratic step of 1.5 min at 95% B, followed by a linear gradient from 95 to 55% of phase B in 7 min. The chromatographic system was then rinsed for 2 min at 55% B, and the run was ended with an equilibration step of 8.5 min.

TABLE 5

Enzymes catalysing the conversion of G3P into glyceraldehyde.

| Gene coding for the enzyme | SEQ ID NO | Uniprot Number | Activity |
|---|---|---|---|
| PH1655 | 59 | O59346 | − |
| MJ1437 | 60 | Q58832 | − |
| hxpB | 45 | P77247 | + |
| Control (no substrat) | | | − |
| Control (no enzyme) | | | − | a) Enzymes Catalyzing the Conversion of Glyceraldehyde and DHAP into F1P, and the Further Conversion of F1P into F6P 200 µl of each kinetic assay contained Tris HCl buffer (50 mM pH 7.5), 50 mM NaCl, 5 mM MgCl$_2$, 1 mM NADP+, 10 mM DHAP, 10 mM Glyceraldehyde, 1 mg/ml AldoB, 1 mg/ml PGM and PMM and the auxiliary enzymes (glucose-6-phosphate isomerase (PGI) and NADP+-dependent glucose-6-phosphate dehydrogenase (zwf) (1 mg/ml each)). The mix was incubated at 30° C. and the reaction was monitored by spectrophotometry at 340 nm (measuring NADPH formation), assuming that 1 reduced NADPH molecule was produced per F6P molecule. Results are shown in Table 6.

TABLE 6

Enzymes catalyzing the conversion of glyceraldehyde and DHAP into F1P and the further conversion of F1P into F6P. The enzyme encoded by ALDOB was incubated together with the enzymes encoded by pgm (assay 1), with the enzymes encoded by AHA_2903 (assay 2) or with both (assay 3).

| Assay | Genes | SEQ ID NO | Uniprot Number | Activity |
|---|---|---|---|---|
| 1 | ALDOB | 61 | P05062 | + |
|   | pgm | 62 | A0KIH4 | |
| 2 | ALDOB | 61 | P05062 | + |
|   | AHA_2903 | 63 | A0KMA6 | |
| 3 | ALDOB | 61 | P05062 | ++ |
|   | pgm | 62 | A0KIH4 | |
|   | AHA_2903 | 63 | A0KMA6 | |
| 4 | Control (no substrate) | | | − |
| 5 | Control (no enzyme) | | | − |

Example 4: Construction of a New *E. coli* Chassis for the Production of Acetone and Isopropanol Like most organisms, *E. coli* converts glucose to acetyl-CoA. A modified *E. coli* chassis in which the yield of acetyl-CoA production is optimized has been described previously (WO 2013/007786). A bacterial chassis, strain A, was constructed with the following genotype:

MG1655 ΔptsHI Δzwf_edd_eda ΔpfkA ΔpfkB

Plasmid-based overexpression of a PKT gene from phosphoketolase YP 003354041.1 from *Lactococcus lactis* into strain A resulted in strain B, a strain with a rewired central carbon metabolism, wherein a new phosphoketolase-based carbon catabolic pathway replaced the inactivated Embden-Meyerhoff-Parnas pathway (EMPP), the pentose phosphate pathway (PPP), and the Entner Doudoroff pathway (EDP). Upon introduction of an acetone pathway into strain B, superior acetone yields were observed, as compared with wild type MG1655 strain expressing the same acetone pathway.

In order to construct a strain having a PKT pathway and capable of robust growth on sucrose as carbon source, strain A was further engineered as described below.

A PKT gene was introduced into the chromosome of strain A, at the kdgk locus (kdgK::P1_RBST7_pkt). The resulting strain had the following genotype:

MG1655 ΔptsHI Δzwf_edd_eda ΔpfkA ΔpfkB kdgK::P1_RBST7_pkt

This strain was passaged for several months on minimal medium supplemented with glucose as the carbon source, while continuously selecting for clones or populations having the highest growth rate, until a doubling time of less than 5 hours was reached.

Several gene deletions were performed in order to increase acetone and isopropanol production: Δhem A ΔfsaA ΔfsaB.

To further increase isopropanol production, pntAB (pyridine nucleotide transhydrogenase subunits alpha and beta, Uniprot P07001 and P0AB67, NCBI Reference Sequences: NP_416120.1 and NP_416119.1) genes from *E. coli* were overexpressed by inserting a strong constitutive promotor at the pntAB locus.

The resulting strain is referred to as strain C hereafter.

Example 5: Construction of *E. coli* Strains for the Production of Acetone and Isopropanol from Acetyl-CoA This working example shows the production of acetone and isopropanol by recombinant *E. coli* strains, expressing the genes constituting the acetone and isopropanol pathway.

The enzymes used in this study to convert acetyl-CoA into acetone and isopropanol are listed in Table 7.

Expression of Acetone/Isopropanol Biosynthetic Pathway in *E. coli*.

Strain C as described in Example 4 was used as a host microorganism.

All the listed genes were codon optimized for expression in *E. coli* and synthesized either by GeneArt® (Thermofisher), except the genes atoD and atoA. The last ones were directly amplified from the genomic DNA of *E. coli* MG1655.

An expression vector containing the origin of replication pSC and a spectinomycin resistance marker was used for the expression of the genes thlA, atoD, atoA, adc and adh. The constructed vector was named pGB5344.

Expression in *E. coli* of the Enzymes Responsible for Conversion of Glyceraldehyde-3-Phosphate (G3P) and Dihydroxy-Acetone Phosphate (DHAP) into Fructose-6-Phosphate (F6P).

The modified version of pUC18 (New England Biolabs), containing a modified Multiple Cloning Site (pUC18 MCS) (WO 2013/007786), and an ampicilline resistance gene (plasmid pGB 271), was used for the overexpression of the genes listed in Table 8.

TABLE 8

Enzymes catalyzing the conversion of DHAP and G3P into F6P.

| Enzyme | Gene | NCBI reference | Uniprot Accession number | Constructed plasmid |
|---|---|---|---|---|
| Transaldolase from *Streptococcus suis* | FSAA_SS | WP_011922247.1 | A0A0E4C393 | PGB 12689 |
| 6-phosphogluconate phosphatase from *Escherichia coli* | YIEH | WP_000086486.1 | P31467 | |

TABLE 7

Enzymes catalyzing the conversion of acetyl-CoA into acetone and isopropanol

| Step | Enzyme | Gene | NCBI reference | Uniprot Accession number |
|---|---|---|---|---|
| I | Acetyl-CoA transferase from *Clostridium acetobutyticum* | THLA | WP_010966157.1 | P45359 |
| II | Acetate CoA-transferase from *Escherichia coli* | ATOD | NP_416725.1 | P76458 |
|  |  | ATOA | NP_416726.1 | P76459 |
| III | Acetoacetate decarboxylase from *Clostridium acetobutylicum* | ADC | NP_149328.1 | P23670 |
| IV | NADP-dependent isopropanol dehydrogenase from *Clostridium beijerinckii* | ADH | AF_157307.2 | P25984 |

The different combinations of the plasmids were transformed by electroporation into strain C. The strains produced in this way are summarized in Table 9.

TABLE 9

Strains generated for in vivo conversion of glucose into acetone + isopropanol.

| Strain | Vectors |
|---|---|
| STRAIN GBI 15847: Strain C, expressing the whole Acetone/Isopropanol metabolic pathway, without overexpression of enzymes responsible for conversion of Glyceraldehyde-3-Phosphate (G3P) and Dihydroxy-Acetone Phosphate (DHAP) into Frutose-6-Phosphate (F6P) | PGB 5344 + PGB 271 |

TABLE 9-continued

Strains generated for in vivo conversion
of glucose into acetone + isopropanol.

| Strain | Vectors |
|---|---|
| STRAIN GBI 17553: Strain C, expressing the whole Acetone/Isopropanol metabolic pathway, +overexpression of enzymes responsible for conversion of Glyceraldehyde-3-Phosphate (G3P) and Dihydroxy-Acetone Phosphate (DHAP) into Frutose-6-Phosphate (F6P) | PGB 5344 + PGB 12689 |

Example 6: Growth of E. coli Strains and Production of Acetone/Isopropanol from Acetyl-CoA Pre-Culture Conditions The transformed cells were then plated on LB plates, supplied with ampicillin (100 µg/ml) and spectinomycin (100 µg/ml). Plates were incubated for 2 days at 30° C. Isolated colonies were used to inoculate LB medium, supplemented with ampicillin and spectinomycin. These pre-cultures were grown at 30° C. to reach an optical density of 0.6.

Growth Conditions

The fermentation was performed in a 1 liter bioreactor with pH and temperature control (Multifors 2, Infors HT). Cells of pre-cultures were used to inoculate 500 ml of the fermentation medium (Table 10), complemented with ampicillin (100 µg/ml), spectinomycin (100 µg/ml), thiamine (0.6 mM), glucose (1 g/l) and glycerol (5 g/L), to achieve an initial optical density ($OD_{600}$) of 0.05. During the growth phase temperature (T=32° C.), pH=6.5 and $pO_2$=5% were maintained constant. The feed of glucose was increased from 0.1 g/g DCW/h to 0.35 g/g DCW/h. The pulses of the addition of 5 g/L of yeast extract were done when $OD_{600}$ reached 2, 8 and 20.

TABLE 10

Fermentation medium composition (derived from ZYM-5052 medium
(Studier FW, Prot. Exp. Pur. 41, (2005), 207-234)).

| Products | Final concentration in bioreactor |
|---|---|
| Yeast Extract | 5 g/L |
| Tryptone | 10 g/L |
| Sodium sulfate, $Na_2SO_4$ | 0.71 g/L |
| Ammonium sulfate, $(NH_4)_2SO_4$ | 1.34 g/L |
| Potassium phosphate monobasic, $KH_2PO_4$ | 3.4 g/L |
| Sodium phosphate dibasic, $Na_2HPO_4$ | 4.45 g/L |
| Magnesium sulfate, $MgSO_4$ | 4 mM |
| 5000X Trace elements solution | 1X |
| Antifoam Struktol ® J 673 A (Struktol) | 80 µl/L |

Acetone/Isopropanol Production Phase

During this phase temperature, T=34° C., pH 6.5, and $pO_2$=5% were maintained constant. Glucose feed was started at 0.50 g sucrose/g DCW/h and then adjusted according to the strain consumption. Glycerol concentration was maintained superior to 2 g/l.

The acetone/isopropanol production by the strains was analyzed continuously using a Gas Chromatograph 7890A (Agilent Technology), equipped with Flame Ionization Detector (FID) to measure acetone and isopropanol. Volatile organic compounds were chromatographically separated on Hi-Plex H USP L17, 100×7.7 mm (Agilent) using Agilent 1260 InfinityII chromatographer. acetone/isopropanol were quantified using standards (Sigma).

FIG. 3 shows the comparison between the observed specific productivity of acetone and isopropanol for a production strain expressing the enzymes responsible for the conversion of glyceraldehyde-3-phosphate (G3P) and dihydroxy-acetone phosphate (DHAP) into fructose-6-phosphate (F6P) or, as a control, for a strain which does not express the enzymes responsible for the conversion of glyceraldehyde-3-phosphate (G3P) and dihydroxy-acetone phosphate (DHAP) into fructose-6-phosphate (F6P).

When the enzymes responsible for conversion of glyceraldehyde-3-phosphate (G3P) and dihydroxy-acetone phosphate (DHAP) into fructose-6-phosphate (F6P) are overexpressed (strain GBI 17553), acetone and isopropanol specific productivity (moles produced per unit of cell weight per unit of time) is higher compared to the strain GBI 15847.

The invention claimed is:
1. A method for the production of fructose-6-phosphate (F6P) from dihydroxyacetone phosphate (DHAP) and glyceraldehyde-3-phosphate (G3P)
  (A) comprising the steps of:
    (a) enzymatically converting dihydroxyacetone phosphate (DHAP) into dihydroxyacetone (DHA) using a phosphoric monoester hydrolase (EC 3.1.3.-); and
    (b) enzymatically converting the thus produced dihydroxyacetone (DHA) together with glyceraldehyde-3-phosphate (G3P) into fructose-6-phosphate (F6P) using an aldehyde lyase (EC 4.1.2.-) or a transaldolase (EC 2.2.1.2); or
  (B) comprising the steps of:
    (a') enzymatically converting glyceraldehyde-3-phosphate (G3P) into glyceraldehyde using a phosphoric monoester hydrolase (EC 3.1.3.-); and
    (b') enzymatically converting the thus produced glyceraldehyde together with dihydroxyacetone phosphate (DHAP) into fructose-1-phosphate (F1P) using a fructose bisphosphate aldolase (EC 4.1.2.13); and
    (c') enzymatically converting the thus produced fructose-1-phosphate (F1P) into fructose-6-phosphate (F6P) using a phosphoglucomutase (EC 5.4.2.2) or a phosphomannomutase (EC 5.4.2.8).

2. The method of claim 1 comprising the steps of:
  (a) enzymatically converting dihydroxyacetone phosphate (DHAP) into dihydroxyacetone (DHA) using a phosphoric monoester hydrolase (EC 3.1.3.-); and
  (b) enzymatically converting the thus produced dihydroxyacetone (DHA) together with glyceraldehyde-3-phosphate (G3P) into fructose-6-phosphate (F6P) using an aldehyde lyase (EC 4.1.2.-) or a transaldolase (EC 2.2.1.2).

3. The method of claim 2, wherein the phosphoric monoester hydrolase (EC 3.1.3.-) is selected from the group consisting of:
  (i) sugar phosphatase (EC 3.1.3.23);
  (ii) 6-phosphogluconate phosphatase (EC 3.1.3.-);
  (iii) Pyridoxal phosphate phosphatase (EC 3.1.3.74);
  (iv) Fructose-1-phosphate phosphatase (EC 3.1.3.-);
  (v) Dihydroxyacetone phosphatase (EC 3.1.3.-);
  (vi) Hexitol phosphatase (EC 3.1.3.-);
  (vii) Acid phosphatase (EC 3.1.3.2);
  (viii) Alkaline phosphatase (EC 3.1.3.1);
  (ix) Glycerol-1-phosphate phosphatase (EC 3.1.3.21); and
  (x) 3-phosphoglycerate phosphatase (EC 3.1.3.38).

4. The method of claim 2, wherein the conversion of dihydroxyacetone (DHA) and glyceraldehyde-3-phosphate (G3P) into fructose-6-phosphate (F6P) according to step (b) is achieved by
an aldehyde lyase (EC 4.1.2.-).

5. The method of claim 1 comprising the steps of:
  (a') enzymatically converting glyceraldehyde-3-phosphate (G3P) into glyceraldehyde using a phosphoric monoester hydrolase (EC 3.1.3.-); and
  (b') enzymatically converting the thus produced glyceraldehyde together with dihydroxyacetone phosphate (DHAP) into fructose-1-phosphate (F1P) using a fructose bisphosphate aldolase (EC 4.1.2.13); and
  (c') enzymatically converting the thus produced fructose-1-phosphate (F1P) into fructose-6-phosphate (F6P) using a phosphoglucomutase (EC 5.4.2.2) or a phosphomannomutase (EC 5.4.2.8).

6. The method of claim 5, wherein the phosphoric monoester hydrolase (EC 3.1.3.-) is selected from the group consisting of:
  (i) Glyceraldehyde 3-phosphate phosphatase (EC 3.1.3.-);
  (ii) Alkaline phosphatase (EC 3.1.3.1);
  (iii) Acid phosphatase (EC 3.1.3.2);
  (iv) Sugar phosphatase (EC 3.1.3.23); and
  (v) Hexitol phosphatase (EC 3.1.3.-).

7. The method of claim 1 (B), wherein the conversion of fructose-1-phosphate (F1P) into fructose-6-phosphate (F6P) according to step (c') is achieved by a Phosphoglucomutase (EC 5.4.2.2).

8. The method of claim 1 (B), wherein the conversion of fructose-1-phosphate (F1P) into fructose-6-phosphate (F6P) according to step (c') is achieved by a Phosphomannomutase (EC 5.4.2.8).

9. The method of claim 1 which is carried out in vitro.

10. The method of claim 1(A) which is carried out in vivo in a recombinant microorganism which has been transformed with a nucleotide sequence which encodes an enzyme which can catalyze the conversion recited in step (a) of claim 1 and with a nucleotide sequence which encodes an enzyme which can catalyze the conversion recited in step (b) of claim 1.

11. The method of claim 1(B) which is carried out in vivo in a recombinant microorganism which has been transformed with a nucleotide sequence which encodes an enzyme which can catalyze the conversion recited in step (a') of claim 1 (B) and with a nucleotide sequence which encodes an enzyme which can catalyze the conversion recited in step (b') of claim 1 (B).

12. The method of claim 11, wherein the microorganism has furthermore been transformed with a nucleotide sequence which encodes an enzyme which can catalyze the conversion recited in step (c') of claim 1 (C).

13. The method of claim 10, wherein the microorganism is furthermore characterized in that it
  a) has phosphoketolase activity;
  b) (i) has a diminished or inactivated Embden-Meyerhof-Parnas pathway (EMPP) by inactivation of the gene(s) encoding phosphofructokinase or by reducing phosphofructokinase activity as compared to a non-modified microorganism; or
    (ii) does not possess phosphofructokinase activity; and
  c) (i) has a diminished or inactivated oxidative branch of the pentose phosphate pathway (PPP) by inactivation of the gene(s) encoding glucose-6-phosphate dehydrogenase or by reducing glucose-6-phosphate dehydrogenase activity as compared to a non-modified microorganism; or
    (ii) does not possess glucose-6-phosphate dehydrogenase activity.

14. The method of claim 13, wherein the microorganism is furthermore characterized in that the EMPP is further diminished or inactivated by inactivation of the gene(s) encoding glyceraldehyde 3-phosphate dehydrogenase or by reducing glyceraldehyde 3-phosphate dehydrogenase activity as compared to a non-modified microorganism.

15. The method of claim 1, wherein said method is carried out in vivo in a recombinant microorganism, wherein said microorganism has been transformed with
  (a) a nucleotide sequence encoding a phosphoric monoester hydrolase (EC 3.1.3.-); and
  (b) a nucleotide sequence encoding an enzyme selected from the group consisting of
    (i) an aldehyde lyase (EC 4.1.2.-); and/or
    (ii) a transaldolase (EC 2.2.1.2).

16. The method of claim 1, wherein said method is carried out in vivo in a recombinant microorganism, wherein said microorganism has been transformed with
  (a) a nucleotide sequence encoding a phosphoric monoester hydrolase (EC 3.1.3.-); and
  (b) a nucleotide sequence encoding a fructose bisphosphate aldolase (EC 4.1.2.13);
wherein said microorganism also possesses phosphoglucomutase (EC 5.4.2.2) or phosphomannomutase (EC 5.4.2.8) activity.

17. The method of claim 16, wherein said microorganism has been further transformed with a nucleotide sequence encoding an enzyme selected from the group consisting of:
  (i) Phosphoglucomutase (EC 5.4.2.2); and
  (ii) Phosphomannomutase (EC 5.4.2.8).

18. The method of claim 2, wherein the conversion of dihydroxyacetone (DHA) and glyceraldehyde-3-phosphate (G3P) into fructose-6-phosphate (F6P) according to step (b) is achieved by a transaldolase (EC. 2.2.1.2).

* * * * *

SEQUENCE LISTING

```
<160> NUMBER OF SEQ ID NOS: 64

<210> SEQ ID NO 1
<211> LENGTH: 271
<212> TYPE: PRT
<213> ORGANISM: E. coli K-12

<400> SEQUENCE: 1

Met Ser Val Lys Val Ile Val Thr Asp Met Asp Gly Thr Phe Leu Asn
1               5                   10                  15

Asp Ala Lys Thr Tyr Asn Gln Pro Arg Phe Met Ala Gln Tyr Gln Glu
                20                  25                  30

Leu Lys Lys Arg Gly Ile Lys Phe Val Val Ala Ser Gly Asn Gln Tyr
            35                  40                  45

Tyr Gln Leu Ile Ser Phe Phe Pro Glu Leu Lys Asp Glu Ile Ser Phe
        50                  55                  60

Val Ala Glu Asn Gly Ala Leu Val Tyr Glu His Gly Lys Gln Leu Phe
65                  70                  75                  80
```

```
His Gly Glu Leu Thr Arg His Glu Ser Arg Ile Val Ile Gly Glu Leu
                85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
        115                 120                 125

His Tyr His Arg Leu Lys Pro Val Lys Asp Tyr Gln Glu Ile Asp Asp
    130                 135                 140

Val Leu Phe Lys Phe Ser Leu Asn Leu Pro Asp Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Pro Gly Leu His Lys
            180                 185                 190

Ala Asn Gly Ile Ser Arg Leu Leu Lys Arg Trp Asp Leu Ser Pro Gln
        195                 200                 205

Asn Val Val Ala Ile Gly Asp Ser Gly Asn Asp Ala Glu Met Leu Lys
    210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270

<210> SEQ ID NO 2
<211> LENGTH: 270
<212> TYPE: PRT
<213> ORGANISM: E. coli K-12

<400> SEQUENCE: 2

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
```

```
                180             185             190
Lys Arg Val Asn Lys Gly Thr Gly Val Lys Ser Leu Ala Asp Val Leu
            195             200             205
Gly Ile Lys Pro Glu Glu Ile Met Ala Ile Gly Asp Gln Glu Asn Asp
            210             215             220
Ile Ala Met Ile Glu Tyr Ala Gly Val Gly Val Ala Met Asp Asn Ala
225             230             235             240
Ile Pro Ser Val Lys Glu Val Ala Asn Phe Val Thr Lys Ser Asn Leu
            245             250             255
Glu Asp Gly Val Ala Phe Ala Ile Glu Lys Tyr Val Leu Asn
            260             265             270

<210> SEQ ID NO 3
<211> LENGTH: 221
<212> TYPE: PRT
<213> ORGANISM: E. coli K-12

<400> SEQUENCE: 3

Met Ser Arg Ile Glu Ala Val Phe Phe Asp Cys Asp Gly Thr Leu Val
1               5               10              15
Asp Ser Glu Val Ile Cys Ser Arg Ala Tyr Val Thr Met Phe Gln Glu
            20              25              30
Phe Gly Ile Thr Leu Asp Pro Glu Glu Val Phe Lys Arg Phe Lys Gly
        35              40              45
Val Lys Leu Tyr Glu Ile Ile Asp Ile Val Ser Leu Glu His Gly Val
    50              55              60
Thr Leu Ala Lys Thr Glu Ala Glu His Val Tyr Arg Ala Glu Val Ala
65              70              75              80
Arg Leu Phe Asp Ser Glu Leu Glu Ala Ile Glu Gly Ala Gly Ala Leu
                85              90              95
Leu Ser Ala Ile Thr Ala Pro Met Cys Val Val Ser Asn Gly Pro Asn
            100             105             110
Asn Lys Met Gln His Ser Met Gly Lys Leu Asn Met Leu His Tyr Phe
        115             120             125
Pro Asp Lys Leu Phe Ser Gly Tyr Asp Ile Gln Arg Trp Lys Pro Asp
    130             135             140
Pro Ala Leu Met Phe His Ala Ala Lys Ala Met Asn Val Asn Val Glu
145             150             155             160
Asn Cys Ile Leu Val Asp Asp Ser Val Ala Gly Ala Gln Ser Gly Ile
                165             170             175
Asp Ala Gly Met Glu Val Phe Tyr Phe Cys Ala Asp Pro His Asn Lys
            180             185             190
Pro Ile Val His Pro Lys Val Thr Thr Phe Thr His Leu Ser Gln Leu
        195             200             205
Pro Glu Leu Trp Lys Ala Arg Gly Trp Asp Ile Thr Ala
    210             215             220

<210> SEQ ID NO 4
<211> LENGTH: 266
<212> TYPE: PRT
<213> ORGANISM: E. coli K-12

<400> SEQUENCE: 4

Met Tyr Gln Val Val Ala Ser Asp Leu Asp Gly Thr Leu Leu Ser Pro
1               5               10              15
Asp His Thr Leu Ser Pro Tyr Ala Lys Glu Thr Leu Lys Leu Leu Thr
```

```
            20                  25                  30
Ala Arg Gly Ile Asn Phe Val Phe Ala Thr Gly Arg His His Val Asp
            35                  40                  45

Val Gly Gln Ile Arg Asp Asn Leu Glu Ile Lys Ser Tyr Met Ile Thr
        50                  55                  60

Ser Asn Gly Ala Arg Val His Asp Leu Asp Gly Asn Leu Ile Phe Ala
65                  70                  75                  80

His Asn Leu Asp Arg Asp Ile Ala Ser Asp Leu Phe Gly Val Val Asn
                85                  90                  95

Asp Asn Pro Asp Ile Ile Thr Asn Val Tyr Arg Asp Asp Glu Trp Phe
            100                 105                 110

Met Asn Arg His Arg Pro Glu Glu Met Arg Phe Phe Lys Glu Ala Val
        115                 120                 125

Phe Gln Tyr Ala Leu Tyr Glu Pro Gly Leu Leu Glu Pro Glu Gly Val
    130                 135                 140

Ser Lys Val Phe Phe Thr Cys Asp Ser His Glu Gln Leu Leu Pro Leu
145                 150                 155                 160

Glu Gln Ala Ile Asn Ala Arg Trp Gly Asp Arg Val Asn Val Ser Phe
                165                 170                 175

Ser Thr Leu Thr Cys Leu Glu Val Met Ala Gly Val Ser Lys Gly
            180                 185                 190

His Ala Leu Glu Ala Val Ala Lys Lys Leu Gly Tyr Ser Leu Lys Asp
        195                 200                 205

Cys Ile Ala Phe Gly Asp Gly Met Asn Asp Ala Glu Met Leu Ser Met
    210                 215                 220

Ala Gly Lys Gly Cys Ile Met Gly Ser Ala His Gln Arg Leu Lys Asp
225                 230                 235                 240

Leu His Pro Glu Leu Glu Val Ile Gly Thr Asn Ala Asp Asp Ala Val
                245                 250                 255

Pro His Tyr Leu Arg Lys Leu Tyr Leu Ser
            260                 265

<210> SEQ ID NO 5
<211> LENGTH: 188
<212> TYPE: PRT
<213> ORGANISM: E. coli K-12

<400> SEQUENCE: 5

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
            20                  25                  30

His Tyr Gly Leu Gln Tyr Asp Ile Gln Ala Met Ile Ala Leu Asn Gly
        35                  40                  45

Ser Pro Thr Trp Arg Ile Ala Gln Ala Ile Ile Glu Leu Asn Gln Ala
    50                  55                  60

Asp Leu Asp Pro His Ala Leu Ala Arg Glu Lys Thr Glu Ala Val Arg
65                  70                  75                  80

Ser Met Leu Leu Asp Ser Val Glu Pro Leu Pro Leu Val Asp Val Val
                85                  90                  95

Lys Ser Trp His Gly Arg Arg Pro Met Ala Val Gly Thr Gly Ser Glu
            100                 105                 110

Ser Ala Ile Ala Glu Ala Leu Leu Ala His Leu Gly Leu Arg His Tyr
        115                 120                 125
```

Phe Asp Ala Val Val Ala Ala Asp His Val Lys His His Lys Pro Ala
            130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
                165                 170                 175

Ala Ala Gly Met Asp Ala Val Asp Val Arg Leu Leu
            180                 185

<210> SEQ ID NO 6
<211> LENGTH: 275
<212> TYPE: PRT
<213> ORGANISM: Corynebacterium glutamicum (strain R)

<400> SEQUENCE: 6

Met Thr Val Asn Ile Ser Tyr Leu Thr Asp Met Asp Gly Val Leu Ile
1               5                   10                  15

Lys Glu Gly Glu Met Ile Pro Gly Ala Asp Arg Phe Leu Gln Ser Leu
            20                  25                  30

Thr Asp Asn Asn Val Glu Phe Met Val Leu Thr Asn Asn Ser Ile Phe
        35                  40                  45

Thr Pro Arg Asp Leu Ser Ala Arg Leu Lys Thr Ser Gly Leu Asp Ile
50                  55                  60

Pro Pro Glu Arg Ile Trp Thr Ser Ala Thr Ala His Phe Leu
65                  70                  75                  80

Lys Ser Gln Val Lys Glu Gly Thr Ala Tyr Val Val Gly Glu Ser Gly
                85                  90                  95

Leu Thr Thr Ala Leu His Thr Ala Gly Trp Ile Leu Thr Asp Ala Asn
            100                 105                 110

Pro Glu Phe Val Val Leu Gly Glu Thr Arg Thr Tyr Ser Phe Glu Ala
        115                 120                 125

Ile Thr Thr Ala Ile Asn Leu Ile Leu Gly Gly Ala Arg Phe Ile Cys
130                 135                 140

Thr Asn Pro Asp Val Thr Gly Pro Ser Pro Ser Gly Ile Leu Pro Ala
145                 150                 155                 160

Thr Gly Ser Val Ala Ala Leu Ile Thr Ala Ala Thr Gly Ala Glu Pro
                165                 170                 175

Tyr Tyr Ile Gly Lys Pro Asn Pro Val Met Met Arg Ser Ala Leu Asn
            180                 185                 190

Thr Ile Gly Ala His Ser Glu His Thr Val Met Ile Gly Asp Arg Met
        195                 200                 205

Asp Thr Asp Val Lys Ser Gly Leu Glu Ala Gly Leu Ser Thr Val Leu
210                 215                 220

Val Arg Ser Gly Ile Ser Asp Asp Ala Glu Ile Arg Arg Tyr Pro Phe
225                 230                 235                 240

Arg Pro Thr His Val Ile Asn Ser Ile Ala Asp Leu Ala Asp Cys Trp
                245                 250                 255

Asp Asp Pro Phe Gly Asp Gly Ala Phe His Val Pro Asp Glu Gln Gln
            260                 265                 270

Phe Thr Asp
        275

<210> SEQ ID NO 7
<211> LENGTH: 216
<212> TYPE: PRT
<213> ORGANISM: E. coli K-12

```
<400> SEQUENCE: 7

Met Arg Cys Lys Gly Phe Leu Phe Asp Leu Asp Gly Thr Leu Val Asp
1               5                   10                  15

Ser Leu Pro Ala Val Glu Arg Ala Trp Ser Asn Trp Ala Arg Arg His
            20                  25                  30

Gly Leu Ala Pro Glu Glu Val Leu Ala Phe Ile His Gly Lys Gln Ala
        35                  40                  45

Ile Thr Ser Leu Arg His Phe Met Ala Gly Lys Ser Glu Ala Asp Ile
    50                  55                  60

Ala Ala Glu Phe Thr Arg Leu Glu His Ile Glu Ala Thr Glu Thr Glu
65                  70                  75                  80

Gly Ile Thr Ala Leu Pro Gly Ala Ile Ala Leu Leu Ser His Leu Asn
                85                  90                  95

Lys Ala Gly Ile Pro Trp Ala Ile Val Thr Ser Gly Ser Met Pro Val
            100                 105                 110

Ala Arg Ala Arg His Lys Ile Ala Gly Leu Pro Ala Pro Glu Val Phe
        115                 120                 125

Val Thr Ala Glu Arg Val Lys Arg Gly Lys Pro Glu Pro Asp Ala Tyr
    130                 135                 140

Leu Leu Gly Ala Gln Leu Leu Gly Leu Ala Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Asn Glu
            180                 185                 190

Val Asp Leu Val Leu His Ser Leu Glu Gln Ile Thr Val Thr Lys Gln
        195                 200                 205

Pro Asn Gly Asp Val Ile Ile Gln
    210                 215

<210> SEQ ID NO 8
<211> LENGTH: 220
<212> TYPE: PRT
<213> ORGANISM: Escherichia coli K-12

<400> SEQUENCE: 8

Met Glu Leu Tyr Leu Asp Thr Ser Asp Val Val Ala Val Lys Ala Leu
1               5                   10                  15

Ser Arg Ile Phe Pro Leu Ala Gly Val Thr Thr Asn Pro Ser Ile Ile
            20                  25                  30

Ala Ala Gly Lys Lys Pro Leu Asp Val Val Leu Pro Gln Leu His Glu
        35                  40                  45

Ala Met Gly Gly Gln Gly Arg Leu Phe Ala Gln Val Met Ala Thr Thr
    50                  55                  60

Ala Glu Gly Met Val Asn Asp Ala Leu Lys Leu Arg Ser Ile Ile Ala
65                  70                  75                  80

Asp Ile Val Val Lys Val Pro Val Thr Ala Glu Gly Leu Ala Ala Ile
                85                  90                  95

Lys Met Leu Lys Ala Glu Gly Ile Pro Thr Leu Gly Thr Ala Val Tyr
            100                 105                 110

Gly Ala Ala Gln Gly Leu Leu Ser Ala Leu Ala Gly Ala Glu Tyr Val
        115                 120                 125

Ala Pro Tyr Val Asn Arg Ile Asp Ala Gln Gly Gly Ser Gly Ile Gln
    130                 135                 140
```

Thr Val Thr Asp Leu His Gln Leu Leu Lys Met His Ala Pro Gln Ala
145                 150                 155                 160

Lys Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Ile Ser Tyr Pro Ala Val Asp Ala Ala Val Ala Lys Phe Glu
        195                 200                 205

Gln Asp Trp Gln Gly Ala Phe Gly Arg Thr Ser Ile
    210                 215                 220

<210> SEQ ID NO 9
<211> LENGTH: 220
<212> TYPE: PRT
<213> ORGANISM: Escherichia coli K-12

<400> SEQUENCE: 9

Met Glu Leu Tyr Leu Asp Thr Ser Asp Val Val Ala Val Lys Ala Leu
1               5                   10                  15

Ser Arg Ile Phe Pro Leu Ala Gly Val Thr Thr Asn Pro Ser Ile Ile
                20                  25                  30

Ala Ala Gly Lys Lys Pro Leu Asp Val Val Leu Pro Gln Leu His Glu
            35                  40                  45

Ala Met Gly Gly Gln Gly Arg Leu Phe Ala Gln Val Met Ala Thr Thr
        50                  55                  60

Ala Glu Gly Met Val Asn Asp Ala Leu Lys Leu Arg Ser Ile Ile Ala
65                  70                  75                  80

Asp Ile Val Val Lys Val Pro Val Thr Ala Glu Gly Leu Ala Ala Ile
                85                  90                  95

Lys Met Leu Lys Ala Glu Gly Ile Pro Thr Leu Gly Thr Ala Val Tyr
            100                 105                 110

Gly Ala Ala Gln Gly Leu Leu Ser Ala Leu Ala Gly Ala Glu Tyr Val
        115                 120                 125

Ser Pro Tyr Val Asn Arg Ile Asp Ala Gln Gly Gly Ser Gly Ile Gln
    130                 135                 140

Thr Val Thr Asp Leu His Gln Leu Leu Lys Met His Ala Pro Gln Ala
145                 150                 155                 160

Lys Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Ile Ser Tyr Pro Ala Val Asp Ala Ala Val Ala Lys Phe Glu
        195                 200                 205

Gln Asp Trp Gln Gly Ala Phe Gly Arg Thr Ser Ile
    210                 215                 220

<210> SEQ ID NO 10
<211> LENGTH: 222
<212> TYPE: PRT
<213> ORGANISM: Streptococcus gordonii

<400> SEQUENCE: 10

Met Glu Phe Met Leu Asp Thr Leu Asn Leu Glu Glu Ile Lys Lys Trp
1               5                   10                  15

Ser Glu Val Leu Pro Leu Ala Gly Val Thr Ser Asn Pro Thr Ile Ala
                20                  25                  30

```
Lys Lys Glu Gly Lys Ile Asp Phe Phe Glu Arg Ile Ser Ala Val Arg
             35                  40                  45

Glu Ile Ile Gly Glu Gly Pro Ser Ile His Val Gln Val Val Ala Lys
 50                  55                  60

Asp Tyr Glu Gly Ile Leu Lys Asp Ala Ala Thr Ile Arg Lys Lys Cys
 65                  70                  75                  80

Gly Asp Ala Val Tyr Ile Lys Ile Pro Val Thr Pro Asp Gly Leu Ala
                 85                  90                  95

Ala Ile Lys Thr Leu Lys Ala Glu Gly Tyr Lys Ile Thr Ala Thr Ala
             100                 105                 110

Ile Tyr Thr Thr Phe Gln Gly Leu Leu Ala Ile Glu Ala Glu Ala Asp
             115                 120                 125

Tyr Leu Ala Pro Tyr Tyr Asn Arg Met Glu Asn Leu Asn Ile Asp Ser
130                 135                 140

Asp Ala Val Ile Ser Gln Leu Ala Gln Ala Ile Glu Arg Asp His Ser
145                 150                 155                 160

Asp Ser Lys Ile Leu Ala Ala Ser Phe Lys Asn Val Ala Gln Val Asn
                165                 170                 175

Arg Ala Phe Ala Asp Gly Ala Gln Ala Val Thr Ala Gly Pro Asp Val
            180                 185                 190

Phe Ala Ala Phe Ala Met Pro Ser Ile Ala Lys Ala Val Asp Asp
            195                 200                 205

Phe Ala Thr Asp Trp Ser Asp Ile His Ser Gln Glu Tyr Val
210                 215                 220

<210> SEQ ID NO 11
<211> LENGTH: 216
<212> TYPE: PRT
<213> ORGANISM: Listeria monocytogenes

<400> SEQUENCE: 11

Met His Leu Asp Ser Ala Asn Leu Asp Asp Val Lys Lys Ile Gln Ala
 1               5                  10                  15

Ser Ser Ile Phe Lys Gly Ile Thr Thr Asn Pro Ser Ile Leu Val Lys
             20                  25                  30

Glu Lys Cys Asn Arg Gln Thr Ala Ile Asn Arg Ile Leu Glu Leu Thr
             35                  40                  45

Asp Lys Gln Val Phe Val Gln Thr Val Gly Phe Thr Tyr Glu Glu Ile
 50                  55                  60

Leu Ala Asp Ala Arg Met Leu Leu Thr Met Phe Gly Lys Asp Lys Ile
 65                  70                  75                  80

Ala Ile Lys Ile Pro Ala His Glu Ala Gly Thr Asn Val Ile Asp Thr
                 85                  90                  95

Leu Lys Lys Glu Asp Lys Thr Ile Gln Ile Leu Gly Thr Ala Ile Tyr
             100                 105                 110

Ser Ala Asp Gln Ala Ile Thr Ala Ala Leu Ala Gly Ala Asp Phe Val
             115                 120                 125

Ala Pro Tyr Val Asn Arg Met Ser Ala Ala Asn Ile Asp Pro Phe Lys
130                 135                 140

Glu Ile Thr Gln Met Arg His Phe Phe Asp Lys Lys Ala Leu Lys Thr
145                 150                 155                 160

Gln Ile Met Ala Ala Ser Phe Lys His Ser Gly Gln Val Met Gln Ala
                165                 170                 175

Tyr Glu Ser Gly Ala Asp Thr Val Thr Ile Pro Tyr Glu Ile Tyr Ser
```

```
                180                 185                 190
Gln Met Thr Asn Lys Val Leu Ala Val Glu Ala Ile Arg Val Phe Asn
            195                 200                 205
Glu Asp Ala Val Leu Tyr Glu Lys
        210                 215

<210> SEQ ID NO 12
<211> LENGTH: 222
<212> TYPE: PRT
<213> ORGANISM: Streptococcus pyogenes

<400> SEQUENCE: 12

Met Glu Tyr Met Leu Asp Thr Leu Asp Leu Glu Ala Ile Lys Lys Trp
1               5                  10                  15

His His Ile Leu Pro Leu Ala Gly Val Thr Ser Asn Pro Ser Ile Ala
            20                  25                  30

Lys Lys Glu Gly Glu Ile Asp Phe Phe Glu Arg Ile Arg Glu Val Arg
        35                  40                  45

Ala Ile Ile Gly Asp Lys Ala Ser Ile His Val Gln Val Ile Ala Gln
    50                  55                  60

Asp Tyr Glu Gly Ile Leu Lys Asp Ala Ala Glu Ile Arg Arg Gln Cys
65                  70                  75                  80

Gly Asp Ser Val Tyr Val Lys Val Pro Val Thr Thr Glu Gly Leu Ala
                85                  90                  95

Ala Ile Lys Thr Leu Lys Ala Glu Gly Tyr His Ile Thr Ala Thr Ala
            100                 105                 110

Ile Tyr Thr Thr Phe Gln Gly Leu Leu Ala Ile Glu Ala Gly Ala Asp
        115                 120                 125

Tyr Leu Ala Pro Tyr Tyr Asn Arg Met Glu Asn Leu Asn Ile Asp Pro
    130                 135                 140

Glu Ala Val Ile Glu Gln Leu Ala Glu Ala Ile Asn Arg Glu Asn Ala
145                 150                 155                 160

Asn Ser Lys Ile Leu Ala Ala Ser Phe Lys Asn Val Ala Gln Val Asn
                165                 170                 175

Lys Ser Phe Ala Leu Gly Ala Gln Ala Ile Thr Ala Gly Pro Asp Val
            180                 185                 190

Phe Glu Ala Gly Phe Ala Met Pro Ser Ile Gln Lys Ala Val Asp Asp
        195                 200                 205

Phe Gly Lys Asp Trp Glu Ala Ile His His Arg Lys Ser Ile
    210                 215                 220

<210> SEQ ID NO 13
<211> LENGTH: 215
<212> TYPE: PRT
<213> ORGANISM: Clostridium beijerinckii

<400> SEQUENCE: 13

Met Arg Phe Phe Leu Asp Thr Ala Asn Val Asp His Ile Lys Glu Ala
1               5                  10                  15

Asn Glu Met Gly Val Ile Cys Gly Val Thr Thr Asn Pro Ser Leu Val
            20                  25                  30

Ala Lys Glu Gly Arg Asp Phe Asn Glu Val Ile Lys Glu Ile Thr Glu
        35                  40                  45

Ile Val Asp Gly Pro Ile Ser Gly Glu Val Val Ala Glu Asp Ala Gln
    50                  55                  60

Gly Met Ile Lys Glu Gly Arg Glu Ile Ala Ala Ile His Lys Asn Met
```

```
             65                  70                  75                  80
        Ile Val Lys Ile Pro Met Thr Ala Glu Gly Leu Lys Ala Thr Lys Val
                             85                  90                  95

Leu Ser Ser Glu Gly Ile Lys Thr Asn Val Thr Leu Ile Phe Ser Ala
                            100                 105                 110

Thr Gln Ser Leu Leu Ala Ala Asn Ala Gly Ala Thr Tyr Val Ser Pro
                            115                 120                 125

Phe Leu Gly Arg Val Asp Asp Ile Ser Met Ile Gly Met Asp Leu Val
                    130                 135                 140

Arg Asp Ile Ala Glu Ile Phe Ala Val His Gly Ile Glu Thr Glu Ile
        145                 150                 155                 160

Ile Ala Ala Ser Val Arg Asn Pro Ile His Val Ile Glu Ala Ala Lys
                            165                 170                 175

Ala Gly Ala Asp Ile Ala Thr Ile Pro Tyr Ala Leu Val Met Gln Met
                    180                 185                 190

Leu Asn His Pro Leu Thr Asp Gln Gly Leu Glu Lys Phe Lys Ala Asp
                        195                 200                 205

Trp Ala Ala Ala Phe Gly Lys
            210                 215

<210> SEQ ID NO 14
<211> LENGTH: 217
<212> TYPE: PRT
<213> ORGANISM: Caulobacter vibrioides

<400> SEQUENCE: 14

Met Gln Ile Phe Leu Asp Ser Thr Asp Thr Lys Val Ile Ala Asp Leu
        1               5                   10                  15

Ala Ser Thr Gly Leu Ile Asp Gly Val Thr Thr Asn Pro Thr Leu Ile
                        20                  25                  30

Ala Lys Ser Gly Arg Pro Met Leu Glu Val Ile Ala Glu Ile Cys Asp
                    35                  40                  45

Ile Val Pro Gly Pro Ile Ser Ala Glu Val Ala Ala Thr Thr Ala Asp
            50                  55                  60

Ala Met Ile Ala Glu Gly Gln Lys Leu Ala Lys Ile Ala Pro Asn Val
        65                  70                  75                  80

Val Val Lys Ile Pro Leu Thr Arg Asp Gly Leu Ile Ala Cys Ala Ala
                            85                  90                  95

Phe Ala Asp Glu Glu Ile Lys Thr Asn Val Thr Leu Cys Phe Ser Pro
                            100                 105                 110

Thr Gln Ala Leu Leu Ala Ala Lys Ala Gly Ala Thr Tyr Ile Ser Pro
                            115                 120                 125

Phe Ile Gly Arg Leu Asp Asp Tyr Gly Phe Asp Gly Met Asp Leu Ile
                    130                 135                 140

Arg Asp Ile Arg Ala Ile Tyr Asp Asn Tyr Gly Tyr Glu Thr Glu Ile
        145                 150                 155                 160

Leu Ala Ala Ser Val Arg Asn Ala Ala His Val Lys Glu Ala Ala Ile
                            165                 170                 175

Val Gly Ala Asp Val Val Thr Ile Pro Pro Ala Val Phe Ser Asp Leu
                    180                 185                 190

Tyr Lys His Pro Leu Thr Asp Lys Gly Leu Glu Gln Phe Leu Lys Asp
                        195                 200                 205

Trp Ala Ser Thr Gly Gln Ser Ile Leu
            210                 215
```

<210> SEQ ID NO 15
<211> LENGTH: 222
<212> TYPE: PRT
<213> ORGANISM: Streptococcus mutans

<400> SEQUENCE: 15

Met Glu Phe Met Leu Asp Thr Leu Asn Leu Ala Asp Ile Glu Lys Trp
1               5                   10                  15

Ala Ala Ile Leu Pro Leu Ala Gly Val Thr Ser Asn Pro Ser Ile Ala
            20                  25                  30

Lys Lys Glu Gly Lys Ile Asp Phe Phe Glu Gln Val Lys Arg Val Arg
        35                  40                  45

Ala Ile Ile Gly Glu Glu Pro Ser Ile His Ala Gln Val Val Ala Ala
    50                  55                  60

Asp Val Glu Gly Ile Ile Lys Asp Ala His Lys Leu Gln Asp Glu Leu
65                  70                  75                  80

Gly Gly Asn Leu Tyr Val Lys Val Pro Val Ser Pro Thr Gly Leu Thr
                85                  90                  95

Ala Met Lys Gln Leu Lys Glu Glu Gly Phe Gln Ile Thr Ala Thr Ala
            100                 105                 110

Ile Tyr Thr Val Phe Gln Gly Leu Leu Ala Ile Glu Ala Gly Ala Asp
        115                 120                 125

Tyr Leu Ala Pro Tyr Tyr Asn Arg Met Glu Asn Leu Asn Ile Asp Pro
    130                 135                 140

Ile Glu Val Ile Gly Gln Leu Ala Gln Ala Ile Glu Cys Gln Gln Ala
145                 150                 155                 160

Ser Ala Lys Ile Leu Ala Ala Ser Phe Lys Asn Val Thr Gln Val Ala
                165                 170                 175

Lys Ala Leu Ala Ala Gly Ala Lys Ala Val Thr Ala Gly Ala Asp Ile
            180                 185                 190

Phe Ala Ala Gly Phe Ala Asn Pro Ser Ile Gln Lys Ala Val Asp Asp
        195                 200                 205

Phe Ala Ala Asp Trp Glu Ser Thr Gln Gly Arg Pro Tyr Ile
    210                 215                 220

<210> SEQ ID NO 16
<211> LENGTH: 220
<212> TYPE: PRT
<213> ORGANISM: E. coli

<400> SEQUENCE: 16

Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Ile
            20                  25                  30

Ala Ala Ser Lys Glu Ser Ile Trp Glu Val Leu Pro Arg Leu Gln Lys
        35                  40                  45

Ala Ile Gly Asp Glu Gly Ile Leu Phe Ala Gln Thr Met Ser Arg Asp
    50                  55                  60

Ala Gln Gly Met Val Glu Glu Ala Lys Arg Leu Arg Asp Ala Ile Pro
65                  70                  75                  80

Gly Ile Val Val Lys Ile Pro Val Thr Ser Glu Gly Leu Ala Ala Ile
                85                  90                  95

Lys Ile Leu Lys Lys Glu Gly Ile Thr Thr Leu Gly Thr Ala Val Tyr
            100                 105                 110

Ser Ala Ala Gln Gly Leu Leu Ala Leu Ala Gly Ala Lys Tyr Val
115                 120                 125

Ala Pro Tyr Val Asn Arg Val Asp Ala Gln Gly Asp Gly Ile Arg
130                 135                 140

Thr Val Gln Glu Leu Gln Thr Leu Leu Glu Met His Ala Pro Glu Ser
145                 150                 155                 160

Met Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
                180                 185                 190

Gln Met Leu Asn Thr Pro Ala Val Glu Ser Ala Ile Glu Lys Phe Glu
                195                 200                 205

His Asp Trp Asn Ala Ala Phe Gly Thr Thr His Leu
210                 215                 220

<210> SEQ ID NO 17
<211> LENGTH: 317
<212> TYPE: PRT
<213> ORGANISM: E. coli

<400> SEQUENCE: 17

Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
                20                  25                  30

Thr Thr Asn Pro Ser Leu Ile Leu Asn Ala Ala Gln Ile Pro Glu Tyr
                35                  40                  45

Arg Lys Leu Ile Asp Asp Ala Val Ala Trp Ala Lys Gln Gln Ser Asn
50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
                100                 105                 110

Lys Arg Leu Ile Lys Leu Tyr Asn Asp Ala Gly Ile Ser Asn Asp Arg
            115                 120                 125

Ile Leu Ile Lys Leu Ala Ser Thr Trp Gln Gly Ile Arg Ala Ala Glu
            130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Tyr Val Gly Arg Ile Leu Asp Trp Tyr Lys Ala Asn Thr Asp Lys
                180                 185                 190

Lys Glu Tyr Ala Pro Ala Glu Asp Pro Gly Val Val Ser Val Ser Glu
            195                 200                 205

Ile Tyr Gln Tyr Tyr Lys Glu His Gly Tyr Glu Thr Val Val Met Gly
210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
                260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
        290                 295                 300

Asp Gln Glu Lys Leu Glu Lys Met Ile Gly Asp Leu Leu
305                 310                 315

<210> SEQ ID NO 18
<211> LENGTH: 225
<212> TYPE: PRT
<213> ORGANISM: Enterococcus faecalis

<400> SEQUENCE: 18

Met Glu Phe Met Leu Asp Thr Ile Asn Leu Glu Ala Ile Arg Lys Tyr
1               5                   10                  15

Gln Lys Ile Leu Pro Leu Ala Gly Val Thr Ser Asn Pro Ser Ile Val
            20                  25                  30

Lys Gln Ala Gly Lys Ile Asp Phe Phe Ala Gln Met Lys Glu Ile Lys
        35                  40                  45

Lys Thr Ile Gly Gln Ala Ser Leu His Val Gln Val Gly Gln Thr
    50                  55                  60

Thr Glu Glu Met Leu Glu Asp Ala Gln Thr Ile Val Gln Leu Gly
65                  70                  75                  80

Gln Glu Thr Phe Ile Lys Ile Pro Val Asn Glu Ala Gly Leu Ala Ala
                85                  90                  95

Ile Lys Gln Leu Lys Gln Ala Asn Tyr Arg Ile Thr Ala Thr Ala Ile
            100                 105                 110

Tyr Thr Glu Phe Gln Gly Tyr Leu Ala Ile Ala Ala Gly Ala Asp Tyr
        115                 120                 125

Leu Ala Pro Tyr Tyr Asn Arg Met Glu Asn Leu Thr Ile Asp Ser Gln
130                 135                 140

Lys Val Ile Glu His Leu Ala Ala Glu Ile Lys Arg Thr Asn Ala Lys
145                 150                 155                 160

Ser Lys Ile Leu Ala Ala Ser Phe Lys Asn Val Ala Gln Ile Asn Gln
                165                 170                 175

Ala Cys Gln Met Gly Ala Gln Ala Val Thr Ile Ala Pro Glu Leu Val
            180                 185                 190

Thr Gln Gly Leu Ala Met Pro Ala Ile Gln Lys Ala Val Thr Asp Phe
        195                 200                 205

Gln Glu Asp Trp Val Ala Val Phe Gly Val Thr Val Asn Glu Leu
    210                 215                 220

Ala
225

<210> SEQ ID NO 19
<211> LENGTH: 222
<212> TYPE: PRT
<213> ORGANISM: Streptococcus suis

<400> SEQUENCE: 19

Met Glu Phe Met Leu Asp Thr Leu Asn Ile Glu Glu Ile Arg Lys Trp
1               5                   10                  15

Ala Glu Val Leu Pro Leu Ala Gly Val Thr Ser Asn Pro Thr Ile Ala
            20                  25                  30

Arg Lys Glu Gly Asp Ile Asp Phe Glu Arg Leu His Leu Ile Arg
        35                  40                  45

```
Asp Ile Ile Gly Pro Asn Ala Ser Leu His Val Gln Val Ala Lys
             50                  55                  60

Asp Tyr Glu Gly Ile Leu Ala Asp Ala Lys Lys Ile Arg Glu Leu Ala
 65                  70                  75                  80

Pro Glu Asn Ile Tyr Ile Lys Val Pro Val Thr Pro Ala Gly Leu Ala
                 85                  90                  95

Ala Met Lys Thr Leu Lys Ala Gln Gly Tyr Gln Ile Thr Ala Thr Ala
            100                 105                 110

Ile Tyr Thr Val Phe Gln Gly Leu Leu Ala Ile Glu Ala Gly Ala Asp
            115                 120                 125

Tyr Leu Ala Pro Tyr Tyr Asn Arg Met Ala Asn Leu Asn Ile Asp Ser
    130                 135                 140

Asn Ala Val Ile Ala Gln Leu Ser Glu Ala Ile Asp Arg Glu Cys Ser
145                 150                 155                 160

Glu Ser Lys Ile Leu Ala Ala Ser Phe Lys Asn Val Asp Gln Val Asn
                165                 170                 175

Gln Ala Phe Ala Asn Gly Ala Gln Ala Ile Thr Ala Gly Ala Asp Ile
            180                 185                 190

Phe Glu Ala Ala Phe Ser Met Pro Ser Ile Gln Lys Ala Val Asn Asp
    195                 200                 205

Phe Ala Asp Asp Trp Ser Ala Ile His Gly Arg Tyr Thr Ile
210                 215                 220

<210> SEQ ID NO 20
<211> LENGTH: 222
<212> TYPE: PRT
<213> ORGANISM: Streptococcus pneumoniae

<400> SEQUENCE: 20

Met Glu Phe Met Leu Asp Thr Leu Asn Leu Asp Glu Ile Lys Lys Trp
  1               5                  10                  15

Ser Glu Ile Leu Pro Leu Ala Gly Val Thr Ser Asn Pro Thr Ile Ala
             20                  25                  30

Lys Arg Glu Gly Ser Ile Asn Phe Phe Glu Arg Ile Lys Asp Val Arg
         35                  40                  45

Glu Leu Ile Gly Ser Thr Pro Ser Ile His Val Gln Val Ile Ser Gln
 50                  55                  60

Asp Phe Glu Gly Ile Leu Lys Asp Ala His Lys Ile Arg Arg Gln Ala
 65                  70                  75                  80

Gly Asp Asp Ile Phe Ile Lys Val Pro Val Thr Pro Ala Gly Leu Arg
                 85                  90                  95

Ala Ile Lys Ala Leu Lys Lys Glu Gly Tyr His Ile Thr Ala Thr Ala
            100                 105                 110

Ile Tyr Thr Val Ile Gln Gly Leu Leu Ala Ile Glu Ala Gly Ala Asp
            115                 120                 125

Tyr Leu Ala Pro Tyr Tyr Asn Arg Met Glu Asn Leu Asn Ile Asp Ser
    130                 135                 140

Asn Ser Val Ile Arg Gln Leu Ala Leu Ala Ile Asp Arg Gln Asn Ser
145                 150                 155                 160

Pro Ser Lys Ile Leu Ala Ala Ser Phe Lys Asn Val Ala Gln Val Asn
                165                 170                 175

Asn Ala Leu Ala Ala Gly Ala His Ala Val Thr Ala Gly Ala Asp Val
            180                 185                 190

Phe Glu Ser Ala Phe Ala Met Pro Ser Ile Gln Lys Ala Val Asp Asp
```

```
                195                 200                 205
Phe Ser Asp Asp Trp Phe Val Thr Gln Asn Ser Arg Ser Ile
    210                 215                 220

<210> SEQ ID NO 21
<211> LENGTH: 241
<212> TYPE: PRT
<213> ORGANISM: Pyrococcus horikoshii
<220> FEATURE:
<221> NAME/KEY: misc_feature
<223> OTHER INFORMATION: strain ATCC 700860 / DSM 12428 / JCM 9974 /
      NBRC 100139 / OT-3

<400> SEQUENCE: 21

Met Val Lys Val Ile Phe Asp Leu Asp Asp Thr Leu Val Asp Thr
1               5                   10                  15

Ser Lys Leu Ala Glu Ile Ala Arg Lys Asn Ala Ile Glu Asn Met Ile
                20                  25                  30

Arg His Gly Leu Pro Val Asp Phe Glu Thr Ala Tyr Ser Glu Leu Ile
            35                  40                  45

Glu Leu Ile Lys Glu Tyr Gly Ser Asn Phe Pro Tyr His Phe Asp Tyr
        50                  55                  60

Leu Leu Arg Arg Leu Asp Leu Pro Tyr Asn Pro Lys Trp Ile Ser Ala
65                  70                  75                  80

Gly Val Ile Ala Tyr His Asn Thr Lys Phe Ala Tyr Leu Arg Glu Val
                85                  90                  95

Pro Gly Ala Arg Lys Val Leu Ile Arg Leu Lys Glu Leu Gly Tyr Glu
            100                 105                 110

Leu Gly Ile Ile Thr Asp Gly Asn Pro Val Lys Gln Trp Glu Lys Ile
        115                 120                 125

Leu Arg Leu Glu Leu Asp Asp Phe Phe Glu His Val Ile Ile Ser Asp
    130                 135                 140

Phe Glu Gly Val Lys Lys Pro His Pro Lys Ile Phe Lys Lys Ala Leu
145                 150                 155                 160

Lys Ala Phe Asn Val Lys Pro Glu Glu Ala Leu Met Val Gly Asp Arg
                165                 170                 175

Leu Tyr Ser Asp Ile Tyr Gly Ala Lys Arg Val Gly Met Lys Thr Val
            180                 185                 190

Trp Phe Arg Tyr Gly Lys His Ser Glu Arg Glu Leu Glu Tyr Arg Lys
        195                 200                 205

Tyr Ala Asp Tyr Glu Ile Asp Asn Leu Glu Ser Leu Leu Glu Val Leu
    210                 215                 220

Ala Arg Glu Ser Ser Ser Asn Lys Lys Val His Pro Pro Arg Gln Gln
225                 230                 235                 240

Ile

<210> SEQ ID NO 22
<211> LENGTH: 228
<212> TYPE: PRT
<213> ORGANISM: Methanocaldococcus jannaschii
<220> FEATURE:
<221> NAME/KEY: misc_feature
<223> OTHER INFORMATION: strain ATCC 43067 / DSM 2661 / JAL-1 / JCM
      10045 / NBRC 100440

<400> SEQUENCE: 22

Met Ile Lys Gly Ile Leu Phe Asp Leu Asp Asp Thr Leu Tyr Asn Ser
1               5                   10                  15
```

```
Ser Glu Phe Val Glu Ile Ala Arg Arg Glu Ala Val Lys Ser Met Ile
                20                  25                  30

Asp Ala Gly Leu Asn Ile Asp Phe Glu Glu Ala Met Asn Ile Leu Asn
            35                  40                  45

Lys Ile Ile Lys Asp Lys Gly Ser Asn Tyr Gly Lys His Phe Asp Asp
 50                  55                  60

Leu Val Lys Ala Val Leu Gly Lys Tyr Asp Pro Lys Ile Ile Thr Thr
 65                  70                  75                  80

Gly Ile Ile Thr Tyr His Asn Val Lys Val Ala Leu Leu Arg Pro Tyr
                85                  90                  95

Pro His Thr Ile Lys Thr Leu Met Glu Leu Lys Ala Met Gly Leu Lys
               100                 105                 110

Leu Gly Val Ile Thr Asp Gly Leu Thr Ile Lys Gln Trp Glu Lys Leu
            115                 120                 125

Ile Arg Leu Gly Ile His Pro Phe Phe Asp Asp Val Ile Thr Ser Glu
130                 135                 140

Glu Phe Gly Leu Gly Lys Pro His Leu Glu Phe Phe Lys Tyr Gly Leu
145                 150                 155                 160

Lys Arg Met Gly Leu Lys Ala Glu Glu Thr Val Tyr Val Gly Asp Arg
                165                 170                 175

Val Asp Lys Asp Ile Lys Pro Ala Lys Glu Leu Gly Met Ile Thr Val
            180                 185                 190

Arg Ile Leu Lys Gly Lys Tyr Lys Asp Met Glu Asp Glu Tyr Ser
                195                 200                 205

Asp Tyr Thr Ile Asn Ser Leu Gln Glu Leu Val Asp Ile Val Lys Asn
210                 215                 220

Leu Lys Lys Asp
225

<210> SEQ ID NO 23
<211> LENGTH: 222
<212> TYPE: PRT
<213> ORGANISM: Escherichia coli (strain K12)

<400> SEQUENCE: 23

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
            35                  40                  45

Thr Leu Gly Leu Arg Ile Asp Met Val Val Asp Leu Trp Tyr Ala Arg
 50                  55                  60

Gln Pro Trp Asn Gly Pro Ser Arg Gln Glu Val Glu Arg Val Ile
 65                  70                  75                  80

Ala Arg Ala Ile Ser Leu Val Glu Glu Thr Arg Pro Leu Leu Pro Gly
                85                  90                  95

Val Arg Glu Ala Val Ala Leu Cys Lys Glu Gln Gly Leu Leu Val Gly
            100                 105                 110

Leu Ala Ser Ala Ser Pro Leu His Met Leu Glu Lys Val Leu Thr Met
            115                 120                 125

Phe Asp Leu Arg Asp Ser Phe Asp Ala Leu Ala Ser Ala Glu Lys Leu
130                 135                 140

Pro Tyr Ser Lys Pro His Pro Gln Val Tyr Leu Asp Cys Ala Ala Lys
145                 150                 155                 160
```

```
Leu Gly Val Asp Pro Leu Thr Cys Val Ala Leu Glu Asp Ser Val Asn
            165                 170                 175

Gly Met Ile Ala Ser Lys Ala Ala Arg Met Arg Ser Ile Val Val Pro
            180                 185                 190

Ala Pro Glu Ala Gln Asn Asp Pro Arg Phe Val Leu Ala Asp Val Lys
            195                 200                 205

Leu Ser Ser Leu Thr Glu Leu Thr Ala Lys Asp Leu Leu Gly
            210                 215                 220

<210> SEQ ID NO 24
<211> LENGTH: 359
<212> TYPE: PRT
<213> ORGANISM: Escherichia coli (strain K12)

<400> SEQUENCE: 24

Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
    210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255

His Asn Ser Leu Asn Phe Val Phe His Gly Gly Ser Gly Ser Thr Ala
            260                 265                 270

Gln Glu Ile Lys Asp Ser Val Ser Tyr Gly Val Val Lys Met Asn Ile
        275                 280                 285

Asp Thr Asp Thr Gln Trp Ala Thr Trp Glu Gly Val Leu Asn Tyr Tyr
    290                 295                 300

Lys Ala Asn Glu Ala Tyr Leu Gln Gly Gln Leu Gly Asn Pro Lys Gly
```

```
            305                 310                 315                 320
        Glu Asp Gln Pro Asn Lys Lys Tyr Tyr Asp Pro Arg Val Trp Leu Arg
                        325                 330                 335

Ala Gly Gln Thr Ser Met Ile Ala Arg Leu Glu Lys Ala Phe Gln Glu
                        340                 345                 350

Leu Asn Ala Ile Asp Val Leu
                        355

<210> SEQ ID NO 25
<211> LENGTH: 350
<212> TYPE: PRT
<213> ORGANISM: Escherichia coli (strain K12)

<400> SEQUENCE: 25

Met Thr Asp Ile Ala Gln Leu Leu Gly Lys Asp Ala Asp Asn Leu Leu
        1               5                   10                  15

Gln His Arg Cys Met Thr Ile Pro Ser Asp Gln Leu Tyr Leu Pro Gly
                        20                  25                  30

His Asp Tyr Val Asp Arg Val Met Ile Asp Asn Asn Arg Pro Pro Ala
                        35                  40                  45

Val Leu Arg Asn Met Gln Thr Leu Tyr Asn Thr Gly Arg Leu Ala Gly
                50                  55                  60

Thr Gly Tyr Leu Ser Ile Leu Pro Val Asp Gln Gly Val Glu His Ser
        65                  70                  75                  80

Ala Gly Ala Ser Phe Ala Ala Asn Pro Leu Tyr Phe Asp Pro Lys Asn
                        85                  90                  95

Ile Val Glu Leu Ala Ile Glu Ala Gly Cys Asn Cys Val Ala Ser Thr
                        100                 105                 110

Tyr Gly Val Leu Ala Ser Val Ser Arg Arg Tyr Ala His Arg Ile Pro
                        115                 120                 125

Phe Leu Val Lys Leu Asn His Asn Glu Thr Leu Ser Tyr Pro Asn Thr
                        130                 135                 140

Tyr Asp Gln Thr Leu Tyr Ala Ser Val Glu Gln Ala Phe Asn Met Gly
        145                 150                 155                 160

Ala Val Ala Val Gly Ala Thr Ile Tyr Phe Gly Ser Glu Glu Ser Arg
                        165                 170                 175

Arg Gln Ile Glu Glu Ile Ser Ala Ala Phe Glu Arg Ala His Glu Leu
                        180                 185                 190

Gly Met Val Thr Val Leu Trp Ala Tyr Leu Arg Asn Ser Ala Phe Lys
                        195                 200                 205

Lys Asp Gly Val Asp Tyr His Val Ser Ala Asp Leu Thr Gly Gln Ala
                        210                 215                 220

Asn His Leu Ala Ala Thr Ile Gly Ala Asp Ile Val Lys Gln Lys Met
        225                 230                 235                 240

Ala Glu Asn Asn Gly Gly Tyr Lys Ala Ile Asn Tyr Gly Tyr Thr Asp
                        245                 250                 255

Asp Arg Val Tyr Ser Lys Leu Thr Ser Glu Asn Pro Ile Asp Leu Val
                        260                 265                 270

Arg Tyr Gln Leu Ala Asn Cys Tyr Met Gly Arg Ala Gly Leu Ile Asn
                        275                 280                 285

Ser Gly Gly Ala Ala Gly Gly Glu Thr Asp Leu Ser Asp Ala Val Arg
                290                 295                 300

Thr Ala Val Ile Asn Lys Arg Ala Gly Gly Met Gly Leu Ile Leu Gly
        305                 310                 315                 320
```

```
Arg Lys Ala Phe Lys Ser Met Ala Asp Gly Val Lys Leu Ile Asn
                325                 330                 335

Ala Val Gln Asp Val Tyr Leu Asp Ser Lys Ile Thr Ile Ala
            340                 345                 350
```

<210> SEQ ID NO 26
<211> LENGTH: 364
<212> TYPE: PRT
<213> ORGANISM: Homo sapiens

<400> SEQUENCE: 26

```
Met Ala His Arg Phe Pro Ala Leu Thr Gln Glu Gln Lys Lys Glu Leu
1               5                   10                  15

Ser Glu Ile Ala Gln Ser Ile Val Ala Asn Gly Lys Gly Ile Leu Ala
            20                  25                  30

Ala Asp Glu Ser Val Gly Thr Met Gly Asn Arg Leu Gln Arg Ile Lys
        35                  40                  45

Val Glu Asn Thr Glu Glu Asn Arg Arg Gln Phe Arg Glu Ile Leu Phe
    50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
    130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
        195                 200                 205

Val Leu Ala Ala Val Tyr Lys Ala Leu Asn Asp His His Val Tyr Leu
    210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
        275                 280                 285

Leu Cys Pro Leu Pro Lys Pro Trp Lys Leu Ser Phe Ser Tyr Gly Arg
    290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335

Gln Ala Ala Lys Gly Gln Tyr Val His Thr Gly Ser Ser Gly Ala Ala
            340                 345                 350
```

```
Ser Thr Gln Ser Leu Phe Thr Ala Cys Tyr Thr Tyr
        355                 360

<210> SEQ ID NO 27
<211> LENGTH: 364
<212> TYPE: PRT
<213> ORGANISM: Homo sapiens

<400> SEQUENCE: 27

Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
    210                 215                 220

Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
                245                 250                 255

Leu Arg Arg Thr Val Pro Pro Ala Val Thr Gly Ile Thr Phe Leu Ser
            260                 265                 270

Gly Gly Gln Ser Glu Glu Glu Ala Ser Ile Asn Leu Asn Ala Ile Asn
        275                 280                 285

Lys Cys Pro Leu Leu Lys Pro Trp Ala Leu Thr Phe Ser Tyr Gly Arg
    290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
            340                 345                 350

Ala Ser Glu Ser Leu Phe Val Ser Asn His Ala Tyr
```

<210> SEQ ID NO 28
<211> LENGTH: 364
<212> TYPE: PRT
<213> ORGANISM: Homo sapiens

<400> SEQUENCE: 28

Met Pro His Ser Tyr Pro Ala Leu Ser Ala Glu Gln Lys Lys Glu Leu
1               5                   10                  15

Ser Asp Ile Ala Leu Arg Ile Val Ala Pro Gly Lys Gly Ile Leu Ala
            20                  25                  30

Ala Asp Glu Ser Val Gly Ser Met Ala Lys Arg Leu Ser Gln Ile Gly
        35                  40                  45

Val Glu Asn Thr Glu Glu Asn Arg Arg Leu Tyr Arg Gln Val Leu Phe
    50                  55                  60

Ser Ala Asp Asp Arg Val Lys Lys Cys Ile Gly Gly Val Ile Phe Phe
65                  70                  75                  80

His Glu Thr Leu Tyr Gln Lys Asp Asp Asn Gly Val Pro Phe Val Arg
                85                  90                  95

Thr Ile Gln Asp Lys Gly Ile Val Val Gly Ile Lys Val Asp Lys Gly
            100                 105                 110

Val Val Pro Leu Ala Gly Thr Asp Gly Glu Thr Thr Thr Gln Gly Leu
        115                 120                 125

Asp Gly Leu Ser Glu Arg Cys Ala Gln Tyr Lys Lys Asp Gly Ala Asp
130                 135                 140

Phe Ala Lys Trp Arg Cys Val Leu Lys Ile Ser Glu Arg Thr Pro Ser
145                 150                 155                 160

Ala Leu Ala Ile Leu Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Val Tyr Leu
    210                 215                 220

Glu Gly Thr Leu Leu Lys Pro Asn Met Val Thr Pro Gly His Ala Cys
225                 230                 235                 240

Pro Ile Lys Tyr Thr Pro Glu Ile Ala Met Ala Thr Val Thr Ala
                245                 250                 255

Leu Arg Arg Thr Val Pro Pro Ala Val Pro Gly Val Thr Phe Leu Ser
            260                 265                 270

Gly Gly Gln Ser Glu Glu Glu Ala Ser Phe Asn Leu Asn Ala Ile Asn
        275                 280                 285

Arg Cys Pro Leu Pro Arg Pro Trp Ala Leu Thr Phe Ser Tyr Gly Arg
    290                 295                 300

Ala Leu Gln Ala Ser Ala Leu Asn Ala Trp Arg Gly Gln Arg Asp Asn
305                 310                 315                 320

Ala Gly Ala Ala Thr Glu Glu Phe Ile Lys Arg Ala Glu Val Asn Gly
                325                 330                 335

Leu Ala Ala Gln Gly Lys Tyr Glu Gly Ser Gly Glu Asp Gly Gly Ala
            340                 345                 350

Ala Ala Gln Ser Leu Tyr Ile Ala Asn His Ala Tyr
        355                 360

```
<210> SEQ ID NO 29
<211> LENGTH: 549
<212> TYPE: PRT
<213> ORGANISM: Aeromonas hydrophila subsp. hydrophila
<220> FEATURE:
<221> NAME/KEY: misc_feature
<223> OTHER INFORMATION: strain ATCC 7966 / DSM 30187 / JCM 1027 / KCTC
      2358 / NCIMB 9240

<400> SEQUENCE: 29
```

Met Ala Gln His Ser His Ala Gly Gln Pro Ala Arg Leu Ser Asp Leu
1               5                   10                  15

Thr Asn Ile Pro Arg Leu Val Ser Ala Tyr Tyr Leu Asn Lys Pro Asp
            20                  25                  30

Met Ser Arg Pro Glu Gln Arg Val Ala Phe Gly Thr Ser Gly His Arg
        35                  40                  45

Gly Ser Ala Leu His Asn Ala Phe Thr Glu Ser His Ile Leu Ala Val
    50                  55                  60

Thr Gln Ala Leu Val Glu Tyr Arg Gln Gln Ala Gly Ile Thr Gly Pro
65                  70                  75                  80

Leu Phe Val Gly Met Asp Thr His Ala Leu Ser Glu Ser Ala Phe Ala
                85                  90                  95

Ser Ala Val Glu Val Leu Ala Ala Asn Gly Val Glu Thr Arg Ile Gln
            100                 105                 110

Ala Gly Leu Gly Phe Thr Pro Thr Pro Val Ile Ser His Ala Ile Leu
        115                 120                 125

Arg His Asn Ala Gly Lys Pro Ala Ala Arg Ala Asp Gly Val Val Ile
    130                 135                 140

Thr Pro Ser His Asn Pro Pro Glu Asp Gly Gly Phe Lys Tyr Asn Pro
145                 150                 155                 160

Pro His Gly Gly Pro Ala Glu Gly Glu Ile Thr Lys Trp Val Glu Asp
                165                 170                 175

Arg Ala Asn Ala Ile Leu Glu Ala Gly Leu Ala Gly Val Lys Arg Met
            180                 185                 190

Ala Phe Ala Glu Ala Leu Lys Ser Pro Phe Val Ala Leu His Asp Tyr
        195                 200                 205

Val Thr Pro Tyr Val Asp Asp Leu Lys Asn Val Leu Asp Met Asp Ala
    210                 215                 220

Ile Lys Gln Ala Gly Ile Lys Ile Gly Val Asp Pro Leu Gly Gly Ser
225                 230                 235                 240

Gly Val Ala Tyr Trp Asp Val Ile Ala Lys Thr Tyr Gly Leu Asn Ile
                245                 250                 255

Glu Val Val Asn Tyr Lys Val Asp Pro Thr Phe Ser Phe Met Thr Leu
            260                 265                 270

Asp Lys Asp Gly Lys Ile Arg Met Asp Cys Ser Ser Pro Phe Ala Met
        275                 280                 285

Ala Ser Leu Ile Ala Leu Lys Asp Lys Phe Asp Ile Ala Leu Gly Asn
    290                 295                 300

Asp Pro Asp Tyr Asp Arg His Gly Ile Val Thr Lys Ser Gly Leu Met
305                 310                 315                 320

Asn Pro Asn His Tyr Leu Ala Val Ala Ile Gln Tyr Leu Phe Thr His
                325                 330                 335

Arg Thr Gly Trp Ser Lys Glu Ser Ala Val Gly Lys Thr Leu Val Ser
            340                 345                 350

Ser Ser Met Ile Asp Arg Val Ala Gly Glu Ile Gly Arg Thr Leu Lys

-continued

```
            355                 360                 365
Glu Val Pro Val Gly Phe Lys Trp Phe Val Asp Gly Leu Tyr Ser Gly
        370                 375                 380

Glu Phe Gly Phe Gly Gly Glu Ser Ala Gly Ala Ser Phe Leu Arg
385                 390                 395                 400

Lys Asp Gly Thr Val Trp Thr Thr Asp Lys Asp Gly Phe Ile Leu Ala
                    405                 410                 415

Leu Leu Ala Ala Glu Ile Leu Ala Val Thr Gly Lys Asp Pro Gln Thr
                420                 425                 430

His Tyr Asp Ala Leu Glu Ala Lys Phe Gly Arg Ser Ser Tyr Arg Arg
            435                 440                 445

Ile Asp Ala Pro Ala Asn Ser Ala Gln Lys Ala Val Leu Ser Lys Leu
        450                 455                 460

Asp Pro Ala Leu Val Glu Ala Ser Thr Leu Ala Gly Glu Pro Ile Ile
465                 470                 475                 480

Ala Lys Leu Thr Lys Ala Pro Gly Asn Asp Ala Ala Ile Gly Gly Leu
                    485                 490                 495

Lys Val Val Thr Glu Asn Gly Trp Phe Ala Ala Arg Pro Ser Gly Thr
                500                 505                 510

Glu Ser Ile Tyr Lys Ile Tyr Met Glu Ser Phe Lys Gly Glu Ala His
            515                 520                 525

Leu Asp Leu Ile Gln Gln Glu Ala Gln Gln Ile Val Ser Ala Ala Leu
        530                 535                 540

Ala Lys Ala Gly Val
545

<210> SEQ ID NO 30
<211> LENGTH: 454
<212> TYPE: PRT
<213> ORGANISM: Aeromonas hydrophila subsp. hydrophila
<220> FEATURE:
<221> NAME/KEY: misc_feature
<223> OTHER INFORMATION: strain ATCC 7966 / DSM 30187 / JCM 1027 / KCTC
      2358 / NCIMB 9240

<400> SEQUENCE: 30

Met Asn Leu Thr Cys Phe Lys Ala Tyr Asp Ile Arg Gly Lys Leu Gly
1               5                   10                  15

Asp Glu Leu Asn Ile Glu Ile Ala Tyr Arg Ile Gly Arg Ala Thr Ala
            20                  25                  30

Gln Tyr Leu Lys Ala Thr Arg Ile Ala Val Gly Gly Asp Val Arg Leu
        35                  40                  45

Thr Ser Glu Gly Leu Lys Gln Ala Leu Ala Asn Gly Ile Leu Asp Ala
    50                  55                  60

Gly Cys Asp Val Ile Asp Leu Gly Val Thr Gly Thr Glu Glu Thr Tyr
65                  70                  75                  80

Phe Ala Ala Phe Thr Leu Asp Ile Asp Gly Ala Ile Glu Val Thr Ala
                85                  90                  95

Ser His Asn Pro Met Asp Tyr Asn Gly Met Lys Leu Val Gly Arg Asp
            100                 105                 110

Ala Cys Pro Ile Ser Gly Asp Ser Gly Leu Asn Asp Ile Arg Ala Leu
        115                 120                 125

Ala Glu Lys Gly Asp Phe Ser Val Ser Phe Arg Arg Gly Thr Leu Ser
    130                 135                 140

Lys Lys Ser Ile Leu Asp Ala Tyr Val Asp His Leu Leu Thr Tyr Ile
145                 150                 155                 160
```

Lys Pro His Gln Leu Arg Pro Lys Leu Val Val Asn Ala Gly Asn
                165                 170                 175

Gly Ala Ala Gly His Val Ile Asp Val Ile Glu Gln Arg Phe Asn Ile
            180                 185                 190

Leu Asn Ile Pro Val Glu Phe Ile Lys Ile His His Glu Glu Asn Gly
            195                 200                 205

Asn Phe Pro Asn Gly Ile Pro Asn Pro Leu Pro Glu Asn Arg Asp
210                 215                 220

Val Thr Ser Glu Ala Val Lys Leu His His Ala Asp Met Gly Ile Ala
225                 230                 235                 240

Trp Asp Gly Asp Phe Asp Arg Cys Phe Leu Asp Glu Asn Gly Ile
                245                 250                 255

Phe Ile Glu Gly Tyr Tyr Ile Val Gly Leu Leu Ala Glu Ala Phe Leu
            260                 265                 270

Val Glu Asn Pro His Glu Arg Ile Ile His Asp Pro Arg Leu Thr Trp
            275                 280                 285

Asn Thr Ile Asp Ile Val Glu Lys Ser Gly Gly Ile Pro Val Gln Ser
            290                 295                 300

Lys Thr Gly His Ala Phe Ile Lys Glu Arg Met Arg Ser Glu Asn Ala
305                 310                 315                 320

Ile Tyr Gly Gly Glu Met Ser Ala His His Tyr Phe Arg Asp Phe Gly
                325                 330                 335

Tyr Cys Asp Ser Gly Met Ile Pro Trp Leu Leu Val Ile Asn Leu Leu
            340                 345                 350

Ser Leu Lys Asn Ser Thr Leu Ser Leu Val Ala Glu Arg Val Lys
            355                 360                 365

Ala Tyr Pro Cys Ser Gly Glu Ile Asn Tyr Arg Val Asp Asn Ala Leu
370                 375                 380

Glu Ile Ile Lys Lys Leu Glu Glu Val Tyr Val Pro Leu Ala Val Lys
385                 390                 395                 400

Val Glu Tyr Val Asp Gly Leu Ser Ile Glu Met Asn Asp Trp Arg Phe
                405                 410                 415

Asn Val Arg Ile Ser Asn Thr Glu Pro Leu Leu Arg Leu Asn Val Glu
            420                 425                 430

Ser Lys Asn Asn Ile Ser Lys Leu Thr Ser Gly Leu Asn Ser Leu His
            435                 440                 445

Lys Met Ile Asn Asn Ile
            450

<210> SEQ ID NO 31
<211> LENGTH: 222
<212> TYPE: PRT
<213> ORGANISM: Streptococcus agalactiae serotype III
<220> FEATURE:
<221> NAME/KEY: misc_feature
<223> OTHER INFORMATION: strain NEM316

<400> SEQUENCE: 31

Met Glu Phe Leu Leu Asp Thr Leu Asn Leu Glu Ala Ile Lys Lys Trp
1               5                   10                  15

His His Ile Leu Pro Leu Ala Gly Val Thr Ser Asn Pro Thr Ile Ala
            20                  25                  30

Lys Lys Glu Gly Asp Ile His Phe Phe Gln Arg Ile Arg Asp Val Arg
        35                  40                  45

Glu Ile Ile Gly Arg Glu Ala Ser Leu His Val Gln Val Val Ala Lys

```
            50                  55                  60
Asp Tyr Gln Gly Ile Leu Asp Ala Ala Lys Ile Arg Gln Glu Thr
 65                  70                  75                  80

Asp Asp Asp Ile Tyr Ile Lys Val Pro Val Thr Pro Asp Gly Leu Ala
                 85                  90                  95

Ala Ile Lys Thr Leu Lys Ala Glu Gly Tyr Asn Ile Thr Ala Thr Ala
                100                 105                 110

Ile Tyr Thr Ser Met Gln Gly Leu Leu Ala Ile Ser Ala Gly Ala Asp
                115                 120                 125

Tyr Leu Ala Pro Tyr Phe Asn Arg Met Glu Asn Leu Asp Ile Asp Ala
            130                 135                 140

Thr Gln Val Ile Lys Glu Leu Ala Gln Ala Ile Glu Arg Thr Gly Ser
145                 150                 155                 160

Ser Ser Lys Ile Leu Ala Ala Ser Phe Lys Asn Ala Ser Gln Val Thr
                165                 170                 175

Lys Ala Leu Ser Gln Gly Ala Gln Ser Ile Thr Ala Gly Pro Asp Ile
                180                 185                 190

Phe Glu Ser Val Phe Ala Met Pro Ser Ile Ala Lys Ala Val Asn Asp
            195                 200                 205

Phe Ala Asp Asp Trp Lys Ala Ser Gln His Ser Glu His Ile
            210                 215                 220

<210> SEQ ID NO 32
<211> LENGTH: 546
<212> TYPE: PRT
<213> ORGANISM: E.coli

<400> SEQUENCE: 32

Met Ala Ile His Asn Arg Ala Gly Gln Pro Ala Gln Gln Ser Asp Leu
 1               5                  10                  15

Ile Asn Val Ala Gln Leu Thr Ala Gln Tyr Tyr Val Leu Lys Pro Glu
                20                  25                  30

Ala Gly Asn Ala Glu His Ala Val Lys Phe Gly Thr Ser Gly His Arg
            35                  40                  45

Gly Ser Ala Ala Arg His Ser Phe Asn Glu Pro His Ile Leu Ala Ile
 50                  55                  60

Ala Gln Ala Ile Ala Glu Glu Arg Ala Lys Asn Gly Ile Thr Gly Pro
 65                  70                  75                  80

Cys Tyr Val Gly Lys Asp Thr His Ala Leu Ser Glu Pro Ala Phe Ile
                 85                  90                  95

Ser Val Leu Glu Val Leu Ala Ala Asn Gly Val Asp Val Ile Val Gln
                100                 105                 110

Glu Asn Asn Gly Phe Thr Pro Thr Pro Ala Val Ser Asn Ala Ile Leu
            115                 120                 125

Val His Asn Lys Lys Gly Gly Pro Leu Ala Asp Gly Ile Val Ile Thr
            130                 135                 140

Pro Ser His Asn Pro Pro Glu Asp Gly Gly Ile Lys Tyr Asn Pro Pro
145                 150                 155                 160

Asn Gly Gly Pro Ala Asp Thr Asn Val Thr Lys Val Val Glu Asp Arg
                165                 170                 175

Ala Asn Ala Leu Leu Ala Asp Gly Leu Lys Gly Val Lys Arg Ile Ser
                180                 185                 190

Leu Asp Glu Ala Met Ala Ser Gly His Val Lys Glu Gln Asp Leu Val
            195                 200                 205
```

Gln Pro Phe Val Glu Gly Leu Ala Asp Ile Val Asp Met Ala Ala Ile
210                 215                 220

Gln Lys Ala Gly Leu Thr Leu Gly Val Asp Pro Leu Gly Gly Ser Gly
225                 230                 235                 240

Ile Glu Tyr Trp Lys Arg Ile Gly Glu Tyr Tyr Asn Leu Asn Leu Thr
                245                 250                 255

Ile Val Asn Asp Gln Val Asp Gln Thr Phe Arg Phe Met His Leu Asp
            260                 265                 270

Lys Asp Gly Ala Ile Arg Met Asp Cys Ser Ser Glu Cys Ala Met Ala
        275                 280                 285

Gly Leu Leu Ala Leu Arg Asp Lys Phe Asp Leu Ala Phe Ala Asn Asp
    290                 295                 300

Pro Asp Tyr Asp Arg His Gly Ile Val Thr Pro Ala Gly Leu Met Asn
305                 310                 315                 320

Pro Asn His Tyr Leu Ala Val Ala Ile Asn Tyr Leu Phe Gln His Arg
                325                 330                 335

Pro Gln Trp Gly Lys Asp Val Ala Val Gly Lys Thr Leu Val Ser Ser
            340                 345                 350

Ala Met Ile Asp Arg Val Val Asn Asp Leu Gly Arg Lys Leu Val Glu
        355                 360                 365

Val Pro Val Gly Phe Lys Trp Phe Val Asp Gly Leu Phe Asp Gly Ser
    370                 375                 380

Phe Gly Phe Gly Gly Glu Ser Ala Gly Ala Ser Phe Leu Arg Phe
385                 390                 395                 400

Asp Gly Thr Pro Trp Ser Thr Asp Lys Asp Gly Ile Ile Met Cys Leu
                405                 410                 415

Leu Ala Ala Glu Ile Thr Ala Val Thr Gly Lys Asn Pro Gln Glu His
            420                 425                 430

Tyr Asn Glu Leu Ala Lys Arg Phe Gly Ala Pro Ser Tyr Asn Arg Leu
        435                 440                 445

Gln Ala Ala Ala Thr Ser Ala Gln Lys Ala Ala Leu Ser Lys Leu Ser
    450                 455                 460

Pro Glu Met Val Ser Ala Ser Thr Leu Ala Gly Asp Pro Ile Thr Ala
465                 470                 475                 480

Arg Leu Thr Ala Ala Pro Gly Asn Gly Ala Ser Ile Gly Gly Leu Lys
                485                 490                 495

Val Met Thr Asp Asn Gly Trp Phe Ala Ala Arg Pro Ser Gly Thr Glu
            500                 505                 510

Asp Ala Tyr Lys Ile Tyr Cys Glu Ser Phe Leu Gly Glu Glu His Arg
        515                 520                 525

Lys Gln Ile Glu Lys Glu Ala Val Glu Ile Val Ser Glu Val Leu Lys
    530                 535                 540

Asn Ala
545

<210> SEQ ID NO 33
<211> LENGTH: 219
<212> TYPE: PRT
<213> ORGANISM: E.coli

<400> SEQUENCE: 33

Met Lys Leu Gln Gly Val Ile Phe Asp Leu Asp Gly Val Ile Thr Asp
1               5                   10                  15

Thr Ala His Leu His Phe Gln Ala Trp Gln Gln Ile Ala Ala Glu Ile
            20                  25                  30

Gly Ile Ser Ile Asp Ala Gln Phe Asn Glu Ser Leu Lys Gly Ile Ser
            35                  40                  45

Arg Asp Glu Ser Leu Arg Arg Ile Leu Gln His Gly Gly Lys Glu Gly
        50                  55                  60

Asp Phe Asn Ser Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Ser Leu Leu Ala Asp Leu Arg Ala Gln Gln Ile Ser Val
            100                 105                 110

Gly Leu Ala Ser Val Ser Leu Asn Ala Pro Thr Ile Leu Ala Ala Leu
        115                 120                 125

Glu Leu Arg Glu Phe Phe Thr Phe Cys Ala Asp Ala Ser Gln Leu Lys
    130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
            180                 185                 190

Gly Leu Thr Gly Ala Gln Leu Leu Pro Ser Thr Glu Ser Leu Thr
        195                 200                 205

Trp Pro Arg Leu Ser Ala Phe Trp Gln Asn Val
210                 215

<210> SEQ ID NO 34
<211> LENGTH: 663
<212> TYPE: DNA
<213> ORGANISM: E.coli

<400> SEQUENCE: 34
atggaactgt atctggatac ttcagacgtt gttgcggtga aggcgctgtc acgtattttt     60
ccgctggcgg tgtgaccac taacccaagc attatcgccg cgggtaaaaa accgctggat    120
gttgtgcttc cgcaacttca tgaagcgatg ggcggtcagg ggcgtctgtt tgcccaggta    180
atggctacca ctgccgaagg gatggttaat gacgcgctta agctgcgttc tattattgcg    240
gatatcgtgg tgaaagttcc ggtgaccgcc gagggctgg cagctattaa gatgttaaaa    300
gcggaaggga ttccgacgct gggaaccgcg gtatatggcg cagcacaagg gctgctgtcg    360
gcgctggcag gtgcggaata tgttgcgcct tacgttaatc gtattgatgc tcagggcggt    420
agcggcattc agactgtgac cgacttacac cagttattga aaatgcatgc gccgcaggcg    480
aaagtgctgg cagcgagttt caaaaccccg cgtcaggcgc tggactgctt actggcagga    540
tgtgaatcaa ttactctgcc actggatgtg cacaacaga tgattagcta ccggcggtt    600 gatgccgctg tggcgaagtt tgagcaggac tggcagggag cgtttggcag aacgtcgatt    660
taa                                                                 663

<210> SEQ ID NO 35
<211> LENGTH: 726
<212> TYPE: DNA
<213> ORGANISM: E.coli

<400> SEQUENCE: 35
atgagaggat ctcaccatca ccatcaccat acggatccgg ccctgagggc cgaactgtat     60

```
ctggatactt cagacgttgt tgcggtgaag gcgctgtcac gtattttcc gctggcgggt    120 gtgaccacta acccaagcat tatcgccgcg ggtaaaaaac cgctggatgt tgtgcttccg    180
caacttcatg aagcgatggg cggtcagggg cgtctgtttg cccaggtaat ggctaccact    240
gccgaaggga tggttaatga cgcgcttaag ctgcgttcta ttattgcgga tatcgtggtg    300
aaagttccgg tgaccgccga ggggctggca gctattaaga tgttaaaagc ggaagggatt    360
ccgacgctgg gaaccgcggt atatggcgca gcacaagggc tgctgtcggc gctggcaggt    420
gcggaatatg ttagccctta cgttaatcgt attgatgctc agggcggtag cggcattcag    480
actgtgaccg acttacacca gttattgaaa atgcatgcgc gcaggcgaa agtgctggca    540 gcgagtttca aaccccgcg tcaggcgctg gactgcttac tggcaggatg tgaatcaatt    600
actctgccac tggatgtggc acaacagatg attagctatc cggcggttga tgccgctgtg    660
gcgaagtttg agcaggactg gcagggagcg tttggcagaa cgtcgattgg cctatgcgga    720
cgctaa                                                              726

<210> SEQ ID NO 36
<211> LENGTH: 663
<212> TYPE: DNA
<213> ORGANISM: E.coli

<400> SEQUENCE: 36
atggaactgt atctggacac cgctaacgtc gcagaagtcg aacgtctggc acgcatattc     60
cccattgccg gggtgacaac taacccgagc attatcgctg ccagcaagga gtccatatgg    120
gaagtgctgc cgcgtctgca aaaagcgatt ggtgatgagg cattctgtt tgctcagacc    180 atgagccgcg acgcgcaggg gatggtggaa gaagcgaagc gcctgcgcga cgctattccg    240
ggtattgtgt tgaaaatccc ggtgacttcc gaaggtctgg cagcaattaa aatactgaaa    300
aaagagggta ttactacact tggcactgct gtatatagcg ccgcacaagg gttattagcc    360
gcactggcag gggcaaaata cgttgctccg tatgttaacc gctagatgc ccagggcgga    420 gacggcattc gtacggttca ggagctgcaa acgctgttag aaatgcacgc gccagaaagc    480
atggtgctgg cagccagctt taaaacgccg cgtcaggcgc tggactgttt actggcagga    540
tgtgaatcca tcaccctgcc cttagatgta gcgcaacaaa tgctcaacac ccctgcggta    600
gagtcagcta tagagaagtt cgaacacgac tggaatgccg catttggcac tactcatctc    660
taa                                                                 663

<210> SEQ ID NO 37
<211> LENGTH: 954
<212> TYPE: DNA
<213> ORGANISM: E.coli

<400> SEQUENCE: 37
atgacggaca aattgacctc ccttcgtcag tacaccaccg tagtggccga cactggggac     60
atcgcggcaa tgaagctgta tcaaccgcag gatgccacaa ccaaccttc tctcattctt    120 aacgcagcgc agattccgga ataccgtaag ttgattgatg atgctgtcgc ctgggcgaaa    180
cagcagagca cgatcgcgc gcagcagatc gtggacgcga ccgacaaact ggcagtaaat    240
attggtctgg aaatcctgaa actggttccg ggccgtatct caactgaagt tgatgcgcgt    300
ctttcctatg acaccgaagc gtcaattgcg aaagcaaaac gcctgatcaa actctacaac    360
gatgctggta ttagcaacga tcgtattctg atcaaactgg cttctacctg gcagggtatc    420
cgtgctgcag aacagctgga aaaagaaggc atcaactgta acctgacccct gctgttctcc    480
```

```
ttcgctcagg ctcgtgcttg tgcggaagcg ggcgtgttcc tgatctcgcc gtttgttggc    540
cgtattcttg actggtacaa agcgaatacc gataagaaag agtacgctcc ggcagaagat    600
ccgggcgtgg tttctgtatc tgaaatctac cagtactaca agagcacgg ttatgaaacc     660 gtggttatgg gcgcaagctt ccgtaacatc ggcgaaattc tggaactggc aggctgcgac    720
cgtctgacca tcgcaccggc actgctgaaa gagctggcgg agagcgaagg ggctatcgaa    780
cgtaaactgt cttacaccgg cgaagtgaaa gcgcgtccgg cgcgtatcac tgagtccgag    840
ttcctgtggc agcacaacca ggatccaatg gcagtagata aactggcgga aggtatccgt    900
aagtttgcta ttgaccagga aaaactggaa aaaatgatcg gcgatctgct gtaa          954
```

<210> SEQ ID NO 38
<211> LENGTH: 954
<212> TYPE: DNA
<213> ORGANISM: E.coli

<400> SEQUENCE: 38

```
atgacggaca aattgacctc ccttcgtcag tacaccaccg tagtggccga cactggggac    60
atcgcggcaa tgaagctgta tcaaccgcag gatgccacaa ccaacccttc tctcattctt    120
aacgcagcgc agattccgga ataccgtaag ttgattgatg atgctgtcgc ctgggcgaaa    180
cagcagagca cgatcgcgc gcagcagatc gtggacgcga ccgacaaact ggcagtaaat    240
attggtctgg aaatcctgaa actggttccg ggccgtatct caactgaagt tgatgcgcgt    300
ctttcctatg acaccgaagc gtcaattgcg aaagcaaaac gcctgatcaa actctacaac    360
gatgctggta ttagcaacga tcgtattctg atcaaactgg cttctacctg caggggtatc    420
cgtgctgcag aacagctgga aaagaaggc atcaactgta acctgaccct gctgttctcc    480
ttcgctcagg ctcgtgcttg tgcggaagcg ggcgtgttcc tgatctcgcc gtatgttggc    540
cgtattcttg actggtacaa agcgaatacc gataagaaag agtacgctcc ggcagaagat    600
ccgggcgtgg tttctgtatc tgaaatctac cagtactaca agagcacgg ttatgaaacc     660 gtggttatgg gcgcaagctt ccgtaacatc ggcgaaattc tggaactggc aggctgcgac    720
cgtctgacca tcgcaccggc actgctgaaa gagctggcgg agagcgaagg ggctatcgaa    780
cgtaaactgt cttacaccgg cgaagtgaaa gcgcgtccgg cgcgtatcac tgagtccgag    840
ttcctgtggc agcacaacca ggatccaatg gcagtagata aactggcgga aggtatccgt    900
aagtttgcta ttgaccagga aaaactggaa aaaatgatcg gcgatctgct gtaa          954
```

<210> SEQ ID NO 39
<211> LENGTH: 816
<212> TYPE: DNA
<213> ORGANISM: E.coli

<400> SEQUENCE: 39

```
atgagcgtaa aagttatcgt cacagacatg gacggtactt tcttaacga cgccaaaacg     60 tacaaccaac cacgtttat ggcgcaatat caggaactga aaagcgcgg cattaagttc      120 gttgttgcca gcgtaatca gtattaccag cttatttcat ctttcctga gctaaaggat      180 gagatctctt ttgtcgcgga aaacggcgca ctggtttacg aacatggcaa gcagttgttc    240
cacggcgaac tgacccgaca tgaatcgcgg attgttattg gcgagttgct aaaagataag    300
caactcaatt ttgtcgcctg cggtctgcaa agtgcatatg tcagcgaaaa tgcccccgaa    360
gcatttgtcg cactgatggc aaaacactac catcgcctga acctgtaaa agattatcag    420
```

```
gagattgacg acgtactgtt caagttttcg ctcaacctgc cggatgaaca aatcccgtta    480
gtgatcgaca aactgcacgt agcgctcgat ggcattatga aacccgttac cagtggtttt    540
ggctttatcg acctgattat tcccggtcta cataaagcaa acggtatttc gcggttactg    600
aaacgctggg atctgtcacc gcaaaatgtg gtagcgattg cgacagcgg taacgatgcg     660 gagatgctga aaatggcgcg ttattccttt gcgatgggca atgctgcgga aaacattaaa    720
caaatcgccc gttacgctac cgatgataat aatcatgaag gcgcgctgaa tgtgattcag    780
gcggtgctgg ataacacatc cccttttaac agctga                             816

<210> SEQ ID NO 40
<211> LENGTH: 666
<212> TYPE: DNA
<213> ORGANISM: E.coli

<400> SEQUENCE: 40
atgtcccgga tagaagcggt atttttcgac tgcgacggta cgctggtcga cagtgaagtc     60
atttgctctc gcgcatatgt aacgatgttt caggaatttg gtattacgct cgatcctgaa    120
gaggtattca aacgtttcaa aggtgtaaaa ctgtacgaaa ttatcgatat tgtttccctt    180
gaacatggtg ttacgttagc gaaaacagaa gctgaacacg tttaccgtgc agaagtcgct    240
cggctgttcg attcagaact ggaagccatc gaaggggctg agcgctcct gtcagcgatc    300 actgcgccaa tgtgtgtggt atctaacggc ccaaataaca aaatgcagca ttctatgggc    360
aagctgaata tgttgcacta cttcccggat aaactgttca gcggctacga tattcagcgc    420
tggaagccag acccggcgtt aatgttccat gcggcaaaag cgatgaatgt aaatgtagaa    480
aactgcattc tggttgatga ctcagttgcc ggtgcacaat ctggtatcga cgcaggtatg    540
gaagtgttct acttctgcgc cgacccgcac aataagccga tcgttcaccc gaaagtcacc    600
acctttaccc atctttcgca gttacctgaa ctgtggaaag cgcgtggttg ggatattacg    660
gcatag                                                              666

<210> SEQ ID NO 41
<211> LENGTH: 813
<212> TYPE: DNA
<213> ORGANISM: E.coli

<400> SEQUENCE: 41
atggctatta aactcattgc tatcgatatg gatggcaccc ttctgctgcc cgatcacacc     60
atttcacccg ccgttaaaaa tgcgattgcc gcagctcgcg cccgtggcgt gaatgtcgtg    120
ctaacgacgg gtcgcccgta tgcaggtgtg cacaactacc tgaaagagct gcatatggaa    180
cagccgggcg actactgcat tacttataac ggcgcgctgg tacagaaggc cgctgatggt    240
agcaccgtgg cgcaaactgc tctcagctat gacgactatc gtttcctgga aaaactctct    300
cgcgaagtcg gttctcattt ccacgccctg accgcacca gctgtacac cgccaaccgt    360 gatatcagct actacacggt gcatgaatcc ttcgttgcca ccattccgct ggtgttctgc    420
gaagcggaga aaatggaccc caatacccag ttcctgaaag tgatgatgat tgatgaaccc    480
gccatcctcg accaggctat cgcgcgtatt ccgcaggaag tgaaagagaa atataccgtg    540
ctgaaaagtg cgccgtactt cctcgaaatc ctcgataaac gcgttaacaa aggtacgggg    600
gtgaaatcac tggccgacgt gttaggtatt aaaccggaag aaatcatggc gattggcgat    660
caggaaaacg atatcgcaat gattgaatat gcaggcgtcg gtgtggcgat ggataacgct    720
attccttcag tgaaagaagt ggcgaacttt gtcaccaaat ctaaccttga agatggcgtg    780
```

```
gcgtttgcta ttgagaagta tgtgctgaat taa                                  813
```

<210> SEQ ID NO 42
<211> LENGTH: 801
<212> TYPE: DNA
<213> ORGANISM: E.coli

<400> SEQUENCE: 42

```
atgtaccagg ttgttgcgtc tgatttagat ggcacgttac tttctcccga ccatacgtta     60
tccccttacg ccaaagaaac tctgaagctg ctcaccgcgc gcggcatcaa ctttgtgttt    120
gcgaccggtc gtcaccacgt tgatgtgggg caaattcgcg ataatctgga gattaagtct    180
tacatgatta cctccaatgg tgcgcgcgtt cacgatctgg atggtaatct gattttgct    240
cataacctgg atcgcgacat tgccagcgat ctgtttggcg tagtcaacga caatccggac    300
atcattacta acgtttatcg cgacgacgaa tggtttatga atcgccatcg cccggaagag    360
atgcgctttt ttaaagaagc ggtgttccaa tatgcgctgt atgagcctgg attactggag    420
ccggaaggcg tcagcaaagt gttcttcacc tgcgattccc atgaacaact gctgccgctg    480
gagcaggcga ttaacgctcg ttggggcgat cgcgtcaacg tcagtttctc taccttaacc    540
tgtctggaag tgatggcggg cggcgtttca aaaggccatg cgctggaagc ggtggcgaag    600
aaactgggct acagcctgaa ggattgtatt gcgtttggtg acgggatgaa cgacgccgaa    660
atgctgtcga tggcggggaa aggctgcatt atgggcagtg cgcaccagcg tctgaaagac    720
cttcatcccg agctggaagt gattggtact aatgccgacg acgcggtgcc gcattatctg    780
cgtaaactct atttatcgta a                                              801
```

<210> SEQ ID NO 43
<211> LENGTH: 567
<212> TYPE: DNA
<213> ORGANISM: E.coli

<400> SEQUENCE: 43

```
atgtacgagc gttatgcagg tttaatttt gatatggatg gcacaatcct ggatacggag     60
cctacgcacc gtaaagcgtg gcgcgaagta ttagggcact acggtcttca gtacgatatt    120
caggcgatga ttgcgcttaa tggatcgccc acctggcgta ttgctcaggc aattattgag    180
ctgaatcagg ccgatctcga cccgcatgcg ttagcgcgtg aaaaaacaga agcagtaaga    240
agtatgctgc tggatagcgt cgaaccgctt cctcttgttg atgtggtgaa agttggcat    300
ggtcgtcgcc caatggctgt aggaacgggg agtgaaagcg ccatcgctga ggcattgctg    360
gcgcacctgg gattacgcca ttattttgac gccgtcgtcg ctgccgatca cgtcaaacac    420
cataaacccg cgccagacac attttgttg tgcgcgcagc gtatgggcgt gcaaccgacg    480
cagtgtgtgg tctttgaaga tgccgatttc ggtattcagg cggcccgtgc agcaggcatg    540
gacgccgtgg atgttcgctt gctgtga                                        567
```

<210> SEQ ID NO 44
<211> LENGTH: 651
<212> TYPE: DNA
<213> ORGANISM: E.coli

<400> SEQUENCE: 44

```
gtgcggtgca aaggttttct gtttgatctt gatggaacgc tggtggattc cctgcctgcg     60
gtagaacggg cgtggagcaa ctgggccaga cgtcatgggt tagcgccgga agaggtgctg    120
```

```
gctttcattc acggtaaaca ggcgatcacc tctctgcgcc attttatggc gggcaaatcc    180
gaggctgata ttgccgccga gtttacgcgt ctggagcaca tcgaggccac ggaaaccgaa    240
ggtattaccg cgcttccggg ggcaatcgcc ttactcagtc atttgaataa agcaggtatt    300
ccgtgggcca ttgtgacttc tggctccatg ccggtagcgc gagcgcgcca taaaatagct    360
gggcttcccg caccagaggt gtttgtaacc gctgagcgag tgaagcgcgg aaaaccagaa    420
cctgatgcgt atctgttagg cgcgcagctg ctggggcttg cgccgcagga gtgtgtggtg    480
gtggaagatg ctcccgctgg cgtgctttct ggcctggcgg cgggttgtca tgtcattgcg    540
gttaacgctc cggcagatac cccgcgcctg aatgaggtcg atttggtcct ccacagtctg    600
gagcaaatta ctgtgaccaa acagccaaat ggcgatgtta ttattcagtg a              651
```

```
<210> SEQ ID NO 45
<211> LENGTH: 669
<212> TYPE: DNA
<213> ORGANISM: E.coli

<400> SEQUENCE: 45
atgtcaaccc cgcgtcagat tcttgctgca attttttgata tggatggatt acttatcgac    60
tcagaacctt tatgggatcg agccgaactg gatgtgatgg caagcctggg ggtggatatc   120
tcccgtcgta acgagctgcc ggacacctta ggtttacgca tcgatatggt ggtcgatctt   180
tggtacgccc ggcaaccgtg gaatgggcca agccgtcagg aagtagtaga acgggttatt   240
gcccgtgcca tttcactggt tgaagagaca cgtccattat taccaggcgt gcgcgaagcc   300
gttgcgttat gcaaagaaca aggtttattg gtgggactgg cctccgcgtc accactacat   360
atgctggaaa aagtgttgac catgtttgac ttacgcgaca gtttcgatgc cctcgcctcg   420
gccgaaaaac tgccttacag caagccgcat ccgcaagtat atctcgactg cgcagcaaaa   480
ctgggcgttg accctctgac ctgcgtagcg ctggaagatt cggtaaatgg catgatcgcc   540
tctaaagcag cccgcatgcg ttccatcgtc gttcctgcgc cagaagcgca aaatgatcca   600
cgttttgtat tagcagacgt caaactttca tcgctgacag aactcaccgc aaaagacctt   660
ctcggttaa                                                             669
```

```
<210> SEQ ID NO 46
<211> LENGTH: 1080
<212> TYPE: DNA
<213> ORGANISM: E.coli

<400> SEQUENCE: 46
atgtctaaga tttttgattt cgtaaaacct ggcgtaatca ctggtgatga cgtacagaaa    60
gttttccagg tagcaaaaga aaacaacttc gcactgccag cagtaaactg cgtcggtact   120
gactccatca acgccgtact ggaaaccgct gctaaagtta agcgccggt atcgttcag    180 ttctccaacg gtggtgcttc ctttatcgct ggtaaaggcg tgaaatctga cgttccgcag   240
ggtgctgcta tcctgggcgc gatctctggt gcgcatcacg ttcaccagat ggctgaacat   300
tatggtgttc cggttatcct gcacactgac cactgcgcga gaaactgct gccgtggatc   360 gacggtctgt tggacgcggg tgaaaaacac ttcgcagcta ccgtaagcc gctgttctct   420 tctcacatga tcgacctgtc tgaagaatct ctgcaagaga acatcgaaat ctgctctaaa   480
tacctggagc gcatgtccaa aatcggcatg actctggaaa tcgaactggg ttgcaccggt   540
ggtgaagaag acggcgtgga caacagccac atggacgctt ctgcactgta cacccagccg   600
gaagacgttg attacgcata caccgaactg agcaaaatca gcccgcgttt caccatcgca   660
```

```
gcgtccttcg gtaacgtaca cggtgtttac aagccgggta acgtggttct gactccgacc    720
atcctgcgtg attctcagga atatgttccc aagaaacaca acctgccgca acacagcctg    780
aacttcgtat tccacggtgg ttccggttct actgctcagg aaatcaaaga ctccgtaagc    840
tacggcgtag taaaaatgaa catcgatacc gatacccaat gggcaacctg ggaaggcgtt    900
ctgaactact acaaagcgaa cgaagcttat ctgcagggtc agctgggtaa cccgaaaggc    960
gaagatcagc cgaacaagaa atactacgat ccgcgcgtat ggctgcgtgc cggtcagact   1020
tcgatgatcg ctcgtctgga gaaagcattc caggaactga acgcgatcga cgttctgtaa   1080
```

<210> SEQ ID NO 47
<211> LENGTH: 1053
<212> TYPE: DNA
<213> ORGANISM: E.coli

<400> SEQUENCE: 47

```
atgacagata ttgcgcagtt gcttggcaaa gacgccgaca accttttaca gcaccgttgt     60
atgacaattc cttctgacca gctttatctc cccggacatg actacgtaga ccgcgtaatg    120
attgacaata atcgcccgcc agcggtgtta cgtaatatgc agacgttgta acaccaccggg   180 cgtctggctg gcacaggata tctttctatt ctgccggttg accagggcgt tgagcactct    240
gccggagctt catttgctgc taacccgctc tactttgacc cgaaaaacat tgttgaactg    300
gcgatcgaag cgggctgtaa ctgtgtggcg tcaacttacg gcgtgctggc gtcggtatcg    360
cggcgttatg cgcatcgcat tccattcctc gtcaaactta atcacaacga acgctaagt    420 tacccgaata cctacgatca aacgctgtat gccagcgtgg agcaggcgtt caacatgggc    480
gcggttgcgg ttggtgcgac tatctatttt ggctcggaag agtcacgtcg ccagattgaa    540
gaaatttctg cggcttttga acgtgcgcac gagctgggta tggtgacagt gctgtgggcc    600
tatttgcgta actccgcctt taagaaagat ggcgttgatt accatgtttc cgccgacctg    660
accggtcagg caaaccatct ggcggcaacc atcggtgcag atatcgtcaa acaaaaaatg    720
gcggaaaata acggcggcta taaagcaatt aattacggtt acaccgacga tcgtgtttac    780
agcaaattga ccagcgaaaa cccgattgat ctggtgcgtt atcagttagc taactgctat    840
atgggtcggg ctgggttgat aaactccggc ggtgctgcgg gcggtgaaac tgacctcagc    900
gatgcagtgc gtactgcggt tatcaacaaa cgcgcaggcg aatgggggct gattcttgga    960
cgtaaagcgt tcaagaaatc gatggctgac ggcgtgaaac tgattaacgc cgtgcaggac   1020
gtttatctcg atagcaaaat tactatcgcc tga                                 1053
```

<210> SEQ ID NO 48
<211> LENGTH: 849
<212> TYPE: DNA
<213> ORGANISM: Corynebarium glutamicum (strain R)

<400> SEQUENCE: 48

```
atgcatcatc atcaccatca catgaccgtg aatattagct atctgaccga tatggatggc     60
gtgctgatta agaaggtgaa atgattccg ggtgccgatc gttttctgca aagcctgaca    120
gataataacg tggaatttat ggtgctgacc aacaacagca ttttttacacc gcgtgatctg    180 agcgcacgtc tgaaaaccag cggtctggat attccgcctg aacgtatttg gaccagcgca    240
accgccaccg cacattttct gaaaagtcag gtgaaagaag gcaccgcata cgttgttggt    300
gaaagcggtc tgaccaccgc actgcatacc gcaggttgga ttctgacaga tgcaaatccg    360
```

```
gaatttgttg ttctgggtga aacccgtacc tatagctttg aagcaattac caccgccatt      420
aatctgattt taggtggtgc acgtttcatt tgtaccaatc cggatgttac cggtccgagt      480
ccgagcggta ttctgcctgc aaccggtagc gttgcagcac tgattaccgc agcaaccggt      540
gcagaaccgt attacattgg taaaccgaat cctgtgatga tgcgtagcgc actgaatacc      600
attggtgcac atagcgaaca taccgttatg attggtgatc gtatggatac cgatgttaaa      660
agtggtctgg aagcaggtct gagtaccgtt ctggttcgta cggtatttc agatgatgca       720 gaaattcgtc gttatccgtt tcgtccgaca catgtgatta tagcattgc cgatctggca       780 gattgttggg atgatccgtt tggtgatggt gcatttcatg ttccggatga acagcagttt      840
accgattaa                                                              849

<210> SEQ ID NO 49
<211> LENGTH: 651
<212> TYPE: DNA
<213> ORGANISM: Listeria monocytogenes serotype 1/2a (strain 10403S)

<400> SEQUENCE: 49
atgcatctgg atagcgcaaa tctggatgac gtgaaaaaaa tccaggcaag cagcatcttt      60
aaaggcatta ccaccaatcc gagcattctg gttaaagaaa atgtaatcg tcagaccgcc       120 attaaccgta ttctggaact gaccgataaa caggttttg ttcagaccgt tggctttacc       180
tatgaagaaa ttctggcaga tgcacgtatg ctgctgacca tgtttggtaa agacaaaatc      240
gcaatcaaaa ttccggcaca tgaagcaggc accatgttta ttgataccct gaaaaaagag      300
gacaaaacca ttcagattct gggcaccgca atttatagcg cagatcaggc aattaccgca      360
gcactggcag gcgcagattt tgttgcaccg tatgttaatc gtatgagcgc agcaaatatc      420 gacccgtttta aagaaattac ccagatgcgc cacttcttcg ataaaaagc actgaaaacc      480 cagattatgg cagccagctt taaacatagc ggtcaggtta tgcaggccta tgaaagcggt      540
gcagataccg ttaccattcc gtatgaaatc tatagccaga tgaccaataa agttctggca      600
gttgaagcca ttcgcgtgtt taatgaagat gcagttctgt acgagaaatg a              651

<210> SEQ ID NO 50
<211> LENGTH: 669
<212> TYPE: DNA
<213> ORGANISM: Streptococcus pyogenes serotype M1

<400> SEQUENCE: 50
atggaatata tgctggatac cctggatctg gaagcaatca aaaatggca tcacattctg        60 ccgctggcag gcgttaccag caatccgagc attgcaaaaa agaaggcga gatcgatttt       120 tttgaacgca ttcgtgaagt gcgtgccatt attggtgata agcaagcat tcatgttcag       180 gttattgccc aggattatga aggcattctg aaagatgcag cagaaattcg tcgtcagtgt      240
ggtgatagcg tttatgttaa agttccggtt accaccgaag gtctggcagc aattaaaacc      300
ctgaaagcag aaggttatca tattaccgca accgcaattt ataccacctt tcagggcctg      360
ctggcaattg aagccggtgc agattatctg ctccgtatt ataaccgtat ggaaaatctg       420
aacattgatc cggaagcagt tattgaacag ctggccgaag caattaatcg tgaaaatgcc      480
aatagcaaaa ttctggcagc cagctttaaa acgttgccc aggtgaataa agttttgca       540 ctgggtgcac aggcaattac cgcaggtccg gatgtttttg aagcaggttt tgccatgccg      600
agcattcaga aagcagttga tgattttggt aaagactggg aagcaattca tcaccgcaaa      660
agcatctga                                                              669
```

```
<210> SEQ ID NO 51
<211> LENGTH: 669
<212> TYPE: DNA
<213> ORGANISM: Streptococcus gordonii

<400> SEQUENCE: 51
atggaattta tgctggatac cctgaacctg gaagaaatca aaaaatggtc agaagttctg      60
ccgctggcag gcgttaccag caatccgacc attgcaaaaa aagaaggcaa aatcgacttt     120
ttcgaacgca ttagcgcagt gcgtgaaatt attggtgaag gtccgagcat tcatgttcag     180
gttgttgcaa aagattatga gggcattctg aaagatgcag ccaccattcg taaaaaatgt     240
ggtgatgccg tgtatatcaa aattccggtt acaccggatg gtctggcagc aattaaaacc     300
ctgaaagcag aaggctataa aatcaccgca accgcaattt ataccacctt tcagggcctg     360
ctggcaattg aagcagaagc agattatctg gcaccgtatt ataccgtat ggaaaatctg      420 aacatcgatt ccgatgcagt tattagtcag ctggcacagg ccattgaacg tgatcatagc     480
gatagcaaaa ttctggcagc cagctttaaa aacgttgcac aggttaatcg tgcatttgca     540
gatggtgcac aggcagttac cgcaggtccg atgttttttg cagcagcatt tgcaatgccg     600
agtattgcaa aagcagttga tgattttgca accgattgga gcgatattca cagccaagaa     660
tatgtgtga                                                              669

<210> SEQ ID NO 52
<211> LENGTH: 678
<212> TYPE: DNA
<213> ORGANISM: Enterococcus faecalis (EnGen0302)

<400> SEQUENCE: 52
atggaattta tgctggacac cattaacctg gaagccattc gtaaatatca gaaaattctg      60
ccgctggcag gcgttaccag caatccgagc attgttaaac aggcaggcaa aattgatttt     120
tttgcccaga tgaaagaaat caaaaagacc attggtcagg caagcctgca tgttcaggtt     180
gttggtcaga ccaccgaaga aatgctggaa gatgcacaga ccattgtgca gcagctgggt     240
caagaaacct ttatcaaaat tccggttaat gaagcaggtc tggcagcaat taaacagctg     300
aaacaggcaa attatcgtat taccgcaacc gccatttata ccgaatttca gggttatctg     360
gcaattgcag ccggtgcaga ttacctggca ccgtattata ccgtatgga aaatctgacc      420 atcgacagcc agaaagttat tgaacatctg gcagccgaaa ttaaacgtac caatgccaaa     480
agcaaaattc tggcagcgag ctttaaaaac gttgcgcaga ttaatcaggc atgtcagatg     540
ggtgcacagg cagttaccat tgcaccggaa ctggttaccc aaggtctggc catgcctgca     600
attcagaaag cagttaccga ttttcaagaa gattgggttg cagtttttgg tgtggaaacc     660
gttaatgaac tggcctga                                                    678

<210> SEQ ID NO 53
<211> LENGTH: 648
<212> TYPE: DNA
<213> ORGANISM: Clostridium beijerinckii (Clostridium MP)

<400> SEQUENCE: 53
atgcgctttt ttctggatac cgccaacgtg atcatatta aagaagcaaa tgaaatgggc      60
gtgatttgtg gtgttaccac caatccgagc ctggttgcaa aagaaggtcg cgatttttaac    120 gaagtgatca aagaaattac cgagattgtg gatggtccga ttagcggtga agttgttgcc    180
```

```
gaagatgcac agggtatgat taaagaggga cgcgaaattg cagccatcca taaaaacatg    240
attgtgaaaa ttccgatgac cgcagaaggt ctgaaagcaa ccaaagttct gagcagcgaa    300
ggtattaaaa ccaatgtgac cctgattttt agcgcaaccc agagcctgct ggcagcaaat    360
gccggtgcaa cctatgttag cccgtttctg ggtcgtgttg atgatattag catgattggt    420
atggatctgg ttcgtgatat tgccgaaatt tttgccgttc atggtatcga aaccgaaatc    480
attgcagcaa gcgttcgtaa tccgattcat gttattgaag cagcaaaagc gggtgccgat    540
attgcaacca ttccgtatgc actggttatg cagatgctga atcatccgct gaccgatcaa    600
ggtctggaaa aattcaaagc agattgggca gcagcattcg gcaaatga                648

<210> SEQ ID NO 54
<211> LENGTH: 654
<212> TYPE: DNA
<213> ORGANISM: Caulobacter vibrioides (strain ATCC 19089)

<400> SEQUENCE: 54
atgcagattt ttctggatag caccgacacc aaagttattg ccgatctggc aagcaccggt     60
ctgattgatg gtgttaccac caatccgaca ctgattgcaa aaagcggtcg tccgatgctg    120
gaagtgattg cagaaatttg tgatattgtt ccgggtccga ttagcgcaga agttgcagca    180
accaccgcag atgcaatgat tgccgaaggt cagaaactgg caaaaattgc accgaatgtt    240
gttgtgaaaa ttccgctgac acgtgatggc ctgattgcat gtgcagcatt tgcagatgaa    300
gaaatcaaaa ccaatgtgac cctgtgtttt agcccgacac aggcactgct ggcagcaaaa    360
gccggtgcaa cctatattag cccgtttatt ggtcgtctgg atgattatgg ctttgatggt    420
atggatctga ttcgtgatat tcgtgccatc tatgataact atggctatga aaccgaaatt    480
ctggcagcca gcgttcgtaa tgcagcacat gttaaagaag cagcaattgt tggcgcagat    540
gttgttacca ttcctccggc agttttagc gatctgtata acatccgct gaccgataaa    600 ggtctggaac agttcctgaa agattgggca tcaaccggtc agagcattct gtaa          654

<210> SEQ ID NO 55
<211> LENGTH: 669
<212> TYPE: DNA
<213> ORGANISM: Streptococcus suis

<400> SEQUENCE: 55
atggaattta tgctggacac cctgaacatt gaagaaattc gtaaatgggc agaagtgctg     60
ccgctggcag gcgttaccag caatccgacc attgcacgta agaaggtga catagatttt    120 tttgaacgcc tgcatctgat tcgcgatatt attggtccga atgcaagcct gcatgttcag    180
gttgttgcaa aagattatga aggtattctg gccgacgcga aaaaaatccg tgaactggca    240
ccggaaaaca tctatatcaa agttccggtt acaccggcag tctggcagc aatgaaaacc    300 ctgaaagcac agggttatca gattaccgca accgcaattt ataccgtttt tcagggtctg    360
ctggcaattg aagccggtgc agattatctg gctccgtatt ataaccgtat ggccaacctg    420
aatattgata gcaatgcagt tattgcacag ctgagcgaag caattgatcg tgaatgtagc    480
gaaagcaaaa ttctggcagc cagctttaaa acgttgatc aggttaatca ggcctttgca    540
aatggtgcac aggcaattac cgcaggcgca gatatttttg aagcagcatt tagtatgccg    600
agcattgaaa aagccgttaa cgattttgca gatgattgga gcgcaattca tggtcgttat    660
accatctga                                                             669
```

```
<210> SEQ ID NO 56
<211> LENGTH: 669
<212> TYPE: DNA
<213> ORGANISM: Streptococcus mutans serotype C (strain ATCC 700610)

<400> SEQUENCE: 56
atggaattta tgctggatac cctgaacctg gccgatattg aaaaatgggc agcaattctg      60
ccgctggcag gcgttaccag caatccgagc attgcaaaaa agaaggcaa aatcgacttc      120 tttgaacagg ttaaacgtgt gcgtgcaatt attggtgaag aaccgagcat tcatgcacag      180
gttgttgcag cagatgttga aggtattatc aaagatgccc acaaactgca agatgaatta      240
ggtggtaatc tgtatgttaa agttccggtt agcccgaccg gtctgaccgc aatgaaacag      300
ctgaaagaag aaggttttca gattaccgca accgccattt ataccgtttt tcagggtctg      360
ctggcaattg aagccggtgc agattatctg gctccgtatt ataaccgtat ggaaaacctg      420
aacattgatc cgattgaagt tattggtcag ctggcacagg ccattgaatg tcagcaggca      480
agcgcaaaaa ttctggcagc cagctttaaa aacgttaccc aggttgcaaa agcactggca      540
gccggtgcca aagcagttac cgcaggcgca gatattttg cagcaggttt tgcaaatccg      600
agtattcaga aagccgttga tgattttgca gccgattggg aaagcaccca gggtcgtccg      660
tatatctaa                                                              669

<210> SEQ ID NO 57
<211> LENGTH: 669
<212> TYPE: DNA
<213> ORGANISM: Streptococcus agalactiae serotype III (strain NEM316)

<400> SEQUENCE: 57
atggaatttc tgctggatac cctgaatctg gaagcaatca aaaaatggca tcacattctg      60
ccgctggcag gcgttaccag caatccgacc attgcaaaaa agaaggcga catccatttt      120 tttcagcgca ttcgtgatgt gcgcgaaatt attggtcgtg aagcaagcct gcatgttcag      180
gttgttgcaa aagattatca gggcattctg gatgatgcag ccaaaattcg tcaagaaacc      240
gatgatgaca tctacattaa agttccggtt acaccggatg gtctggcagc aattaaaaacc     300 ctgaaagcag aaggttataa cattaccgca accgccattt ataccagtat gcagggtctg      360
ctggcaatta tgccggtgc agattatctg gctccgtatt ttaaccgtat ggaaaacctg      420
gatattgatg cgacccaggt tattaaagaa ctggcacagg caattgaacg taccggtagc      480
agcagcaaaa ttctggcagc cagctttaaa aacgcaagcc aggttaccaa agcactgagc      540
cagggtgcac agagtattac cgcaggtccg gatattttg aaagcgtttt tgccatgccg      600
agcattgcca aagcagttaa tgattttgca gatgattgga agccagcca gcatagcgaa      660 catatctaa                                                              669

<210> SEQ ID NO 58
<211> LENGTH: 669
<212> TYPE: DNA
<213> ORGANISM: Streptococcus pneumoniae

<400> SEQUENCE: 58
atggaattta tgctggatac cctgaacctg gatgaaatca aaaaatggtc agaaattctg      60
ccgctggcag gcgttaccag caatccgacc attgcaaaac gtgaaggtag catcaacttt      120
ttcgaacgca ttaaagatgt gcgcgaactg attggtagca ccccgagcat tcatgttcag      180
gttattagcc aggattttga gggcattctg aaagatgcac ataaaattcg tcgtcaagcc      240
```

```
ggtgatgaca tctttatcaa agttccggtt acaccggcag gtctgcgtgc aattaaagca    300
ctgaaaaaag aaggctatca tattaccgca accgccattt ataccgttat tcagggtctg    360
ctggcaattg aagccggtgc agattatctg ctccgtatt ataaccgtat ggaaaatctg    420
aacatcgaca gcaatagcgt tattcgtcag ctggcactgg ccattgatcg tcagaatagc    480
ccgagcaaaa ttctggcagc cagctttaaa acgttgccc aggttaataa tgcactggca    540
gcgggtgcac atgcagttac cgcaggcgca gatgttttg aaagcgcatt tgcaatgccg    600
agtattcaga aagcagtgga tgattttcc gatgattggt ttgttaccca gaatagtcgc    660
agcatctga                                                           669
```

```
<210> SEQ ID NO 59
<211> LENGTH: 747
<212> TYPE: DNA
<213> ORGANISM: Pyrococcus horikoshii (strain ATCC 700860)

<400> SEQUENCE: 59
atgcatcatc atcatcatca catggtgaaa gtgatctttt tcgatctgga tgataccctg     60
gttgatacca gcaaactggc agaaattgca cgtaaaaatg ccatcgaaaa tatgattcgt    120
catggtctgc cggttgattt tgaaaccgca tatagtgaac tgatcgagct gattaaagaa    180
tacggtagca acttttccgta tcacttcgat tatctgctgc gtcgtctgga tctgccgtat    240
aatccgaaat ggattagtgc cggtgttatc gcatatcaca ataccaaatt tgcctatctg    300
cgtgaagttc cgggtgcgcg taaagttctg attcgtctga agaactggg ttatgaactg    360 ggcattatta ccgatggtaa tccggttaaa cagtgggaaa aaattctgcg tctggaactg    420
gatgattttt ttgaacatgt gatcatcagc gatttcgagg gtgttaaaaa accgcatccg    480
aaaatcttca aaaagccct gaaagccttt aacgtgaaac cggaagaggc actgatggtt    540
ggtgatcgtc tgtatagcga tatttatggt gcaaaacgtg tgggtatgaa aaccgtttgg    600
tttcgctatg gtaaacatag tgaacgcgaa ctggaatatc gtaaatatgc cgattatgag    660
atcgacaatc tggaaagcct gctggaagtt ctggcacgtg aaagcagcag caacaaaaaa    720
gttcatccgc ctcgtcagca gatttga                                        747
```

```
<210> SEQ ID NO 60
<211> LENGTH: 708
<212> TYPE: DNA
<213> ORGANISM: Methanocaldococcus jannaschii (strain ATCC 43067)

<400> SEQUENCE: 60
atgcatcatc atcaccatca catgattaaa ggcatcctgt tgatctgga tgataccctg      60 tataacagca gcgaatttgt tgaaattgca cgtcgtgaag cagtgaaaag catgattgat    120
gcaggtctga acatcgattt tgaagaagcc atgaacatcc tgaacaagat catcaaagat    180
aagggcagca ctatggcaa acatttcgat gatctggtta agccgttct gggtaaaatat    240 gatccgaaaa ttatcaccac cggcattatc acctatcaca atgtgaaagt tgcactgctg    300
cgtccgtatc cgcataccat taaaaccctg atggaactga agcaatggg tctgaaactg    360 ggtgttatta ccgatggtct gaccattaaa cagtgggaaa aactgattcg tctgggcatt    420
catccgtttt ttgatgatgt gattaccagc gaagaatttg gtctgggcaa accgcatctg    480 gaattttttca aatatggcct gaaacgtatg ggcctgaaag ccgaagaaac cgtttatgtt    540
ggtgatcgtg tggacaaaga tattaagcct gcaaagaac tggcatgat taccgttcgt    600 attctgaaag gcaaatacaa agacatggaa gatgatgagt atagcgacta caccattaat    660
```

```
agcctgcaag agctggttga cattgtgaaa aacctgaaaa aggattaa              708
```

<210> SEQ ID NO 61
<211> LENGTH: 1116
<212> TYPE: DNA
<213> ORGANISM: Homo sapiens (Human)

<400> SEQUENCE: 61

```
atgcatcatc atcaccatca catggcacat cgttttccgg cactgaccca agaacagaaa   60
aaagaactga gcgaaattgc ccagagcatt gttgcaaatg gtaaaggtat tctggcagca  120
gatgaaagcg ttggtacaat gggtaatcgt ctgcaacgta ttaaagtgga aaacaccgaa  180
gaaaatcgtc gtcagtttcg tgaaattctg tttagcgttg atagcagcat taatcagagt  240
attggtggcg tgattctgtt ccatgaaacc ctgtatcaga agatagcca gggtaaactg   300
tttcgcaaca tcctgaaaga aaaaggtatt gtggtgggca tcaaactgga tcaaggtggt  360
gcaccgctgg caggcaccaa taagaaacc accattcaag gtctggatgg tctgagcgaa  420
cgttgtgcac agtacaaaaa agatggtgtg gattttggta aatggcgtgc agttctgcgt  480
attgcagatc agtgtccgag cagcctggca attcaagaaa atgcaaatgc actggcacgt  540
tatgcaagca tttgtcagca gaatggtctg gttccgattg ttgaaccgga agttattccg  600
gatggtgacc atgatctgga acattgtcag tatgttaccg aaaaagtgct ggcagccgtt  660
tataaagcac tgaatgatca tcatgtttac ctggaaggca ccctgctgaa accgaatatg  720
gttaccgcag gtcatgcatg taccaaaaaa tacacaccgg aacaggttgc aatggcaacc  780
gttaccgcac tgcatcgtac cgttccggca gcagttccgg gtatttgttt tctgagcggt  840
ggtatgagcg aagaagatgc aaccctgaat ctgaatgcaa ttaatctgtg tccgctgccg  900
aaaccgtgga aactgagctt tagctatggt cgtgcactgc aagcaagcgc actggcagca  960
tggggtggta aagcagcaaa taagaagca cccaagagg cctttatgaa acgtgcaatg  1020
gccaattgtc aggcagcaaa aggccagtat gttcataccg gtagcagcgg tgccgcaagc  1080
acccagagcc tgtttaccgc atgttatacc tattga                           1116
```

<210> SEQ ID NO 62
<211> LENGTH: 1653
<212> TYPE: DNA
<213> ORGANISM: Aeromonas hydrophila subsp. hydrophila (strain ATCC
       7966)

<400> SEQUENCE: 62

```
atggcacagc atagccatgc aggtcagcct gcacgtctga gcgatctgac caatattccg   60
cgtctggtta gcgcatatta tctgaataaa ccggatatga ccgtccgga acagcgtgtt  120
gcatttggca ccagcggtca tcgtggtagc gcactgcata tgcatttac cgaaagccat  180
attctggcag ttacccaggc actggttgaa tatcgtcagc aggcaggtat taccggtccg  240
ctgtttgttg gtatggatac ccatgcactg agcgaaagcg catttgcaag cgcagttgaa  300
gttctggcag caaatggtgt tgaaacccgt attcaggcag tctgggtttt accccgaca   360
ccggttatta gccatgccat tctgcgtcat aatgcaggta aaccggcagc acgtgcagat  420
ggtgttgtta ttaccccgag ccataatccg cctgaagatg gtggctttaa atacaatccg  480
cctcatggtg gtcctgccga aggtgaaatt acaaaatggg ttgaagatcg tgccaatgca  540
attctggaag ccggtctggc aggcgttaaa cgtatggcat ttcagaaagc actgaaaagc  600
ccgtttgttg cactgcatga ttatgttacc ccgtatgttg atgatctgaa aaacgttctg  660
```

```
gatatggatg ccattaaaca ggcaggcatt aaaatcggtg ttgatccgtt aggtggtagc      720
ggtgttgcct attgggatgt tattgcaaaa acctatggcc tgaatatcga ggtggtgaac      780
tataaagttg atccgacctt tagctttatg accctggata agatggcaa  aattcgtatg      840 gattgtagca gtccgtttgc aatggcaagc ctgattgcac tgaaagacaa atttgatatt      900
gcgctgggta acgatccgga ttatgatcgt catggtattg ttaccaaaag cggtctgatg      960
aatccgaatc attatctggc cgttgcaatt cagtacctgt ttacccatcg taccggttgg     1020
agcaaagaaa gcgctgttgg caaaaccctg gttagcagca gcatgattga tcgtgttgcc     1080
ggtgaaattg tcgtaccct  gaaagaagtt ccggttggtt taaatggtt  tgtggatggt     1140 ctgtatagcg gtgaatttgg ttttggtggt gaagaaagtg ccggtgccag ctttctgcgt     1200
aaagatggta cagtttggac caccgataaa gacggtttta ttctggccct gctggcagca     1260
gaaattctgg ccgtgaccgg taaagatccg cagacacatt atgatgcact ggaagcaaaa     1320
tttggtcgta gcagctatcg tcgtattgat gcaccggcaa atagcgcaca gaaagcagtt     1380
ctgagcaaat tagatccggc actggtggaa gcaagcacct tagccggtga accgattatt     1440
gccaaactga ccaaagcacc gggtaatgat gcagcaattg gtggtctgaa agttgttacc     1500
gaaaatggtt ggtttgcagc acgtccgagc ggcaccgaaa gcatctataa aatctatatg     1560
gaatccttca aaggcgaagc acatctggat ctgattcagc aagaagcaca gcagattgtt     1620
agcgcagcac tggcaaaagc cggtgtttaa taa                                  1653
```

<210> SEQ ID NO 63
<211> LENGTH: 1365
<212> TYPE: DNA
<213> ORGANISM: Aeromonas hydrophila subsp. hydrophila (strain ATCC
    7966)

<400> SEQUENCE: 63

```
atgaatctga cctgtttcaa agcctatgac attcgtggta aactgggtga tgaactgaat       60
atcgaaattg cctatcgtat tggtcgtgca accgcacagt atctgaaagc aacccgtatt      120
gcagttggtg gtgatgttcg tctgaccagc gaaggtctga acaggcact  ggcaaatggt      180 attctggatg caggttgtga tgttattgat ctgggtgtta ccggcaccga agaaacctat      240
ttcgcagcat ttaccctgga tattgatggt gcaattgaag ttaccgcaag ccataatccg      300
atggattaca atggtatgaa actggttggt cgtgatgcat gtccgattag cggtgatagc      360
ggtctgaatg atattcgtgc actggcagaa aaaggtgatt ttagcgttag ctttcgtcgt      420
ggcaccctga gcaaaaaaag catcctggat gcctatgttg atcatctgct gacctatatc      480
aaaccgcatc agctgcgtcc gctgaaatta gttgttaatg caggtaatgg tgcagccggt      540
catgttatcg atgtgattga acagcgtttt aacattctga acatcccggt ggaatttatc      600
aaaatccatc atgaagaaaa cggcaacttt ccgaatggca ttccgaatcc gctgctgccg      660
gaaaatcgtg atgttaccag tgaagcagtt aaactgcatc atgcagatat gggtattgca      720
tgggatggtg attttgatcg ctgttttctg tttgatgaga cggcattttt tatcgagggc      780
tattatatcg ttggtctgct ggcagaagca tttctggttg aaaatccgca tgaacgcatt      840
attcatgatc cgcgtctgac ctggaatacc atcgatattg ttgaaaaaag cggtggtatt      900
ccggttcagt caaaaaccgg tcatgccttt atcaaagaac gtatgcgtag cgaaaatgcc      960
atttatggtc gtgaaatgag cgcacatcat tattttcgcg atttggtta  ttgcgatagc     1020 ggtatgattc cgtggctgct ggttattaat ctgctgagcc tgaaaaatag cacccctgtca     1080
```

```
agcctggttg cagaacgtgt taaagcatat ccgtgtagcg gtgaaattaa ctatcgtgtt    1140
gataacgccc tggaaatcat caaaaaactg gaagaggttt atgttccgct ggccgttaaa    1200
gttgaatatg ttgatggtct gagcatcgag atgaatgatt ggcgttttaa tgtgcgcatt    1260
agcaatacag aacctctgct gcgtctgaat gttgaaagca aaaacaacat tagcaaactg    1320
accagtggtc tgaatagcct gcataagatg attaacaaca tctaa                  1365
```

```
<210> SEQ ID NO 64
<211> LENGTH: 317
<212> TYPE: PRT
<213> ORGANISM: E.coli

<400> SEQUENCE: 64
```

```
Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
    130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Tyr Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
    210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
    290                 295                 300

Asp Gln Glu Lys Leu Glu Lys Met Ile Gly Asp Leu Leu
305                 310                 315
```